(12) United States Patent
Okada et al.

(10) Patent No.: US 9,690,217 B2
(45) Date of Patent: Jun. 27, 2017

(54) TRIARYLAMINE DERIVATIVE, ELECTROPHOTOGRAPHIC PHOTOSENSITIVE MEMBER, AND IMAGE FORMING APPARATUS

(71) Applicant: KYOCERA Document Solutions Inc., Osaka (JP)

(72) Inventors: Hideki Okada, Osaka (JP); Fumio Sugai, Osaka (JP); Kensuke Kojima, Osaka (JP); Hiroki Tsurumi, Osaka (JP); Yohei Yamamoto, Osaka (JP); Eiichi Miyamoto, Osaka (JP)

(73) Assignee: KYOCERA Document Solutions, Inc., Osaka (JP)

( * ) Notice: Subject to any disclaimer, the term of this patent is extended or adjusted under 35 U.S.C. 154(b) by 0 days.

(21) Appl. No.: 14/837,298

(22) Filed: Aug. 27, 2015

(65) Prior Publication Data
US 2016/0062253 A1  Mar. 3, 2016

(30) Foreign Application Priority Data

Aug. 28, 2014  (JP) .................. 2014-174526
Aug. 28, 2014  (JP) .................. 2014-174527

(51) Int. Cl.
*G03G 5/06* (2006.01)
*G03G 5/04* (2006.01)
(Continued)

(52) U.S. Cl.
CPC .......... *G03G 5/0614* (2013.01); *C07C 211/54* (2013.01); *C07C 217/80* (2013.01); *G03G 5/04* (2013.01); *G03G 5/0672* (2013.01)

(58) Field of Classification Search
CPC .... G03G 5/0614; C07C 211/54; C07C 217/80
(Continued)

(56) References Cited

U.S. PATENT DOCUMENTS 4,769,302 A * 9/1988 Ueda .................... G03G 5/0614
430/58.15
5,008,706 A * 4/1991 Ohmori ................ G03G 15/751
361/225
(Continued)

FOREIGN PATENT DOCUMENTS

CN    102262362 A    11/2011
JP    S62-264058 A   11/1987
(Continued)

OTHER PUBLICATIONS

English language machine translation of JP 2007-210954 (Aug. 2007).*
Diamond, Arthur S (editor) Handbook of Imaging Materials. New York: Marcel-Dekker, Inc. (2002) pp. 164-168.*
Borsenberger, Paul et al. Organic Photoreceptors for Imaging Systems. New York: Marcel-Dekker, Inc. (1993) pp. 6-17.*

*Primary Examiner* — Christopher Rodee
(74) *Attorney, Agent, or Firm* — Studebaker & Brackett PC

(57) ABSTRACT

A triarylamine derivative is represented by general formula (I). In general formula (I), $R_1$ and $R_2$ each represent, independently of one another, a chemical group selected from the group consisting of a halogen atom, an optionally substituted alkyl group having a carbon number of 1-6, an optionally substituted alkoxy group having a carbon number of 1-6, and an optionally substituted aryl group having a carbon number of 6-12. In general formula (I), k and l each represent an integer of at least 0 and no greater than 4. When k and l represent integers greater than 1, chemical groups $R_1$ bonded to the same aromatic ring and chemical groups $R_2$ bonded to the same aromatic ring may be the same or different to one another. In general formula (I), m and n each represent a different integer of at least 1 and no greater than 3.

(Continued)

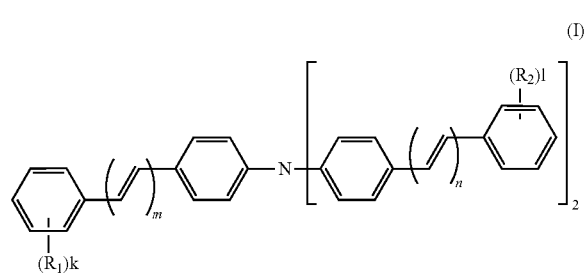

(I)

8 Claims, 5 Drawing Sheets

(51) Int. Cl.
  *C07C 211/54* (2006.01)
  *C07C 217/80* (2006.01)
(58) Field of Classification Search
  USPC .................................................. 430/58.85
  See application file for complete search history.

(56) References Cited

U.S. PATENT DOCUMENTS

| 5,363,176 | A | * | 11/1994 | Ishihara | G03G 15/1685 361/225 |
| 6,022,997 | A | * | 2/2000 | Endoh | C07C 209/10 564/412 |
| 8,026,027 | B2 | * | 9/2011 | Wu | G03G 5/0514 430/58.8 |
| 8,859,818 | B2 | | 10/2014 | Nakamura et al. | |
| 2009/0325096 | A1 | * | 12/2009 | Wu | G03G 5/0535 430/58.85 |
| 2012/0022293 | A1 | | 1/2012 | Nakamura et al. | |

FOREIGN PATENT DOCUMENTS

| JP | S64-013553 A | | 1/1989 |
| JP | H06-332206 A | | 12/1994 |
| JP | 2007-210954 A | | 8/2007 |
| JP | 2007210954 A | * | 8/2007 |
| JP | 2012-008523 A | | 1/2012 |
| JP | 2012-027139 A | | 2/2012 |
| JP | 2012-047959 A | | 3/2012 |

* cited by examiner

TRIARYLAMINE DERIVATIVE, ELECTROPHOTOGRAPHIC PHOTOSENSITIVE MEMBER, AND IMAGE FORMING APPARATUS

INCORPORATION BY REFERENCE

The present application claims priority under 35 U.S.C. §119 to Japanese Patent Application No. 2014-174527, filed on Aug. 28, 2014 and Japanese Patent Application No. 2014-174526, filed on Aug. 28, 2014. The contents of these applications are incorporated herein by reference in their entirety.

BACKGROUND

The present disclosure relates to triarylamine derivatives, electrophotographic photosensitive members, and image forming apparatuses.

Electrophotographic photosensitive members are used as image bearing members in electrophotographic printers and multifunction peripherals. An electrophotographic photosensitive member for example includes a conductive substrate and a photosensitive layer located either directly or indirectly on the conductive substrate. An electrophotographic photosensitive member in which one layer implements a charge transport function by mainly containing a charge transport material and another layer implements a charge generation function by mainly containing a charge generating material is referred to as a multi-layer electrophotographic photosensitive member. An electrophotographic photosensitive member in which one layer includes both a charge transport material and a charge generating material, and thus in which the one layer implements both a charge transport function and a charge generation function, is referred to as a single-layer electrophotographic photosensitive member.

One known example of a charge transport material that can be contained in an electrophotographic photosensitive member is a tris(4-styrylphenyl)amine derivative.

SUMMARY

A triarylamine derivative according to the present disclosure is represented by general formula (I).

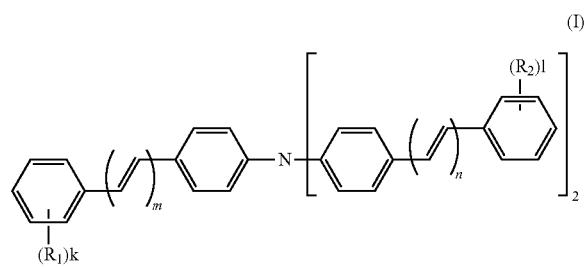

In general formula (I), $R_1$ and $R_2$ each represent, independently of one another, a chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12. In general formula (I), k and l each represent, independently of one another, an integer of at least 0 and no greater than 4. When k represents an integer greater than 1, chemical groups $R_1$ bonded to the same aromatic ring may be the same or different to one another. When l represents an integer greater than 1, chemical groups $R_2$ bonded to the same aromatic ring may be the same or different to one another. In general formula (I), m and n each represent, independently of one another, an integer of at least 1 and no greater than 3. Also, m and n represent different integers to one another.

An electrophotographic photosensitive member according to the present disclosure includes a photosensitive layer containing a charge generating material and a hole transport material. The photosensitive layer is either a multi-layer type photosensitive layer or a single-layer type photosensitive layer. The multi-layer type photosensitive layer includes a charge generating layer that contains the charge generating material and a charge transport layer that includes the hole transport material. The charge transport layer is located on the charge generating layer. The single-layer type photosensitive layer contains the charge generating material and the hole transport material. The hole transport material is the triarylamine derivative described above.

An image forming apparatus according to the present disclosure includes an image bearing member, a charging section, a light exposure section, a developing section, and a transfer section. The charging section charges a surface of the image bearing member. The light exposure section forms an electrostatic latent image on the surface of the image bearing member by exposing the surface of the image bearing member to light while in a charged state. The developing section develops the electrostatic latent image into a toner image. The transfer section transfers the toner image onto a transfer target from the image bearing member. The image bearing member is the electrophotographic photosensitive member described above.

DETAILED DESCRIPTION

Figure 1:
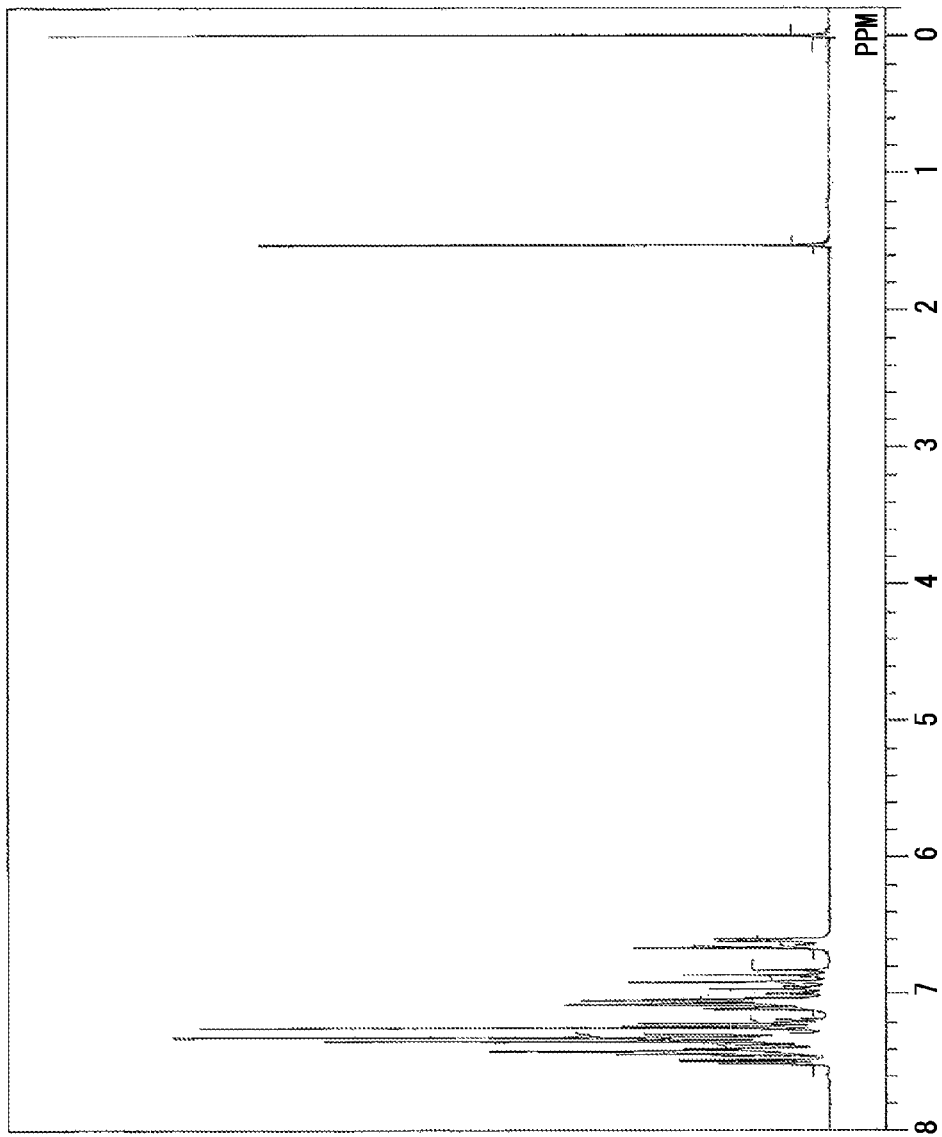
FIG. 1 is a $^1$H-NMR spectrum of a triarylamine derivative represented by chemical formula (HT-2).

The following explains embodiments of the present disclosure in detail, but the present disclosure is not in any way limited by the embodiments described below and appropriate variations may be made in practice within the intended scope of the present disclosure. Although explanation is omitted in some places in order to avoid repetition, such omission does not limit the essence of the present disclosure.

In the present description, the term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof.

<First Embodiment: Triarylamine Derivative>

A first embodiment of the present disclosure is a triarylamine derivative. The triarylamine derivative according to the present embodiment is represented by general formula (I) shown below.

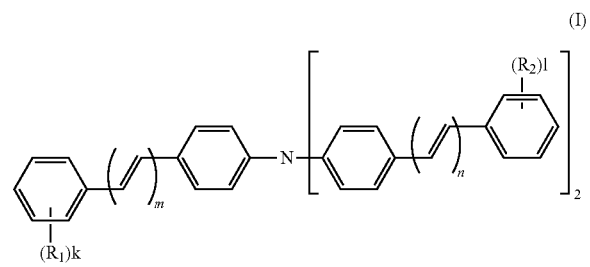

(I)

In general formula (I), $R_1$ and $R_2$ each represent, independently of one another, a chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12. In general formula (I), k and l each represent, independently of one another, an integer of at least 0 and no greater than 4. When k represents an integer greater than 1, chemical groups $R_1$ bonded to the same aromatic ring may be the same or different to one another. When l represents an integer greater than 1, chemical groups $R_2$ bonded to the same aromatic ring may be the same or different to one another. In general formula (I), m and n each represent, independently of one another, an integer of at least 1 and no greater than 3. Also, m and n represent different integers to one another.

In the triarylamine derivative represented by general formula (I) (also referred to below as triarylamine derivative (I)), m and n represent different integers to one another. In other words, among the three substituents of the triarylamine, one of the substituents has a different structure to the other two substituents. The triarylamine derivative (I) having an asymmetrical structure such as described above tends to have either or both of excellent solvent solubility and excellent binder resin compatibility. Therefore, crystallization of the triarylamine derivative (I) in a photosensitive layer during formation of the photosensitive layer can be inhibited. As a result, excellent external appearance of an electrophotographic photosensitive member (i.e., inhibition of crystallization in the photosensitive layer) can be maintained.

The triarylamine derivative (I) tends to have either or both excellent solvent solubility and binder resin compatibility as described above. Therefore, it tends to be easy to uniformly disperse the triarylamine derivative in the photosensitive layer. A photosensitive layer having the triarylamine derivative dispersed uniformly therein tends to have excellent electrical properties (in particular, restriction of residual potential). It is thought that through the above, an electrophotographic photosensitive member having excellent sensitivity properties can be effectively obtained.

Examples of halogen atoms that may be represented by $R_1$ and $R_2$ in general formula (I) include fluorine (fluoro group), chlorine (chloro group), and bromine (bromo group).

Examples of alkyl groups having a carbon number of at least 1 and no greater than 6 that may be represented by $R_1$ and $R_2$ in general formula (I) include a methyl group, an ethyl group, a propyl group, an isopropyl group, an n-butyl group, an s-butyl group, a t-butyl group, a pentyl group, an isopentyl group, a neopentyl group, and a hexyl group. Among alkyl groups having a carbon number of at least 1 and no greater than 6, alkyl groups having a carbon number of least 1 and no greater than 3 are preferable, with a methyl group being particularly preferable.

Examples of alkoxy groups having a carbon number of at least 1 and no greater than 6 that may be represented by $R_1$ and $R_2$ in general formula (I) include a methoxy group, an ethoxy group, an n-propoxy group, an isopropoxy group, an n-butoxy group, an s-butoxy group, a t-butoxy group, a pentyloxy group, an isopentyloxy group, a neopentyloxy group, and a hexyloxy group. Among alkoxy groups having a carbon number of at least 1 and no greater than 6, alkoxy groups having a carbon number of at least 1 and no greater than 3 are preferable, with a methoxy group being particularly preferable.

Examples of aryl groups having a carbon number of at least 6 and no greater than 12 that may be represented by $R_1$ and $R_2$ in general formula (I) include a phenyl group and a naphthyl group. Aryl groups having a carbon number of at least 6 and no greater than 12 that may be represented by $R_1$ and $R_2$ in general formula (I), may have a substituent such as described below. Examples of substituted aryl groups having a carbon number of at least 6 and no greater than 12 include aryl groups having a carbon number of at least 6 and no greater than 12 that have at least one and no greater than three alkyl groups that each have a carbon number of at least 1 and no greater than 6. Specific examples of such aryl groups include a tolyl group, a xylyl group, and a mesityl group.

The alkyl groups having a carbon number of at least 1 and no greater than 6 and the alkoxy groups having a carbon number of at least 1 and no greater than 6 that are described above may be optionally substituted. No particular limitations are placed on possible substituents which may, for example, be an alkoxy group having a carbon number of at least 1 and no greater than 6 or an aryl group having a carbon number of at least 6 and no greater than 12. The aryl groups having a carbon number of at least 6 and no greater than 12 that may represented by $R_1$ and $R_2$ in general formula (I) may be optionally substituted. No particular limitations are placed on possible substituents which may, for example, be an alkyl group having a carbon number of at least 1 and no greater than 6, an alkoxy group having a carbon number of at least 1 and no greater than 6, or an aryl group having a carbon number of at least 6 and no greater than 12.

Examples of alkyl groups having a carbon number of at least 1 and no greater than 6 that may be substituents are the same as the examples given of alkyl groups having a carbon number of at least 1 and no greater than 6 that may be represented by $R_1$ and $R_2$ in general formula (I). Examples of alkoxy groups having a carbon number of at least 1 and no greater than 6 that may be substituents are the same as the examples given of alkoxy groups having a carbon number of at least 1 and no greater than 6 that may be represented by $R_1$ and $R_2$ in general formula (I). Examples of aryl groups having a carbon number of at least 6 and no greater than 12 that may be substituents are the same as the examples given of aryl groups having a carbon number of at least 6 and no greater than 12 that may be represented by $R_1$ and $R_2$ in general formula (I).

In general formula (I), k and l each represent, independently of one another, an integer of at least 0 and no greater than 4.

When k represents an integer greater than 1, chemical groups $R_1$ bonded to the same aromatic ring may be the same or different to one another. In order to facilitate understanding, an example is explained in which k represents 2 and in which two chemical groups $R_1$ bonded to the same aromatic ring (phenyl group) are bonded to the phenyl group at an ortho position and a meta position. In such a situation, the ortho position $R_1$ and the meta position $R_1$ bonded to the same aromatic ring may be the same or different to one another.

When l represents an integer greater than 1, chemical groups $R_2$ bonded to the same aromatic ring may be the same or different to one another. In order to facilitate understanding, an example is explained in which l represents 2 and in which two chemical groups $R_2$ bonded to the same aromatic ring (phenyl group) are bonded to the phenyl group at an ortho position and a meta position. In such a situation, the ortho position $R_2$ and the meta position $R_2$ bonded to the same aromatic ring may be the same or different to one another. However, in the above situation, the ortho position $R_2$ is the same for each of the two aromatic rings in which $R_2$ is present. Also, in the above situation, the meta position $R_2$ is the same for each of the two aromatic rings in which $R_2$ is present.

In order to improve solvent solubility, $R_1$ in general formula (I) preferably represents a chemical group selected from the group consisting of an alkyl group having a carbon number of at least 1 and no greater than 6 and an alkoxy group having a carbon number of at least 1 and no greater than 6. $R_2$ preferably represents an alkoxy group having a carbon number of at least 1 and no greater than 6 for the same reason as explained above.

In order to increase π-electron conjugation of the overall molecule, k and l in general formula (I) preferably each represent 0 or 1. More preferably, l represents 0.

In general formula (I), k, l, m, and n preferably have the following relationships. When k and l each represent 0:m represents 1 and n represents 2 or 3; or m represents 2 or 3 and n represents 1. When at least one of k and l represents an integer greater than 0, m and n each represent an integer of at least 1 and no greater than 3, and m and n represent different integers to one another.

In general formula (I), k, l, m, and n more preferably have the following relationships. When k and l each represent 0, m represents 1 and n represents 2 or 3. When at least one of k and l represents an integer greater than 0, m and n each represent an integer of at least 1 and no greater than 3, and m and n represent different integers to one another.

In general formula (I), k, l, m, and n particularly preferably have the following relationships. Namely, k represents 0 or 1 and l represents 0. When k represents 0, m represents 1 and n represents 3. When k represents 1, n represents a larger integer than m.

In general formula (I), k, l, m, and n preferably have the relationships described above. Through such a configuration, even in a situation in which the benzene rings included in the substituents of the triarylamine have no substituents themselves (in other words, when k and l each represent 0), it is possible to have a significantly different bond structures present between the phenyl groups included in the triarylamine and the benzene rings included in the corresponding substituents of the triarylamine. Structural asymmetry of the triarylamine derivative (I) is increased as a result, which is thought to lead to either or both of improved solvent solubility and binder resin compatibility of the triarylamine derivative (I). The triarylamine derivative (I) described above tends to be easily dispersed in a photosensitive layer in a uniform manner. A photosensitive layer having the triarylamine derivative dispersed uniformly therein tends to have excellent electrical properties (in particular, restriction of residual potential) and, as result, can be used to obtain an electrophotographic photosensitive member having excellent sensitivity properties. Also, the triarylamine derivative (I) described above has a low tendency to crystallize in the photosensitive layer during formation of the photosensitive layer. As a result, excellent external appearance of the electrophotographic photosensitive member (i.e., inhibition of crystallization in the photosensitive layer) can be maintained.

Specific examples of the triarylamine derivative (I) include triarylamine derivatives represented by chemical formulae (HT-1) to (HT-10) shown below. The triarylamine derivatives represented by chemical formulae (HT-1) to (HT-10) shown below may be respectively referred to as triarylamine derivatives (HT-1) to (HT-10).

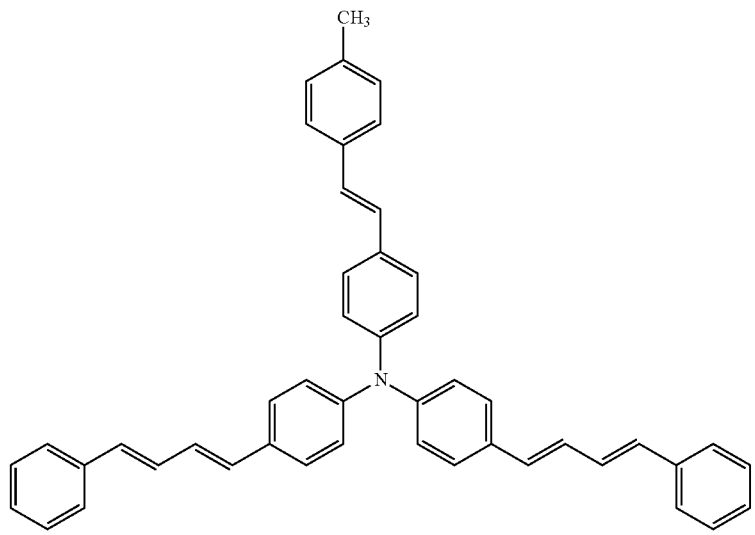

(HT-1)

(HT-2)
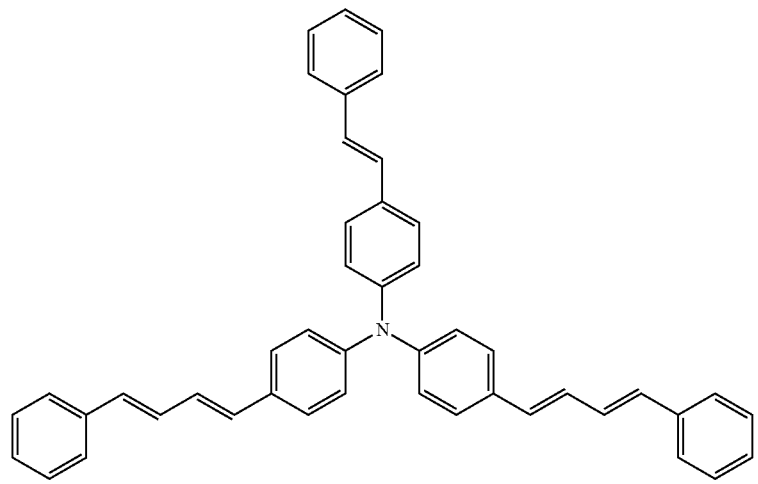
(HT-3)
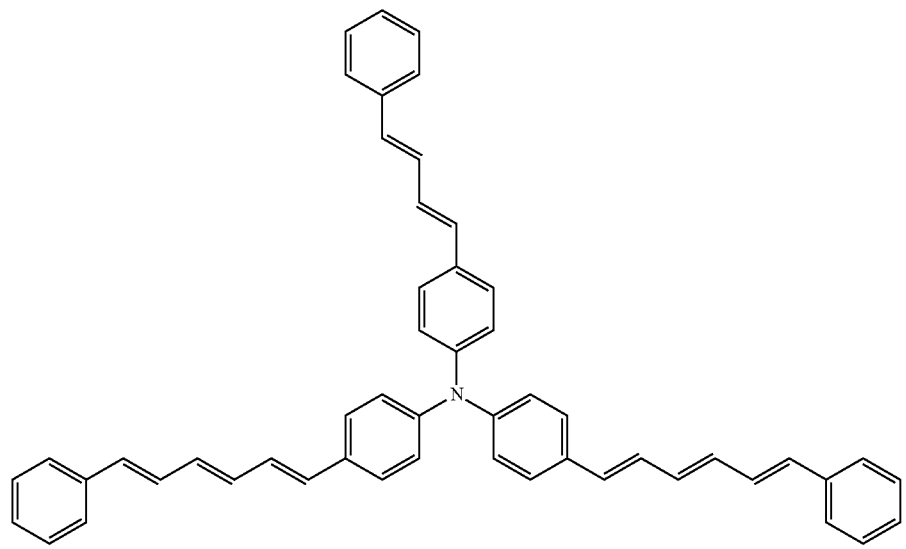
(HT-4)
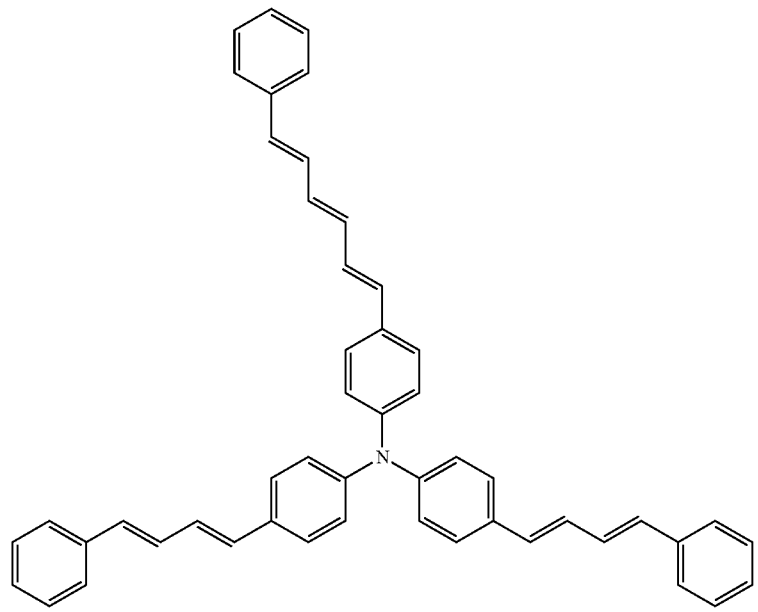

(HT-5)
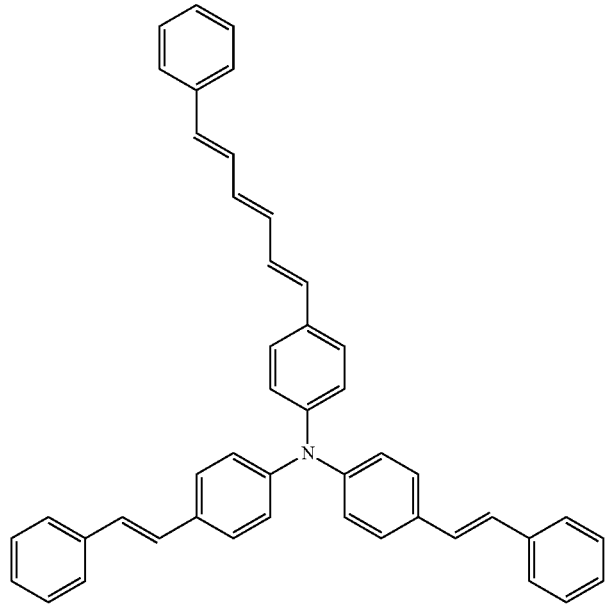
(HT-6)
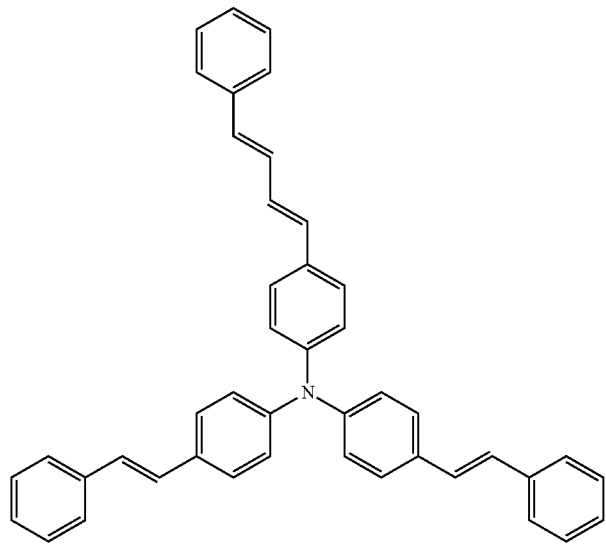
(HT-7)
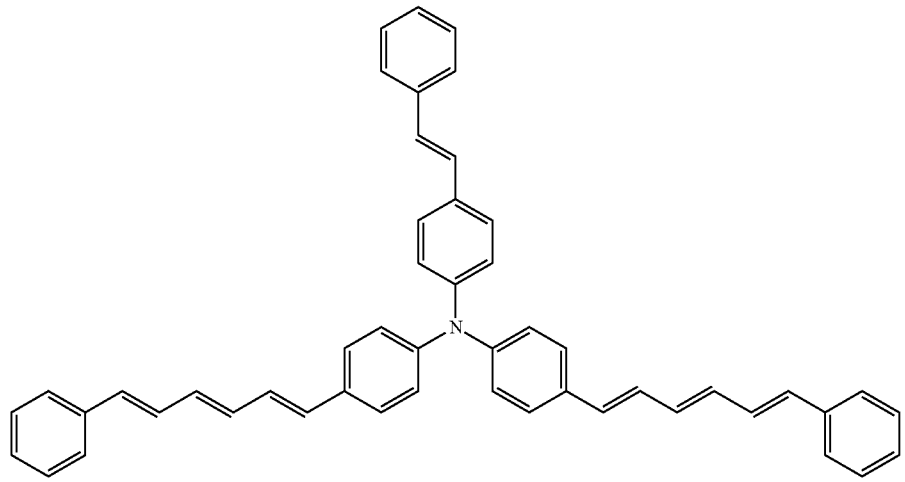

(HT-8)
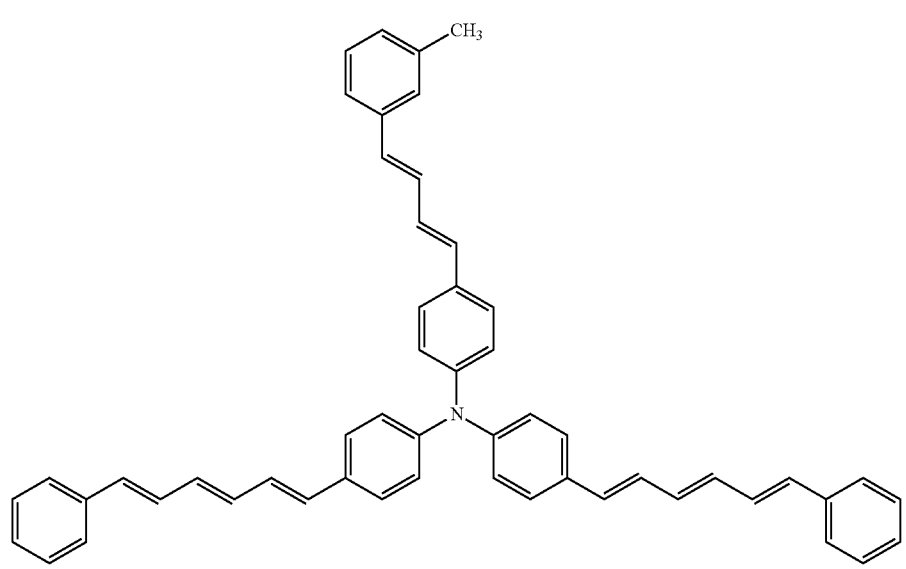
(HT-9)
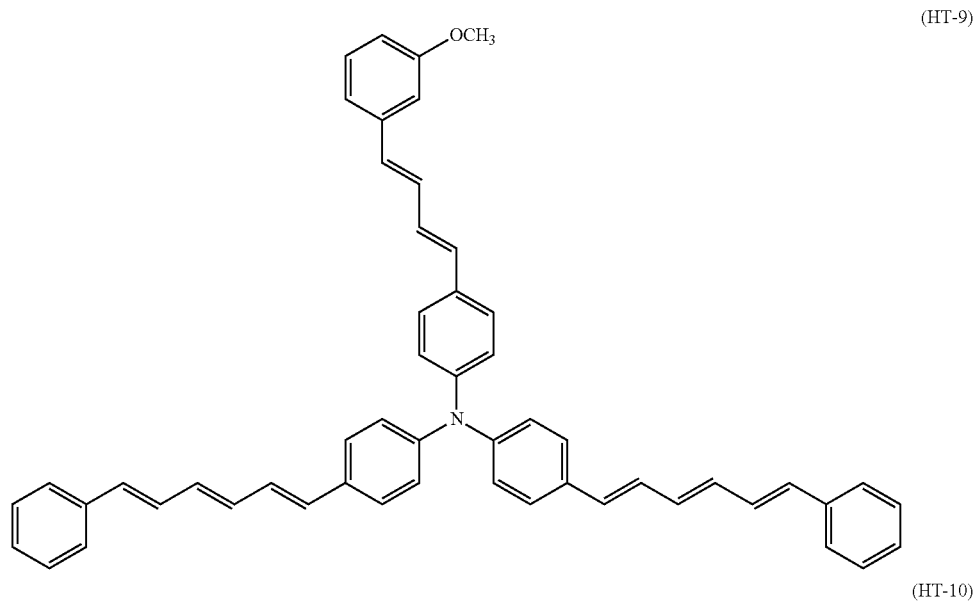
(HT-10)
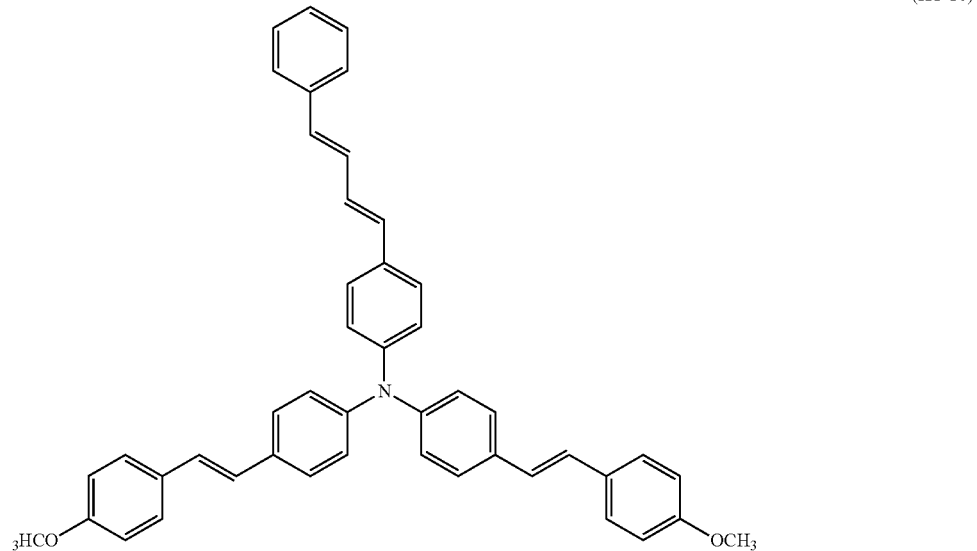

FIG. 1 illustrates a $^1$H-NMR spectrum of the triarylamine derivative (HT-2).

The triarylamine derivative (I) can be produced as shown below in reaction formulae (R-1) to (R-7) or through a method in accordance with the aforementioned reaction formulae. In addition to the reactions represented by reaction formulae (R-1) to (R-7), other processes may be carried out as appropriate depending on necessity thereof. The following explains the reactions represented by reaction formulae (R-1) to (R-7) in detail.

hand, if the number of moles of triethyl phosphite is too large relative to the number of moles of the benzene derivative (1-1), purification of the phosphonate derivative (3-1) after the reaction may be difficult due to an excessively large amount of triethyl phosphite remaining unreacted.

The reaction of the benzene derivative (1-1) and triethyl phosphite preferably has a reaction temperature of at least 160° C. and no greater than 200° C., and preferably has a reaction time of at least 2 hours and no greater than 10 hours.

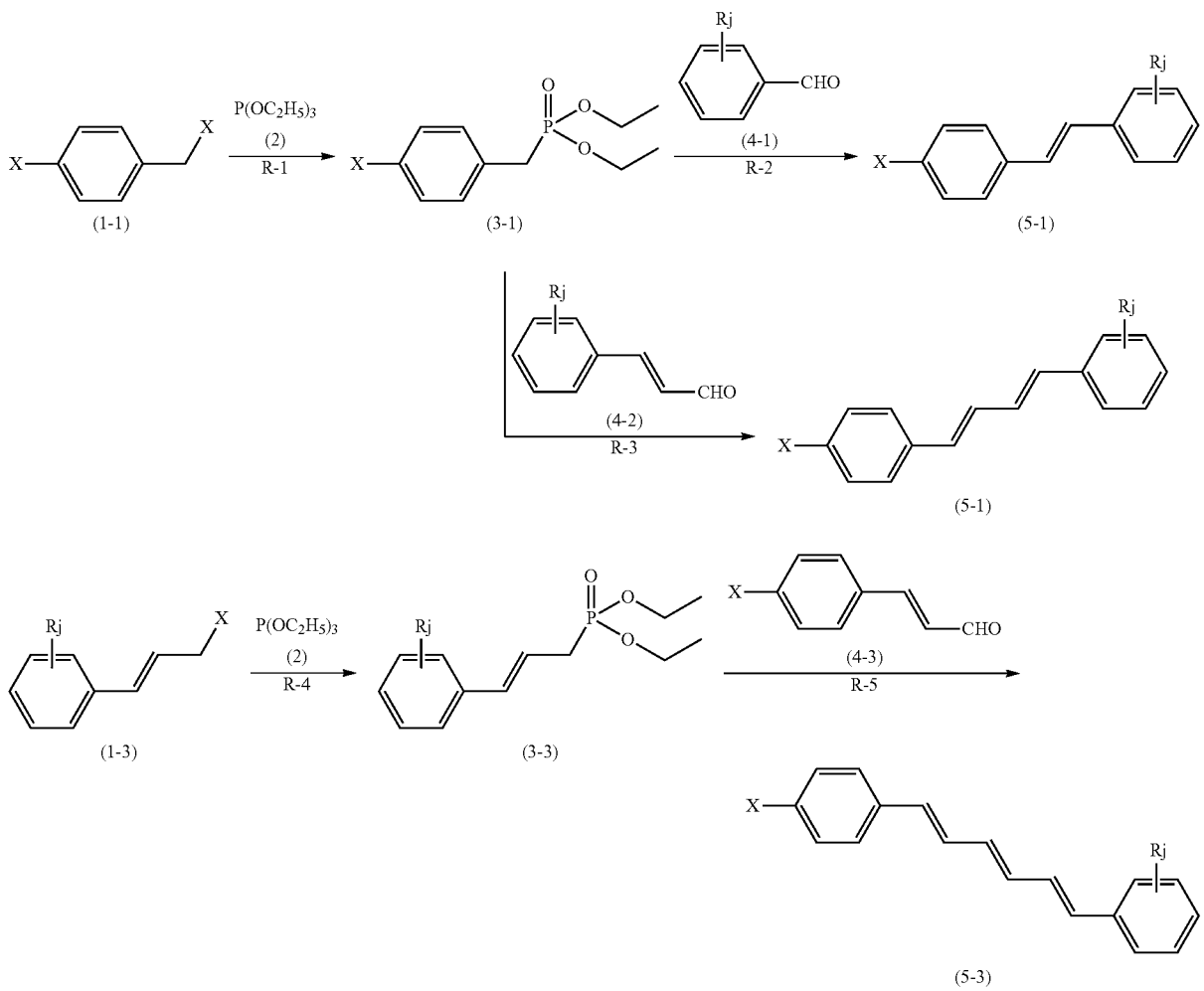

In the reaction formulae (R-1) to (R-5), R represents the same as $R_1$ or $R_2$ in general formula (I). Also, j represents the same meaning as k or l in general formula (I). X represents a halogen atom.

[Reaction Formula (R-1)]

In reaction formula (R-1), a benzene derivative (1-1) is caused to react with a compound (2)—that is, triethyl phosphite—to yield a phosphonate derivative (3-1).

A reaction ratio (benzene derivative (1-1):triethyl phosphite) of the benzene derivative (1-1) relative to triethyl phosphite (i.e., compound (2)) is preferably a molar ratio of 1:1 to 1:2.5. If the number of moles of triethyl phosphite is too small relative to the number of moles of the benzene derivative (1-1), the percentage yield of the phosphonate derivative (3-1) may be excessively reduced. On the other

[Reaction Formula (R-2)]

In reaction formula (R-2), the phosphonate derivative (3-1) is caused to react (Wittig reaction) with a benzaldehyde derivative (4-1) to yield a diphenyl ethene derivative (5-1).

A reaction ratio (phosphonate derivative (3-1):benzaldehyde derivative (4-1)) of the phosphonate derivative (3-1) relative to the benzaldehyde derivative (4-1) is preferably a molar ratio of 1:1 to 1:2.5. If the number of moles of the benzaldehyde derivative (4-1) is too small relative to the number of moles of the phosphonate derivative (3-1), the percentage yield of the diphenyl ethene derivative (5-1) may be excessively reduced. If the number of moles of the benzaldehyde derivative (4-1) is too large relative to the number of moles of the phosphonate derivative (3-1), purification of the diphenyl ethene derivative (5-1) may be difficult due to an excessively large amount of the benzaldehyde derivative (4-1) remaining unreacted.

The Wittig reaction may be carried out in the presence of a base. Examples of bases that may be used include sodium alkoxides (specifically, sodium methoxide and sodium ethoxide), metal hydrides (specifically, sodium hydride and potassium hydride), and metal salts (specifically, n-butyl lithium). Any one of the bases listed above may be used or a combination of any two or more of the bases listed above may be used.

The additive amount of a base such as described above is preferably at least 1 mol and no greater than 2 mol relative to 1 mol of the benzaldehyde derivative (4-1). If the additive amount of the base is too small, there may be a significant reduction in reactivity. On the other hand, if the additive amount of the base is too large, the reaction may be difficult to control.

The reaction represented by reaction formula (R-2) may be carried out in a solvent. Examples of solvents that may be used include ethers (specifically, tetrahydrofuran, diethyl ether, and dioxane), halogenated hydrocarbons (specifically, methylene chloride, chloroform, and dichloroethane), and aromatic hydrocarbons (specifically, benzene and toluene).

The reaction of the phosphonate derivative (3-1) and the benzaldehyde derivative (4-1) preferably has a reaction temperature of at least 0° C. and no greater than 50° C., and preferably has a reaction time of at least 2 hours and no greater than 24 hours.

[Reaction Formula (R-3)]

In reaction formula (R-3), the phosphonate derivative (3-1) is caused to react (Wittig reaction) with a cinnamaldehyde derivative (4-2) to yield a diphenyl butadiene derivative (5-2).

A reaction ratio (phosphonate derivative (3-1):cinnamaldehyde derivative (4-2)) of the phosphonate derivative (3-1) relative to the cinnamaldehyde derivative (4-2) is preferably a molar ratio of 1:1 to 1:2.5. If the number of moles of the cinnamaldehyde derivative (4-2) is too small relative to the number of moles of the phosphonate derivative (3-1), the percentage yield of the diphenyl butadiene derivative (5-2) may be excessively reduced. If the number of moles of the cinnamaldehyde derivative (4-2) is too large relative to the number of moles of the phosphonate derivative (3-1), purification of the diphenyl butadiene derivative (5-2) may be difficult due to an excessively large amount of the cinnamaldehyde derivative (4-2) remaining unreacted The Wittig reaction may be carried out in the presence of a base. Examples of bases that may be used are the same as the examples given for the reaction represented by reaction formula (R-2). Any one of the bases may be used or a combination of any two or more of the bases may be used.

The additive amount of a base such as described above is preferably at least 1 mol and no greater than 2 mol relative to 1 mol of the cinnamaldehyde derivative (4-2). If the additive amount of the base is too small, there may be a significant reduction in reactivity. On the other hand, if the additive amount of the base is too large, the reaction may be difficult to control.

The reaction represented by reaction formula (R-3) may be carried out in a solvent. Examples of solvents that may be used are the same as the examples given for the reaction represented by reaction formula (R-2).

The reaction of the phosphonate derivative (3-1) and the cinnamaldehyde derivative (4-2) preferably has a reaction temperature of at least 0° C. and no greater than 50° C., and preferably has a reaction time of at least 2 hours and no greater than 24 hours.

[Reaction Formula (R-4)]

In reaction formula (R-4), a benzene derivative (1-3) is caused to react with the compound (2)—that is, triethyl phosphite—to yield a phosphonate derivative (3-3).

A reaction ratio (benzene derivative (1-3):triethyl phosphite) of the benzene derivative (1-3) relative to triethyl phosphite (i.e., compound (2)) is preferably a molar ratio of 1:1 to 1:2.5. If the number of moles of triethyl phosphite is too small relative to the number of moles of the benzene derivative (1-3), the percentage yield of the phosphonate derivative (3-3) may be excessively reduced. On the other hand, if the number of moles of triethyl phosphite is too large relative to the number of moles of the benzene derivative (1-3), purification of the phosphonate derivative (3-3) after the reaction may be difficult due to an excessively large amount of triethyl phosphite remaining unreacted.

The reaction of the benzene derivative (1-3) and triethyl phosphite preferably has a reaction temperature of at least 160° C. and no greater than 200° C., and preferably has a reaction time of at least 2 hours and no greater than 10 hours.

[Reaction Formula (R-5)]

In reaction formula (R-5), the phosphonate derivative (3-3) is caused to react (Wittig reaction) with a cinnamaldehyde derivative (4-3) to yield a diphenyl hexatriene derivative (5-3).

A reaction ratio (phosphonate derivative (3-3):cinnamaldehyde derivative (4-3) of the phosphonate derivative (3-3) relative to the cinnamaldehyde derivative (4-3) is preferably a molar ratio of 1:1 to 1:2.5. If the number of moles of the cinnamaldehyde derivative (4-3) is too small relative to the number of moles of the phosphonate derivative (3-3), the percentage yield of the diphenyl hexatriene derivative (5-3) may be excessively reduced. If the number of moles of the cinnamaldehyde derivative (4-3) is too large relative to the number of moles of the phosphonate derivative (3-3), purification of the diphenyl hexatriene derivative (5-3) may be difficult due to an excessively large amount of the cinnamaldehyde derivative (4-3) remaining unreacted.

The Wittig reaction may be carried out in the presence of a base. Examples of bases that may be used are the same as the examples given for the reaction represented by reaction formula (R-2). Any one of the bases may be used or a combination of any two or more of the bases may be used.

The additive amount of a base such as described above is preferably at least 1 mol and no greater than 2 mol relative to 1 mol of the cinnamaldehyde derivative (4-3). If the additive amount of the base is too small, there may be a significant reduction in reactivity. On the other hand, if the additive amount of the base is too large, the reaction may be difficult to control.

The reaction represented by reaction formula (R-5) may be carried out in a solvent. Examples of solvents that may be used are the same as the examples given for the reaction represented by reaction formula (R-2).

The reaction of the phosphonate derivative (3-3) and the cinnamaldehyde derivative (4-3) preferably has a reaction temperature of at least 0° C. and no greater than 50° C., and preferably has a reaction time of at least 2 hours and no greater than 24 hours.

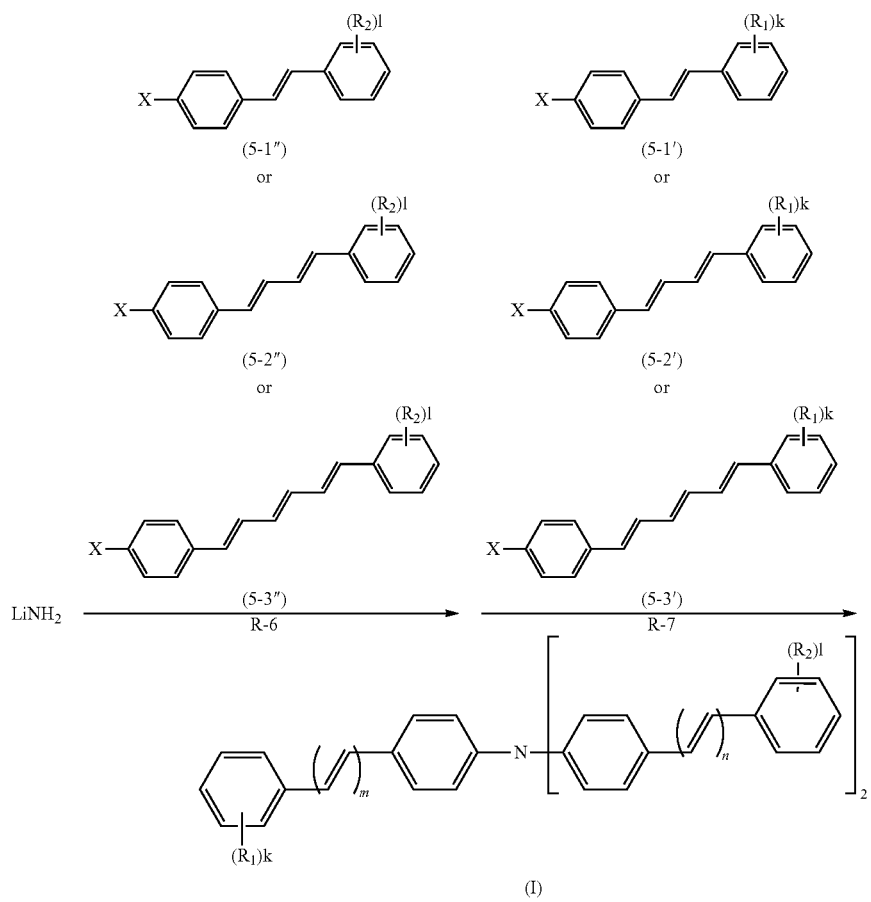

In reaction formulae (R-6) and (R-7), $R_1$, $R_2$, k, l, m, and n represent the same as $R_1$, $R_2$, k, l, m, and n in general formula (I). X represents a halogen atom.

[Reaction Formula (R-6)]

In reaction formula (R-6), a diphenyl ethene derivative (5-1"), a diphenyl butadiene derivative (5-2"), or a diphenyl hexatriene derivative (5-3") is caused to react (coupling reaction) with lithium amide to produce an intermediate compound. The diphenyl ethene derivative (5-1") is equivalent to the diphenylethene derivative (5-1) produced in the reactions described above in a situation in which R and j represent the same as $R_2$ and l in general formula (I). The diphenyl butadiene derivative (5-2") is equivalent to the diphenyl butadiene derivative (5-2) produced in the reactions described above in a situation in which R and j represent the same as $R_2$ and l in general formula (I). The diphenyl hexatriene derivative (5-3") is equivalent to the diphenyl hexatriene derivative (5-3) produced in the reactions described above in a situation in which R and j represent the same as $R_2$ and l in general formula (I).

A reaction ratio (derivative (5-1"), (5-2"), or (5-3"): lithium amide) of the diphenyl ethene derivative (5-1"), the diphenyl butadiene derivative (5-2"), or the diphenyl hexatriene derivative (5-3") relative to lithium amide is preferably a molar ratio of 5:1 to 1:1.

If the number of moles of lithium amide is too small relative to the number of moles of the derivative (5-1"), (5-2"), or (5-3"), the percentage yield of the intermediate compound may be excessively reduced. On the other hand, if the number of moles of lithium amide is too large relative to the number of moles of the derivative (5-1"), (5-2"), or (5-3"), purification of the intermediate compound after reaction may be difficult due to an excessively large amount of lithium amide remaining unreacted.

The reaction represented by reaction formula (R-6) preferably has a reaction temperature of at least 80° C. and no greater than 140° C., and preferably has a reaction time of at least 2 hours and no greater than 10 hours.

A palladium compound is preferably used as a catalyst in the reaction represented by reaction formula (R-6). By using a palladium compound as a catalyst, the activation energy of the reaction represented by reaction formula (R-6) can be lowered. As a result, the percentage yield of the intermediate compound can be improved.

Examples of palladium compounds that may be used include tetravalent palladium compounds, divalent palladium compounds, and other palladium compounds. Specific examples of tetravalent palladium compounds include hexachloro palladium(IV) sodium tetrahydrate and hexachloro palladium(IV) potassium tetrahydrate. Specific examples of divalent palladium compounds include palladium(II) chloride, palladium(II) bromide, palladium(II) acetate, palladium(II) acetylacetate, dichlorobis(benzonitrile)palladium(II), dichlorobis(triphenylphosphine)palladium(II), dichlorotetramine palladium(II), and dichloro(cycloocta-1,5-diene)palladium(II). Specific examples of other palladium compounds include tris(dibenzylideneacetone)dipalladium(0), tris(dibenzylideneacetone)dipalladium(0) chloroform complex, and tetrakis(triphenylphosphine)palladium(0). Any one of the palladium compounds listed above may be used or a combination of any two or more of the palladium compounds listed above may be used.

The additive amount of the palladium compound is preferably at least 0.0005 mol and no greater than 20 mol relative to 1 mol of the derivative (5-1"), (5-2"), or (5-3"), and more preferably at least 0.001 mol and no greater than 1 mol.

A palladium compound such as described above may have a structure including a ligand. As a result, reactivity of the reaction represented by reaction formula (R-6) can be improved. Examples of ligands that may be used include tricyclohexylphosphine, triphenylphosphine, methyldiphenylphosphine, trifurylphosphine, tri(o-tolyl)phosphine, dicyclohexylphenylphosphine, tri(t-butyl)phosphine, 2,2'-bis(diphenylphosphino)-1,1'-binaphthyl, and 2,2'-bis[(diphenylphosphino)diphenyl]ether. Any one of the ligands listed above may be used or a combination of any two or more of the ligands listed above may be used. The additive amount of the ligand is preferably at least 0.0005 mol and no greater than 20 mol relative to 1 mol of the derivative (5-1"), (5-2"), or (5-3"), and more preferably at least 0.001 mol and no greater than 1 mol.

The reaction represented by reaction formula (R-6) is preferably carried out in the presence of a base. Through the presence of the base, hydrogen halide produced during the reaction can be quickly neutralized and catalytic activity can be improved. As a result, the percentage yield of the intermediate compound can be improved.

The base may be an inorganic base or an organic base. Preferable organic bases for example include alkali metal alkoxides (specifically, sodium methoxide, sodium ethoxide, potassium methoxide, potassium ethoxide, lithium tert-butoxide, sodium tert-butoxide, and potassium tert-butoxide), with sodium tert-butoxide being particularly preferable. Preferable inorganic bases include tripotassium phosphate and cesium fluoride.

In a situation in which at least 0.0005 mol and no greater than 20 mol of the palladium compound is added relative to 1 mol of the derivative (5-1"), (5-2"), or (5-3"), the additive amount of the base is preferably at least 1 mol and no greater than 50 mol, and more preferably at least 1 mol and no greater than 30 mol.

The reaction represented by reaction formula (R-6) may be carried out in a solvent. Examples of solvents that may be used include xylene (specifically, o-xylene), toluene, tetrahydrofuran, and dimethyl formamide.

[Reaction Formula (R-7)]

In reaction formula (R-7), a diphenyl ethene derivative (5-1'), a diphenyl butadiene derivative (5-2'), or a diphenyl hexatriene derivative (5-3') is caused to react (coupling reaction) with the resultant intermediate compound to produce a target compound—that is, the triarylamine derivative (I). The diphenyl ethene derivative (5-1') is equivalent to the diphenyl ethene derivative (5-1) produced in the reactions described above in a situation in which R and j represent the same as $R_1$ and k in general formula (I). The diphenyl butadiene derivative (5-2') is equivalent to the diphenyl butadiene derivative (5-2) produced in the reactions described above in a situation in which R and j represent the same as $R_1$ and k in general formula (I). The diphenyl hexatriene derivative (5-3') is equivalent to the diphenyl hexatriene derivative (5-3) produced in the reactions described above in a situation in which R and j represent the same as $R_1$ and k in general formula (I).

A reaction ratio (derivative (5-1'), (5-2'), or (5-3'):intermediate compound) of the diphenyl ethene derivative (5-1'), the diphenyl butadiene derivative (5-2'), or the diphenyl hexatriene derivative (5-3') relative to the intermediate compound is preferably a molar ratio of 5:1 to 1:1.

If the number of moles of the intermediate compound is too small relative to the number of moles of the derivative (5-1'), (5-2'), or (5-3'), the percentage yield of the triarylamine derivative (I) may be excessively reduced. On the other hand, if the number of moles of the intermediate compound is too large relative to the number of moles of the derivative (5-1'), (5-2'), or (5-3'), purification of the triarylamine derivative (I) after the reaction may be difficult due to an excessively large amount of the intermediate compound remaining unreacted.

The reaction represented by reaction formula (R-7) preferably has a reaction temperature of at least 80° C. and no greater than 140° C., and preferably has a reaction time of at least 2 hours and no greater than 10 hours.

A palladium compound is preferably used as a catalyst in the reaction represented by reaction formula (R-7). By using a palladium compound as a catalyst, the activation energy of the reaction represented by reaction formula (R-7) can be lowered. As a result, the percentage yield of the triarylamine derivative (I) can be improved.

Examples of palladium compounds that may be used are the same as the examples given for the reaction represented by reaction formula (R-6). Any one of the palladium compounds may be used or a combination of any two or more of the palladium compounds may be used.

The additive amount of the palladium compound is preferably at least 0.0005 mol and no greater than 20 mol relative to 1 mol of the derivative (5-1'), (5-2'), or (5-3'), and more preferably at least 0.001 mol and no greater than 1 mol.

A palladium compound such as described above may have a structure including a ligand. As a result, reactivity of the reaction represented by reaction formula (R-7) can be improved. Examples of ligands that may be used are the same as the examples given for the reaction represented by reaction formula (R-6). Any one of the ligands may be used or a combination of any two or more of the ligands may be used. The additive amount of the ligand is preferably at least 0.0005 mol and no greater than 20 mol relative to 1 mol of the derivative (5-1'), (5-2'), or (5-3'), and more preferably at least 0.001 mol and no greater than 1 mol.

The reaction represented by reaction formula (R-7) is preferably carried out in the presence of a base. Through the presence of the base, hydrogen halide produced during the reaction can be quickly neutralized and catalytic activity can be improved. As a result, the percentage yield of the triarylamine derivative (I) can be improved.

The base may be an inorganic base or an organic base. Examples of organic bases and inorganic bases that may be used are the same as the examples given for the reaction represented by reaction formula (R-6).

In a situation in which at least 0.0005 mol and no greater than 20 mol of the palladium compound is added relative to 1 mol of the derivative (5-1'), (5-2'), or (5-3'), the additive amount of the base is preferably at least 1 mol and no greater than 10 mol, and more preferably at least 1 mol and no greater than 5 mol.

The reaction represented by reaction formula (R-7) may be carried out in a solvent. Examples of solvents that may be used are the same as the examples given for the reaction represented by reaction formula (R-6).

Through the above, an explanation of the triarylamine derivative according to the present embodiment has been provided. Through the triarylamine derivative according to the present embodiment, a photosensitive member having excellent electrical properties can be obtained while also maintaining excellent external appearance of the photosensitive member (i.e., inhibiting crystallization in the photosensitive layer).

<Second Embodiment: Electrophotographic Photosensitive Member>

A second embodiment of the present disclosure is an electrophotographic photosensitive member (also referred to below simply as a photosensitive member). The photosensitive member according to the present embodiment includes a photosensitive layer. The photosensitive layer is either a multi-layer type photosensitive layer or a single-layer type photosensitive layer.

<1. Single-Layer Photosensitive Member>

Figure 2A:
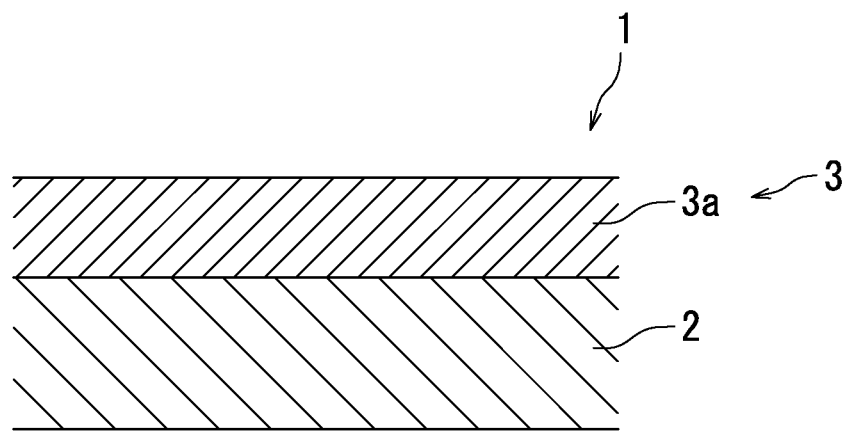
FIGS. 2A and 2B are each a rough cross-sectional illustration of an example of structure of an electrophotographic photosensitive member according to an embodiment of the present disclosure.
Figure 2B:
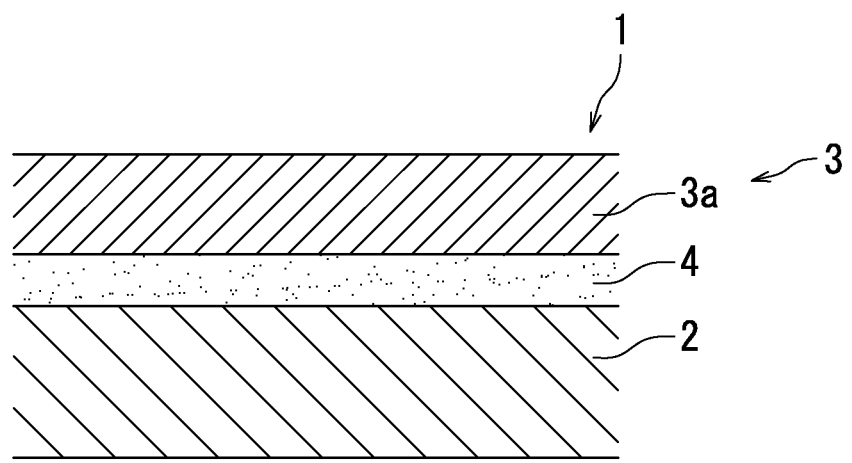

The following explains, with reference to FIGS. 2A and 2B, a configuration in which a photosensitive member 1 according to the present embodiment includes a photosensitive layer 3 that is a single-layer type photosensitive layer 3a. In other words, the following explains a configuration in which the photosensitive member 1 according to the present embodiment is a single-layer photosensitive member. Each of FIGS. 2A and 2B is a rough cross-sectional illustration of an example (single-layer photosensitive member) of structure of the photosensitive member according to the present embodiment.

As illustrated in FIG. 2A, in a configuration in which the photosensitive member 1 is a single-layer photosensitive member, the photosensitive layer 3 included in the photosensitive member 1 is the single-layer type photosensitive layer 3a. The single-layer type photosensitive layer 3a is located on a conductive substrate 2. The single-layer type photosensitive layer 3a contains a charge generating material and a hole transport material. The single-layer type photosensitive layer 3a may optionally contain an electron transport material, a binder resin, and various additives depending on necessity thereof.

No particular limitations are placed on the photosensitive member 1 in a configuration in which the photosensitive member 1 is a single-layer photosensitive member, other than the photosensitive member 1 including the single-layer type photosensitive layer 3a. The single-layer type photosensitive layer 3a may for example be located directly on the conductive substrate 2 as illustrated in FIG. 2A. Alternatively, an intermediate layer 4 may be present between the conductive substrate 2 and the single-layer type photosensitive layer 3a.

No particular limitations are placed on thickness of the single-layer type photosensitive layer 3a, so long as the thickness thereof is sufficient to enable the single-layer type photosensitive layer 3a to function as a single-layer type photosensitive layer. The single-layer type photosensitive layer 3a preferably has a thickness of at least 5 µm and no greater than 100 µm, and more preferably at least 10 µm and no greater than 50 µm.

<2. Multi-Layer Photosensitive Member>

Figure 3A:
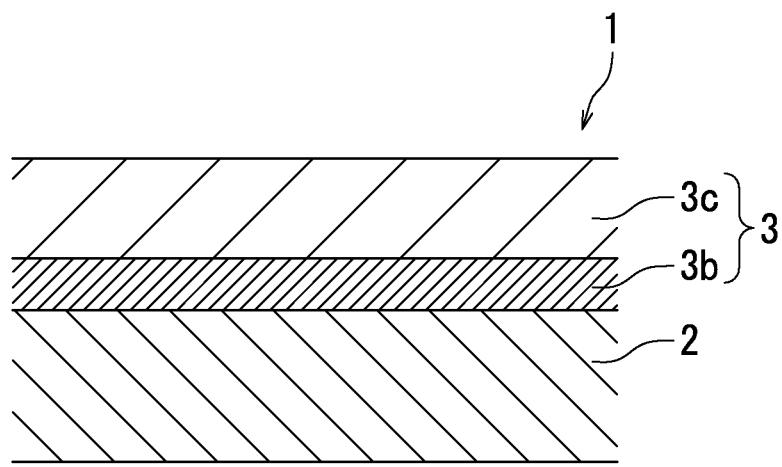
FIGS. 3A and 3B are each a rough cross-sectional illustration of another example of structure of an electrophotographic photosensitive member according to an embodiment of the present disclosure.
Figure 3B:
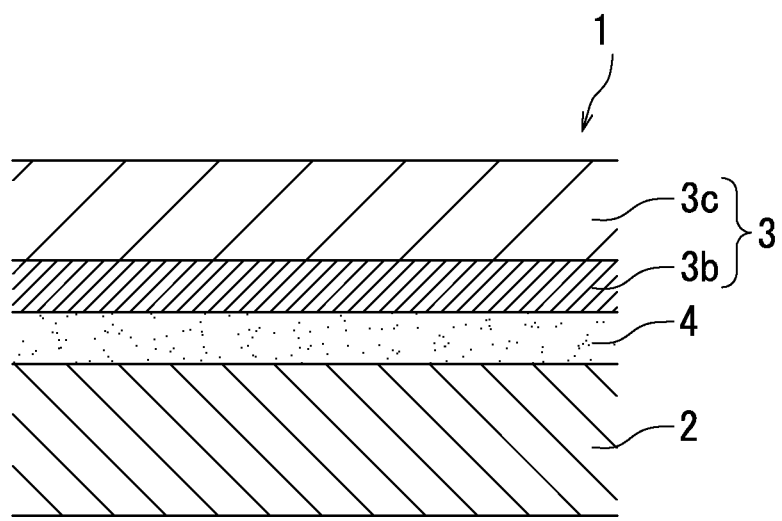

The following explains, with reference to FIGS. 3A and 3B, a configuration in which the photosensitive layer 3 of the photosensitive member 1 according to the present embodiment includes a charge generating layer 3b and a charge transport layer 3c. In other words, the following explains a configuration in which the photosensitive member 1 according to the present embodiment is a multi-layer photosensitive member. Each of FIGS. 3A and 3B is a rough cross-sectional illustration of an example (multi-layer photosensitive member) of structure of the photosensitive member 1 according to the present embodiment.

As illustrated in FIG. 3A, in a configuration in which the photosensitive member 1 is a multi-layer photosensitive member, the photosensitive member 1 includes the photosensitive layer 3 on the conductive substrate 2. The photosensitive layer 3 includes the charge generating layer 3b and the charge transport layer 3c. The charge generating layer 3b is located on the conductive substrate 2. The charge transport layer 3c is located on the charge generating layer 3b. As a result of the charge transport layer 3c being an outermost layer, abrasion resistance can be readily improved while also maintaining excellent electrical properties.

The charge generating layer 3b contains a charge generating material. The charge generating layer 3b may optionally contain a base resin and various additives depending on necessity thereof. The charge transport layer 3c contains a hole transport material. The charge transport layer 3c may optionally contain an electron acceptor compound, a binder resin, and various additives depending on necessity thereof.

No particular limitations are placed on the photosensitive member 1 in a configuration in which the photosensitive member 1 is a multi-layer photosensitive member, other than the photosensitive member 1 including the photosensitive layer 3 (charge generating layer 3b and charge transport layer 3c). An intermediate layer 4 may be present between the conductive substrate 2 and the photosensitive layer 3 as illustrated in FIG. 3B.

No particular limitations are placed on thickness of the charge generating layer 3b and the charge transport layer 3c, so long as the thicknesses thereof are sufficient to enable the charge generating layer 3b and the charge transport layer 3c to implement their respective functions. Specifically, the charge generating layer 3b preferably has a thickness of at least 0.01 µm and no greater than 5 µm, and more preferably at least 0.1 µm and no greater than 3 µm. Also, the charge transport layer 3c preferably has a thickness of at least 2 µm and no greater than 100 µm, and more preferably at least 5 µm and no greater than 50 µm.

In the photosensitive member 1 (single-layer photosensitive member or multi-layer photosensitive member), the photosensitive layer 3 is preferably an outermost layer in order to inhibit occurrence of image deletion and restrict production costs. Also, in a configuration in which the photosensitive member 1 is a multi-layer photosensitive member, the charge transport layer 3c of the photosensitive layer 3 is preferably an outermost layer.

Through the above, an explanation of structure of the photosensitive member 1 according to the present embodiment has been provided for a single-layer photosensitive member with reference to FIGS. 2A and 2B, and a multi-layer photosensitive member with reference to FIGS. 3A and 3B.

<3. Common Elements>

The following explains elements of configuration that are common to the photosensitive member for both the single-layer photosensitive member and the multi-layer photosensitive member.

<3-1. Conductive Substrate>

In the present embodiment, no particular limitations are placed on the conductive substrate other than at least a surface portion of the conductive substrate being conductive. More specifically, the conductive substrate may be formed from a conductive material. Alternatively, the conductive substrate may be formed through coating or vapor deposition of a conductive material on the surface of a plastic material or glass. Examples of conductive materials that may be used include metals such as aluminum, iron, copper, tin, platinum, silver, vanadium, molybdenum, chromium, cadmium, titanium, nickel, palladium, indium, stainless steel, and brass, and alloys of the aforementioned metals. Any one of the conductive materials listed above may be used or a combination of any two or more of the conductive materials listed above may be used.

Among the examples of conductive substrates described above, use of a conductive substrate containing aluminum or aluminum alloy is preferable. The reasoning for the above is that use of such a conductive substrate enables provision of a photosensitive member that tends to have good charge mobility from the photosensitive layer to the conductive substrate and that can be used to form images with better image quality.

No particular limitations are placed on the shape of the conductive substrate which may be selected as appropriate. The conductive substrate may for example be sheet-shaped or drum-shaped. The conductive substrate preferably has sufficient mechanical strength during use.

<3-2. Charge Generating Material>

No particular limitations are placed on the charge generating material other than being a charge generating material that can be used in photosensitive members. Examples of charge generating materials that may be used include phthalocyanine-based pigments, perylene pigments, bisazo pigments, dithioketopyrrolopyrrole pigments, metal-free naphthalocyanine pigments, metal naphthalocyanine pigments, squaraine pigments, tris-azo pigments, indigo pigments, azulenium pigments, cyanine pigments, powders of inorganic photoconductive materials (for example, selenium, selenium-tellurium, selenium-arsenic, cadmium sulfide, or amorphous silicon), pyrylium salts, anthanthrone-based pigments, triphenylmethane-based pigments, threne-based pigments, toluidine-based pigments, pyrazoline-based pigments, and quinacridone-based pigments.

Any one charge generating material or a combination of two or more charge generating materials that is absorptive with respect to light in a desired wavelength region may be used. For example, in a digital optical image forming apparatus (for example, a laser beam printer or facsimile machine that uses a light source such as a semiconductor laser), a photosensitive member that is sensitive to a region of wavelengths of at least 700 nm is preferably used. Therefore, a phthalocyanine-based pigment (for example, metal-free phthalocyanine or titanyl phthalocyanine (oxotitanium phathalocyanine)) is preferably used. No particular limitations are placed on the crystal structure of the phthalocyanine-based pigment, and phthalocyanine-based pigments having various different crystal structures may be used. The phthalocyanine-based pigment for example has an X-form crystal structure or a Y-form crystal structure. In order to improve electrical properties of the photosensitive member, the charge generating material is preferably metal-free phthalocyanine having an X-form crystal structure (also referred to below as X-form metal-free phthalocyanine) or titanyl phthalocyanine having a Y-form crystal structure (also referred to below as Y-form titanyl phthalocyanine).

A photosensitive member included in an image forming apparatus that uses a short-wavelength laser light source (for example, a laser light source having an approximate wavelength of at least 350 nm and no greater than 550 nm) preferably contains an anthanthrone-based pigment or a perylene-based pigment as a charge generating material.

The amount of the charge generating material in the multi-layer photosensitive member is preferably at least 5 parts by mass and no greater than 1,000 parts by mass relative to 100 parts by mass of a base resin contained in the charge generating layer, and more preferably at least 30 parts by mass and no greater than 500 parts by mass. Explanation of the base resin is provided further below.

The amount of the charge generating material in the single-layer photosensitive member is preferably at least 0.1 parts by mass and no greater than 50 parts by mass relative to 100 parts by mass of a binder resin contained in the single-layer type photosensitive layer, and more preferably at least 0.5 parts by mass and no greater than 30 parts by mass.

<3-3. Hole Transport Material>

In the present embodiment, the hole transport material contained in the photosensitive member is the triarylamine derivative (I) according to the first embodiment. Through inclusion of the triarylamine derivative (I) in the photosensitive layer of the photosensitive member, electrical properties can be improved while maintaining excellent external appearance of the photosensitive member (i.e., inhibiting crystallization in the photosensitive layer) for the same reasons as explained for the first embodiment.

Furthermore, through inclusion of the triarylamine derivative (I) in the photosensitive layer of the photosensitive member, occurrence of transfer memory can be inhibited. The following explains the reason that occurrence of transfer memory is thought to be inhibited. Transfer memory is first described in order to facilitate explanation.

When the photosensitive member is used to form an image, an image formation process is performed that for example includes the following steps 1-4.

1) Charging a surface of the photosensitive member

2) Forming an electrostatic latent image on the surface of the photosensitive member by exposing the surface to light while in a charged state 3) Developing the electrostatic latent image into a toner image while applying a developing bias voltage 4) Transferring the formed toner image from the photosensitive member to a transfer target However, in an image formation process such as described above, transfer memory caused by the transfer step may occur due to the fact that the photosensitive member rotates during use. The following provides a more specific explanation. In the charging step, the surface of the photosensitive member is uniformly charged to a specific potential (for example, positive polarity). After the light exposure step and the development step, a transfer bias of opposite polarity (for example, negative polarity) to the aforementioned charging is applied to the photosensitive member via the transfer target during the transfer step. The potential of a non-exposed region of the surface of the photosensitive member sometimes decreases significantly under the influence of the applied transfer bias. In contrast, the potential of an exposed region of the surface of the photosensitive member hardly decreases at all due to toner adhered to the photosensitive member. As a consequence of the decreased potential of the non-exposed region, a potential difference arises between the exposed region and the non-exposed region, and it may be difficult to charge the non-exposed region to a desired potential (for example, a desired potential of positive polarity) when attempting to uniformly charge the surface of the photosensitive member in a charging step during a next rotation of the photosensitive member. Therefore, a situation may arise in which the exposed region and the non-exposed region have different charging potentials. The above effect in which chargeability of the non-exposed region decreases is referred to as transfer memory. Transfer memory tends to be more noticeable in a process that does not include a static elimination step. During the next rotation of the photosensitive member, a region that cannot be charged to a desired potential during the charging step (specifically, a region of the surface of the photosensitive member corresponding to the non-exposed region during a previous rotation of the photosensitive member) has a lower potential (for example, potential of positive polarity) to other regions and, as a consequence, toner (for example, toner of positive polarity) is more strongly attracted toward the aforementioned region. An image defect such as an image ghost occurs as a result.

In the triarylamine derivative (I), m and n represent different integers to one another. In other words, among the three substituents of the triarylamine part, one of the substituents has a different structure to the other two substituents. The triarylamine derivative (I) having an asymmetrical structure such as described above tends to have either or both of excellent solvent solubility and excellent binder resin compatibility. Therefore, the triarylamine derivative (I) tends to be easily dispersed in a uniform manner in the photosensitive layer 3 as a hole transport material.

The photosensitive layer 3 in which the triarylamine derivative (I) is uniformly dispersed as the hole transport material tends to have excellent charge mobility. In the photosensitive member 1 including the photosensitive layer 3 described above, charge imparted during transfer bias application, which is of opposite polarity to charge imparted during charging, can be caused to move quickly. Therefore, the potential difference between a blank paper portion prior to transfer bias application and the blank paper portion during transfer bias application can be reduced. As a result, potential on the photosensitive member 1 can be stabilized and transfer memory can be inhibited from occurring. It is thought that the effect of inhibiting transfer memory described above is particularly effective in an image forming apparatus that includes a contact charging section that performs charging under harsher conditions for the photosensitive member 1 than a non-contact charging section.

Through the photosensitive member according to the present embodiment, in addition to improving electrical properties while maintaining excellent external appearance of the photosensitive member (i.e., inhibiting crystallization in the photosensitive layer), transfer memory can be effectively inhibited for the reason explained above.

The amount of the hole transport material in the multi-layer photosensitive member is preferably at least 10 parts by mass and no greater than 200 parts by mass relative to 100 parts by mass of a binder resin contained in the charge transport layer, and more preferably at least 20 parts by mass and no greater than 100 parts by mass.

The amount of the hole transport material in the single-layer photosensitive member is preferably at least 10 parts by mass and no greater than 200 parts by mass relative to 100 parts by mass of a binder resin contained in the single-layer type photosensitive layer, and more preferably at least 10 parts by mass and no greater than 100 parts by mass.

<3-4. Electron Transport Material and Electron Acceptor Compound>

The photosensitive layer may optionally contain an electron transport material or an electron acceptor compound depending on necessity thereof. The single-layer type photosensitive layer of the single-layer photosensitive member may contain an electron transport material. Through inclusion of the electron transport material, the single-layer type photosensitive layer can transport electrons and the single-layer type photosensitive layer can be easily provided with bipolar properties. On the other hand, the multi-layer type photosensitive layer of the multi-layer photosensitive member may contain an electron acceptor compound. Inclusion of the electron acceptor compound tends to improve hole transport by the hole transport material.

Examples of electron transport materials and electron acceptor compounds that may be used include quinone-based compounds (specifically, naphthoquinone-based compounds, diphenoquinone-based compounds, anthraquinone-based compounds, azoquinone-based compounds, nitroanthraquinone-based compounds, and dinitroanthraquinone-based compounds), malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroanthracene, dinitroacridine, succinic anhydride, maleic anhydride, and dibromomaleic anhydride. Any one electron transport material may be used or a combination of any two or more electron transport materials may be used. Furthermore, any one electron acceptor compound may be used or a combination of any two or more electron acceptor compounds may be used.

Specific examples of electron transport materials and electron acceptor compounds that may be used include compounds represented by general formulae (ETM-I) to (ETM-IV) shown below.

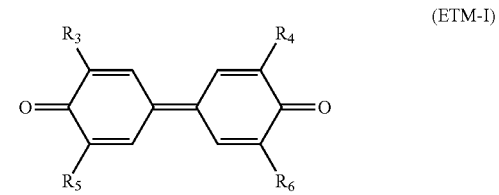

(ETM-I)

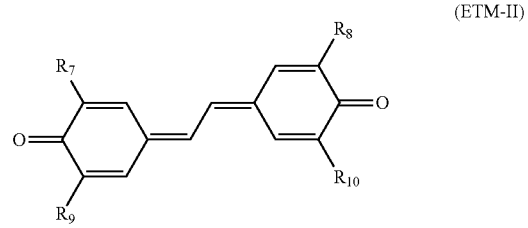

(ETM-II)

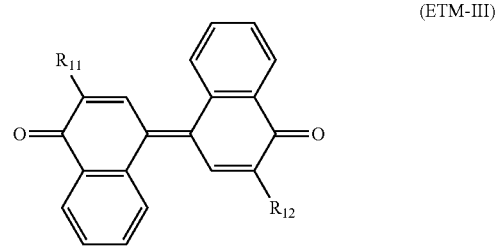

(ETM-III)

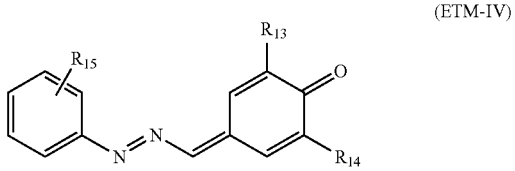

(ETM-IV)

In the general formulae (ETM-I) to (ETM-IV), $R_3$ to $R_{14}$ represent, independently of one another, the same chemical group or different chemical groups selected from the group consisting of a hydrogen atom, an optionally substituted alkyl group, an optionally substituted alkenyl group, an optionally substituted alkoxy group, an optionally substituted aralkyl group, an optionally substituted aromatic hydrocarbon group, and an optionally substituted heterocyclic group. $R_{15}$ represents a chemical group selected from the group consisting of a halogen atom, a hydrogen atom, an optionally substituted alkyl group, an optionally substituted alkenyl group, an optionally substituted alkoxy group, an optionally substituted aralkyl group, an optionally substituted aromatic hydrocarbon group, and an optionally substituted heterocyclic group.

Examples of alkyl groups that may be represented by $R_3$ to $R_{15}$ in general formulae (ETM-I) to (ETM-IV) include alkyl groups having a carbon number of at least 1 and no greater than 10. Preferable examples include alkyl groups having a carbon number of at least 1 and no greater than 6. More preferable examples include alkyl groups having a carbon number of at least 1 and no greater than 4. Particularly preferable examples include a methyl group, a tert-butyl group, and a 1,1-dimethylpropyl group. The alkyl group may be a straight chain alkyl group, a branched chain alkyl group, a ring alkyl group, or an alkyl group that is any combination thereof. Examples of possible substituents of the alkyl group include halogen atoms, a hydroxyl group, alkoxy groups having a carbon number of at least 1 and no greater than 4, and a cyano group. Although no particular limitations are placed on the number of substituents of the alkyl group, the alkyl group preferably has no greater than three substituents.

Examples of alkenyl groups that may be represented by $R_3$ to $R_{15}$ in general formulae (ETM-I) to (ETM-IV) include alkenyl groups having a carbon number of at least 2 and no greater than 10. Preferable examples include alkenyl groups having a carbon number of at least 2 and no greater than 6. More preferable examples include alkenyl groups having a carbon number of at least 2 and no greater than 4. The alkenyl group may be a straight chain alkenyl group, a branched chain alkenyl group, a ring alkenyl group, or an alkenyl group that is any combination thereof. Examples of possible substituents of the alkenyl group include halogen atoms, a hydroxyl group, alkoxy groups having a carbon number of at least 1 and no greater than 4, and a cyano group. Although no particular limitations are placed on the number of substituents of the alkenyl group, the alkenyl group preferably has no greater than three substituents.

Examples of alkoxy groups that may be represented by $R_3$ to $R_{15}$ in general formulae (ETM-I) to (ETM-IV) include alkoxy groups having a carbon number of at least 1 and no greater than 10. Preferable examples include alkoxy groups having a carbon number of at least 1 and no greater than 6. More preferable examples include alkoxy groups having a carbon number of at least 1 and no greater than 4. The alkoxy group may be a straight chain alkoxy group, a branched chain alkoxy group, a ring alkoxy group, or an alkoxy group that is any combination thereof. Examples of possible substituents of the alkoxy group include halogen atoms, a hydroxyl group, alkoxy groups having a carbon number of at least 1 and no greater than 4, and a cyano group. Although no particular limitations are placed on the number of substituents of the alkoxy group, the alkoxy group preferably has no greater than three substituents.

Examples of aralkyl groups that may be represented by $R_3$ to $R_{15}$ in general formulae (ETM-I) to (ETM-IV) include aralkyl groups having a carbon number of at least 7 and no greater than 15. Preferable examples include aralkyl groups having a carbon number of at least 7 and no greater than 13. More preferable examples include aralkyl groups having a carbon number of at least 7 and no greater than 12. Examples of possible substituents of the aralkyl group include halogen atoms, a hydroxyl group, alkyl groups having a carbon number of at least 1 and no greater than 4, alkoxy groups having a carbon number of at least 1 and no greater than 4, a nitro group, a cyano group, aliphatic acyl groups having a carbon number of at least 2 and no greater than 4, a benzoyl group, a phenoxy group, alkoxycarbonyl groups including an alkoxy group having a carbon number of at least 1 and no greater than 4, and a phenoxycarbonyl group. Although no particular limitations are placed on the number of substituents of the aralkyl group, the aralkyl group preferably has no greater than five substituents and more preferably no greater than three substituents.

Examples of aromatic hydrocarbon groups that may be represented by $R_3$ to $R_{15}$ in general formulae (ETM-I) to (ETM-IV) include a phenyl group, groups resulting from condensation of two or three benzene rings, and groups resulting from single bonding of two or three benzene rings. The aromatic hydrocarbon group for example includes at least one and no greater than three benzene rings with one or two benzene rings being preferable. Possible substituents of the aromatic hydrocarbon group include halogen atoms, a hydroxyl group, alkyl groups having a carbon number of at least 1 and no greater than 4, alkoxy groups having a carbon number of at least 1 and no greater than 4, a nitro group, a cyano group, aliphatic acyl groups having a carbon number of at least 2 and no greater than 4, a benzoyl group, a phenoxy group, alkoxycarbonyl groups including an alkoxy group having a carbon number of at least 1 and no greater than 4, and a phenoxycarbonyl group.

Examples of heterocyclic groups that may be represented by $R_3$ to $R_{15}$ in general formulae (ETM-I) to (ETM-IV) include heterocyclic groups formed by a five or six member monocyclic ring including at least one hetero atom selected from the group consisting of N, S, and O, heterocyclic groups resulting from condensation of a plurality of such monocyclic rings, and heterocyclic groups resulting from condensation of such a monocyclic ring with a five or six member hydrocarbon ring. In a configuration in which the heterocyclic group is a condensed ring structure, the condensed ring structure preferably includes no greater than three rings. Possible substituents of the heterocyclic group include halogen atoms, a hydroxyl group, alkyl groups having a carbon number of at least 1 and no greater than 4, alkoxy groups having a carbon number of at least 1 and no greater than 4, a nitro group, a cyano group, aliphatic acyl groups having a carbon number of at least 2 and no greater than 4, a benzoyl group, a phenoxy group, alkoxycarbonyl groups including an alkoxy group having a carbon number of at least 1 and no greater than 4, and a phenoxycarbonyl group.

Examples of halogen atoms that may be represented by $R_{15}$ in general formula (ETM-IV) include a fluorine atom (fluoro group), a chlorine atom (chloro group), a bromine atom (bromo group), and an iodine atom (iodo group), with a chlorine atom (chloro group) being preferable.

The amount of the electron acceptor compound in the multi-layer photosensitive member is preferably at least 0.1 parts by mass and no greater than 20 parts by mass relative to 100 parts by mass of a binder resin contained in the charge transport layer, and more preferably at least 0.5 parts by mass and no greater than 10 parts by mass.

The amount of the electron transport material in the single-layer photosensitive member is preferably at least 5 parts by mass and no greater than 100 parts by mass relative to 100 parts by mass of a binder resin contained in the single-layer type photosensitive layer, and more preferably at least 10 parts by mass and no greater than 80 parts by mass.

<3-5. Base Resin>

The charge generating layer of the multi-layer photosensitive member contains a charge generating layer binder resin (also referred to as a base resin).

No particular limitations are placed on the base resin other than being a resin that can be used in a charge generating layer of a multi-layer photosensitive member.

The multi-layer photosensitive member typically has a charge generating layer and a charge transport layer formed therein. Therefore, the base resin used in the multi-layer photosensitive member preferably differs from the binder resin in order that the base resin does not dissolve in a solvent of an application liquid used during formation of the charge transport layer.

Specific examples of base resins that may be used include styrene-butadiene copolymers, styrene-acrylonitrile copolymers, styrene-maleate copolymers, acrylic copolymers, styrene-acrylate copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, urethane resins, polysulfone resins, diallyl phthalate resins, ketone resins, polyvinyl acetal resins, polyvinyl butyral resins, polyether resins, silicone resins, epoxy resins, phenolic resins, urea resins, melamine resins, epoxy acrylates (acrylic acid adducts of epoxy compounds), and urethane-acrylates (acrylic acid adducts of urethane compounds). Use of a polyvinyl butyral resin as the base resin is preferable. Any one of the base resins listed above may be used or a combination of any two or more of the base resins listed above may be used.

<3-6. Binder Resin>

The single-layer type photosensitive layer of the single-layer photosensitive member contains a binder resin. The charge transport layer of the multi-layer photosensitive member contains a binder resin. Examples of binder resins that may be used include thermoplastic resins (specifically, polycarbonate resins, styrene-based resins, styrene-butadiene copolymers, styrene-acrylonitrile copolymers, styrene-maleate copolymers, styrene-acrylate copolymers, acrylic copolymers, polyethylene resins, ethylene-vinyl acetate copolymers, chlorinated polyethylene resins, polyvinyl chloride resins, polypropylene resins, ionomers, vinyl chloride-vinyl acetate copolymers, alkyd resins, polyamide resins, urethane resins, polyarylate resins, polysulfone resins, diallyl phthalate resins, ketone resins, polyvinyl butyral resins, polyether resins, and polyester resins), thermosetting resins (specifically, silicone resins, epoxy resins, phenolic resins, urea resins, melamine resins, and other crosslinkable thermosetting resins), and photocurable resins (specifically, epoxy acrylates (acrylic acid adducts of epoxy compounds) and urethane-acrylates (acrylic acid adducts of urethane compounds)).

Among the binder resins listed above, polycarbonate resins are preferable for obtaining a single-layer type photosensitive layer and a charge transport layer having excellent balance in terms of processability, mechanical properties, optical properties, and abrasion resistance. Preferable examples of polycarbonate resins include bisphenol Z polycarbonate resin, bisphenol ZC polycarbonate resin, bisphenol C polycarbonate resin, and bisphenol A polycarbonate resin. A specific example of the bisphenol Z polycarbonate resin is the resin represented by the chemical formula shown below. Note that the number attached to the repeating unit in the following chemical formula indicates the molar ratio (mol %) of the repeating unit relative to the total number of moles of repeating units included in the resin.

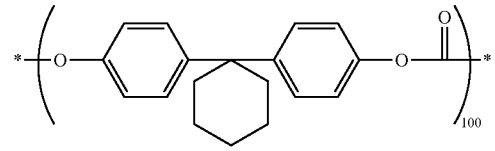

Any one of the binder resins listed above may be used or a combination of any two or more of the binder resins listed above may be used.

In terms of molecular weight, the binder resin preferably has a viscosity average molecular weight of at least 40,000, and more preferably at least 40,000 and no greater than 52,500. If the molecular weight of the binder resin is too low, the binder resin may have insufficient abrasion resistance and, as a consequence, abrasion of the charge transport layer or the single-layer type photosensitive layer may have a high tendency to occur. On the other hand, if the molecular weight of the binder resin to too large, formation of the charge transport layer or the single-layer type photosensitive layer tends to be difficult due to the binder resin having a low tendency to dissolve in a solvent during formation of the charge transport layer or the single-layer type photosensitive layer.

<3-7. Additives>

In the configuration in which the photosensitive member is the multi-layer photosensitive member, one or more of the charge generating layer, the charge transport layer, an intermediate layer, and a protective layer may optionally contain various additives depending on necessity thereof. In the configuration in which the photosensitive member is the single-layer photosensitive member, one or more of the single-layer type photosensitive layer, an intermediate layer, and a protective layer may optionally contain various additives depending on necessity thereof. Examples of additives that may be used include antidegradants (specifically, antioxidants, radical scavengers, singlet quenchers, and ultraviolet absorbing agents), softeners, surface modifiers, extenders, thickeners, dispersion stabilizers, waxes, acceptors, donors, surfactants, plasticizers, sensitizers, and leveling agents. Specific examples of antioxidants include BHT (di(tert-butyl)p-cresol), hindered phenols, hindered amines, paraphenylenediamine, arylalkanes, hydroquinone, spirochromanes, spiroindanones, derivatives of any of the above compounds, organosulfur compounds, and organophosphorus compounds.

<3-8. Intermediate Layer>

The photosensitive member according to the present embodiment may optionally include an intermediate layer (for example, an underlayer). In the single-layer photosensitive member, the intermediate layer is present between the conductive substrate and the single-layer type photosensitive layer. In the multi-layer photosensitive member, the intermediate layer is present between the conductive substrate and the charge generating layer. The intermediate layer for example contains inorganic particles and a resin for intermediate layer use (intermediate layer resin). Provision of the intermediate layer may facilitate flow of current generated when the photosensitive member is exposed to light and inhibit increasing resistance, while also maintaining insulation to a sufficient degree so as to inhibit leakage current from occurring.

Examples of inorganic particles that may be used include particles of metals (specifically, aluminum, iron, and copper), particles of metal oxides (specifically, titanium oxide, alumina, zirconium oxide, tin oxide, and zinc oxide), and particles of non-metal oxides (specifically, silica). Any one type of inorganic particles listed above may be used or a combination of any two or more types of inorganic particles listed above may be used.

No particular limitations are placed on the intermediate layer resin other than being a resin that can be used to form an intermediate layer.

<4. Photosensitive Member Production Method>

The following explains an example of a production method for the single-layer photosensitive member. The single-layer photosensitive member is produced by applying an application liquid for single-layer type photosensitive layer formation (first application liquid) onto a conductive substrate and drying the first application liquid thereon. The first application liquid is prepared by dissolving or dispersing a charge generating material, a hole transport material, and optional components (for example, a binder resin, an electron transport material, and various additives), depending on necessity thereof, in a solvent.

The following explains an example of a production method for the multi-layer photosensitive member. Specifically, an application liquid for charge generating layer formation (second application liquid) and an application liquid for charge transport layer formation (third application liquid) are first prepared. The second application liquid is applied onto a conductive substrate and dried thereon by an appropriate method. A charge generating layer is formed as a result. After formation of the charge generating layer, the third application liquid is applied onto the charge generating layer and dried thereon to form a charge transport layer. Through the above process, the multi-layer photosensitive member is produced.

The second application liquid is prepared by dissolving or dispersing a charge generating material and optional components (for example, a base resin and various additives), depending on necessity thereof, in a solvent. The third application liquid is prepared by dissolving or dispersing a hole transport material and optional components (for example, a binder resin, an electron acceptor compound, and various additives), depending on necessity thereof, in a solvent.

No particular limitations are placed on the solvents contained in the application liquids (first application liquid, second application liquid, and third application liquid) other than that the components of each of the application liquids should be soluble or dispersible in the solvent. Specific examples of solvents that may be used include alcohols (for example, methanol, ethanol, isopropanol, and butanol), aliphatic hydrocarbons (for example, n-hexane, octane, and cyclohexane), aromatic hydrocarbons (for example, benzene, toluene, and xylene), halogenated hydrocarbons (for example, dichloromethane, dichloroethane, carbon tetrachloride, and chlorobenzene), ethers (for example, dimethyl ether, diethyl ether, tetrahydrofuran, ethylene glycol dimethyl ether, diethylene glycol dimethyl ether, and propylene glycol monomethyl ether), ketones (for example, acetone, methyl ethyl ketone, and cyclohexanone), esters (for example, ethyl acetate and methyl acetate), dimethyl formaldehyde, dimethyl formamide, and dimethyl sulfoxide. Any one of the solvents listed above may be used or a combination of any two or more of the solvents listed above may be used. In order to improve workability in production of the photosensitive member, a non-halogenated solvent (i.e., a solvent other than a halogenated hydrocarbon) is preferably used.

Each of the application liquids is prepared by mixing the components in order to disperse the components in the solvent. Mixing or dispersion can for example be performed using a bead mill, a roll mill, a ball mill, an attritor, a paint shaker, or an ultrasonic disperser.

The application liquid may for example further contain a surfactant in order to improve dispersibility of the components.

No particular limitations are placed on the method by which the application liquid is applied so long as the method enables uniform application of an application liquid onto a conductive substrate. Examples of application methods that may be used include dip coating, spray coating, spin coating, and bar coating.

No particular limitations are placed on the method by which the application liquid is dried other than being a method for evaporating a solvent contained in an application liquid. The method of drying may for example be heat treatment (hot-air drying) using a high-temperature dryer or a reduced pressure dryer. The heat treatment is for example performed for at least 3 minutes and no greater than 120 minutes at a temperature of at least 40° C. and no greater than 150° C.

The photosensitive member can for example be used as an image bearing member in an image forming apparatus including a charging section (contact charging section) that applies a direct current voltage to the image bearing member while in contact with the image bearing member. In such a configuration, the charging section may charge the surface of the image bearing member to a positive polarity (i.e., the charging section may have a positive charging polarity) and the photosensitive layer of the photosensitive member may be the single-layer type photosensitive layer. The contact charging section that applies the direct current voltage is explained below in a third embodiment.

Through the above, an explanation of the photosensitive member according to the present embodiment has been provided. Through the photosensitive member according to the present embodiment, electrical properties can be improved while also maintaining excellent external appearance of the photosensitive member (i.e., inhibiting crystallization in the photosensitive layer). In addition, transfer memory can be inhibited from occurring through the photosensitive member according to the present embodiment.

<Third Embodiment: Image Forming Apparatus>

The third embodiment pertains to an image forming apparatus. The following explains an image forming apparatus 6 according to the present embodiment with reference to FIGS. 4 and 5.

Figure 4:
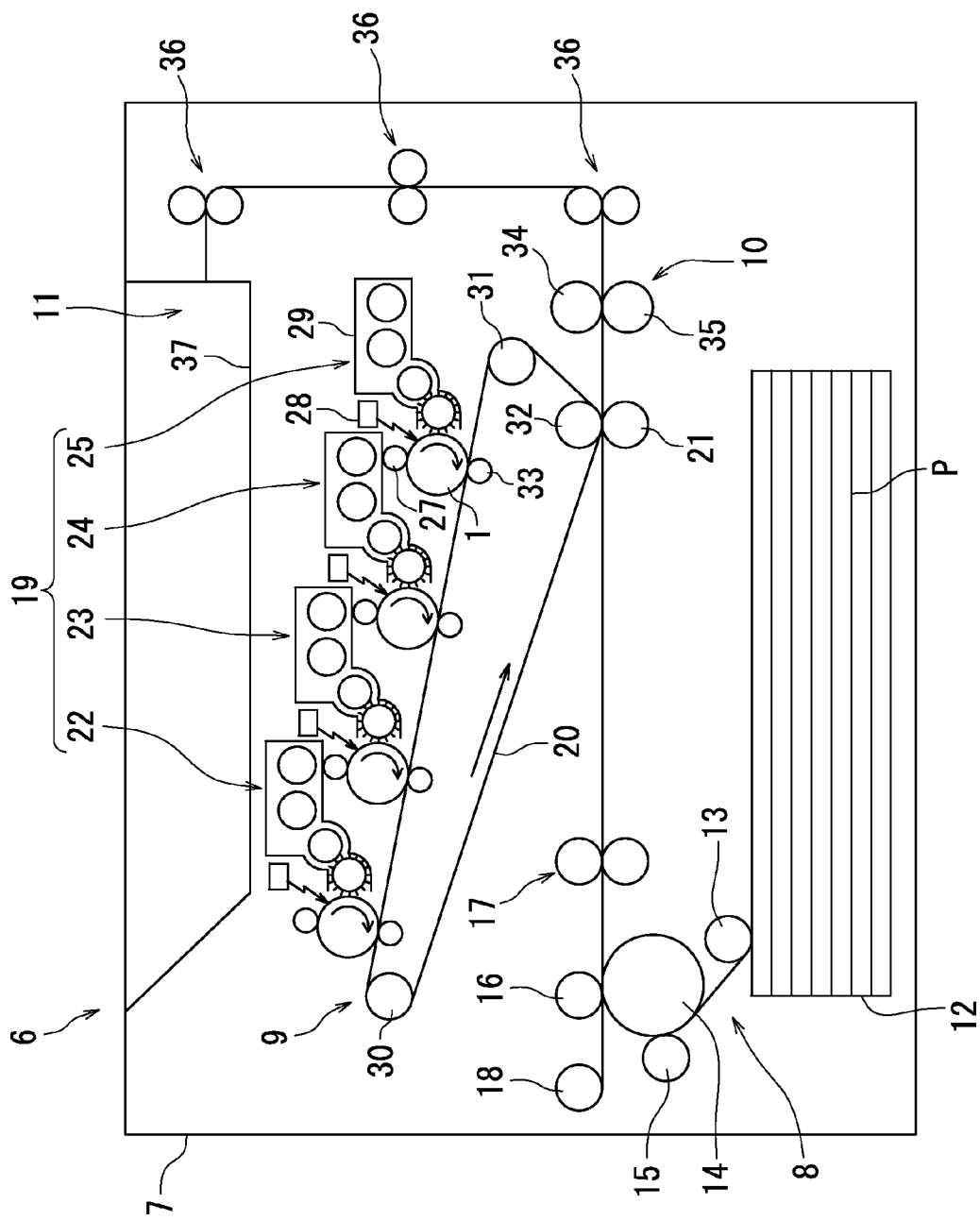
FIG. 4 roughly illustrates an example of an image forming apparatus according to an embodiment of the present disclosure.

An example in which the image forming apparatus 6 adopts an intermediate transfer process is explained with reference to FIG. 4. An example in which the image forming apparatus 6 adopts a direct transfer process is explained further below. FIG. 4 roughly illustrates an example of the image forming apparatus 6 according to the present embodiment.

The image forming apparatus 6 includes a photosensitive member 1 as an image bearing member, a charging section (equivalent to a charging device) 27, a light exposure section 28 (equivalent to a light exposure device), a developing section 29, and a transfer section. In the configuration in which the image forming apparatus 6 adopts the intermediate transfer process, the transfer section is equivalent to a primary transfer roller 33 and a secondary transfer roller 21.

The charging section 27 charges the surface of the photosensitive member 1 (i.e., the image bearing member). The light exposure section 28 forms an electrostatic latent image on the surface of the photosensitive member 1 (i.e., the image bearing member) by exposing the surface of the photosensitive member 1 to light while in a charged state. The developing section 29 develops the electrostatic latent image into a toner image. The transfer section transfers the toner image onto a transfer target from the image bearing member. In the configuration in which the image forming apparatus 6 adopts the intermediate transfer process, the transfer target is equivalent to an intermediate transfer belt 20 and a recording medium (for example, paper P). The photosensitive member 1 used as the image bearing member is the photosensitive member 1 according to the second embodiment. The photosensitive layer 3 of the photosensitive member 1 contains the triarylamine derivative (I) according to the first embodiment.

No particular limitations are placed on the image forming apparatus 6 other than being an electrophotographic image forming apparatus. The image forming apparatus 6 may for example be a monochrome image forming apparatus or a color image forming apparatus. The image forming apparatus 6 according to the present embodiment may be a tandem color image forming apparatus that forms toner images of different colors using different color toners.

The following explains an example in which the image forming apparatus 6 is a tandem color image forming apparatus. The image forming apparatus 6 includes a plurality of the photosensitive members 1 arranged in a specific direction and a plurality of the developing sections (equivalent to developing devices, for example development rollers) 29. The developing sections 29 are arranged in one-to-one correspondence with the photosensitive members 1. Each of the developing sections 29 conveys toner while bearing the toner on a surface thereof. The developing section 29 supplies the conveyed toner onto the surface of a corresponding one of the photosensitive members 1.

As illustrated in FIG. 4, the image forming apparatus 6 has a box shaped apparatus housing 7. The apparatus housing 7 houses a paper feed section 8, an image forming section 9, and a fixing section 10. The paper feed section 8 feeds paper P. The image forming section 9 transfers a toner image based on image data onto the paper P fed from the paper feed section 8 while conveying the paper P. The fixing section 10 fixes, to the paper P, the unfixed toner image that has been transferred onto the paper P by the image forming section 9. A paper ejection section 11 is provided on a top surface of the apparatus housing 7. The paper ejection section 11 ejects the paper P after the paper P has been subjected to a fixing process by the fixing section 10.

The paper feed section 8 includes a paper feed cassette 12, a pick-up roller 13, paper feed rollers 14, 15, and 16, and a pair of registration rollers 17. The paper feed cassette 12 is detachable from the apparatus housing 7. Various sizes of paper P can be loaded into the paper feed cassette 12. The pick-up roller 13 is located above a left-hand side of the paper feed cassette 12. The pick-up roller 13 picks up paper P one sheet at a time from the paper feed cassette 12 in which the paper P is loaded. The paper feed rollers 14, 15, and 16 convey the paper P that is picked up by the pick-up roller 13. The pair of registration rollers 17 temporarily halts the paper P that is conveyed by the paper feed rollers 14, 15, and 16, and subsequently feeds the paper P to the image forming section 9 at a specific timing.

The paper feed section 8 further includes a manual feed tray (not illustrated) and a pick-up roller 18. The manual feed tray is attached to a left side surface of the apparatus housing 7. The pick-up roller 18 picks up paper P that is loaded on the manual feed tray. The paper P that is picked up by the pick-up roller 18 is then conveyed by the paper feed rollers 14 and 16, and fed to the image forming section 9 at the specific timing by the pair of registration rollers 17.

The image forming section 9 includes an image forming unit 19, an intermediate transfer belt 20, and a secondary transfer roller 21. The image forming unit 19 performs primary transfer of a toner image onto a surface of the intermediate transfer belt 20 (i.e., a surface in contact with primary transfer rollers 33). The toner image that is subjected to primary transfer is formed based on image data that is transmitted from a higher-level device such as a computer. The secondary transfer roller 21 performs secondary transfer of the toner image on the intermediate transfer belt 20 to paper P that is fed from the paper feed cassette 12.

The image forming unit 19 includes a magenta toner supply unit 25, a cyan toner supply unit 24, a yellow toner supply unit 23, and a black toner supply unit 22 that are arranged in stated order from upstream (right side of FIG. 4) to downstream. Each of the photosensitive members 1 (equivalent to image bearing members) is provided at a central position in a corresponding one of the toner supply units 22, 23, 24, and 25. The photosensitive member 1 is rotatable in an arrow direction (i.e., clockwise).

Around each of the photosensitive members 1, the charging section 27, the light exposure section 28, the developing section 29, a cleaning device (not illustrated), and a static eliminator (not illustrated) are arranged in stated order from upstream to downstream in the rotation direction of the photosensitive member 1.

The charging section 27 charges the surface of the photosensitive member 1. More specifically, the charging section 27 uniformly charges a circumferential surface of the photosensitive member 1 as the photosensitive member 1 rotates in the arrow direction. No particular limitations are placed on the charging section 27 so long as the charging section can uniformly charge the circumferential surface of the photosensitive member 1. The charging section 27 may be a non-contact charging section or a contact charging section. In a configuration in which the charging section 27 is a contact charging section, the charging section 27 applies voltage to the photosensitive member 1 while in contact with the photosensitive member 1. In a configuration in which the charging section 27 is a non-contact charging section, the charging section 27 applies voltage to the photosensitive member 1 without being in contact with the photosensitive member 1. When the charging section 27 is a contact charging section, the charging section 27 is for example a contact (proximity) discharge charging device and more specifically is for example a charging roller or a charging brush. When the charging section 27 is a non-contact charging section, the charging section 27 is for example a corona discharge charging device and, more specifically, is for example a corotron charging device or a scorotron charging device. The charging section 27 is preferably a contact charging section (specifically, a charging roller or a charging brush), with a charging roller being particularly preferable.

In a configuration in which the charging section 27 is a contact charging roller, the charging roller charges the circumferential surface (surface) of the photosensitive member 1 while in contact with the photosensitive member 1. The charging roller may for example be rotationally driven by rotation of the photosensitive member 1 while in contact with the photosensitive member 1. Furthermore, at least a surface section of the charging roller may for example be formed from a resin. In a more specific example, the charging roller includes a metal core that is axially supported in a rotatable manner, a resin layer formed on the metal core, and a voltage application section that applies voltage to the metal core. In a configuration in which the charging section 27 includes a charging roller such as described above, the surface of the photosensitive member 1 can be charged via the resin layer in contact with the photosensitive member 1 as a result of the voltage applying section applying voltage to the metal core.

No particular limitations are placed on the resin forming the resin layer of the charging roller, so long as the resin enables favorable charging of the circumferential surface of the photosensitive member 1. Specific examples of resins that may be used to the form the resin layer include silicone resins, urethane resins, and silicone modified resins. The resin layer may optionally contain an inorganic filler.

Emission of active gases (for example, ozone and nitrogen oxides) produced by the charging section 27 can be restricted in a configuration in which the charging section 27 is a contact charging section. As a result, degradation of the photosensitive layer 3 by the active gases can be inhibited while also enabling apparatus design that takes into account use in an office environment.

It should be noted that an image forming apparatus that includes a contact charging section 27 is more susceptible to occurrence of transfer memory than an image forming apparatus that includes a non-contact charging section 27. Fortunately, the photosensitive member 1 according to the second embodiment inhibits transfer memory from occurring as already explained above. Therefore, transfer memory can be inhibited from occurring even when the photosensitive member 1 is used in the configuration in which the image forming apparatus 6 includes the contact charging section 27.

Furthermore, transfer memory has a particularly high tendency to occur in a configuration in which a contact charging section 27 that has a positive charging polarity is used in combination with a photosensitive member 1 that includes a single-layer type photosensitive layer 3a. Fortunately, the photosensitive member 1 according to the second embodiment inhibits transfer memory from occurring as already explained above. Therefore, transfer memory can be inhibited from occurring even when the photosensitive member 1 is used in the configuration in which the image forming apparatus 6 includes the contact charging section 27 that has a positive charging polarity and in which the photosensitive layer 3 of the photosensitive member 1 is the single-layer type photosensitive layer 3a.

No particular limitations are placed on the voltage applied by the charging section 27. However, it is more preferable for the charging section 27 to only apply a direct current voltage than for the charging section 27 to apply an alternating current voltage or a superimposed voltage of an alternating current voltage superimposed on a direct current voltage. The reason for the above is that abrasion of the photosensitive layer 3 tends to be smaller in a configuration in which the charging section 27 only applies a direct current voltage. Furthermore, when a photosensitive member 1 is used in an image forming apparatus including a charging section 27 that applies an alternating current voltage, stability of surface potential of the photosensitive member 1 may be reduced by application of an opposite polarity bias (for example, a negative component). The negative component (opposite polarity bias) is applied to the photosensitive member 1 via a transfer target (intermediate transfer belt 20) during transfer. Fortunately, the photosensitive member 1 enables rapid movement of opposite polarity charge, stabilizing potential of the photosensitive member 1. As a result, the effect of inhibiting occurrence of transfer memory is thought to be particularly pronounced in the situation described above.

The charging section 27 preferably applies a direct current voltage to the photosensitive member 1 of at least 1,000 V and no greater than 2,000 V, more preferably at least 1,200 V and no greater than 1,800 V, and particularly preferably at least 1,400 V and no greater than 1,600 V.

The light exposure section 28 is a so-called laser scanning unit. The light exposure section 28 forms an electrostatic latent image on the surface of the photosensitive member 1 (i.e., the image bearing member) by exposing the surface of the photosensitive member 1 to light while in a charged state. More specifically, after the circumferential surface (surface) of the photosensitive member 1 has been uniformly charged by the charging section 27, the light exposure section 28 irradiates the circumferential surface of the photosensitive member 1 with laser light based on image data input from a higher-level device such as a personal computer. Through the above, an electrostatic latent image based on the image data is formed on the circumferential surface (surface) of the photosensitive member 1.

The developing section 29 develops the electrostatic latent image into a toner image. More specifically, the developing section 29 forms a toner image based on the image data by supplying toner to the circumferential surface of the photosensitive member 1 once the electrostatic latent image has been formed thereon. Next, primary transfer of the formed toner image onto the intermediate transfer belt 20 is performed. Once primary transfer of the toner image onto the intermediate transfer belt 20 is complete, the cleaning device cleans residual toner off of the circumferential surface of the photosensitive member 1. Also, once primary transfer of the toner image onto the intermediate transfer belt 20 is complete, the static eliminator eliminates static electricity from the circumferential surface of the photosensitive member 1. After the circumferential surface of the photosensitive member 1 has been cleaned by the cleaning device and static electricity has been eliminated from the circumferential surface by the static eliminator, the circumferential surface of the photosensitive member 1 returns to a position corresponding to the charging section 27 and a new charging process is performed.

The intermediate transfer belt 20 is an endless circulating belt. The intermediate transfer belt 20 is stretched around a drive roller 30, a driven roller 31, a backup roller 32, and the primary transfer rollers 33. The intermediate transfer belt 20 is positioned such that circumferential surfaces of the photosensitive members 1 are each in contact with a surface (contact surface) of the intermediate transfer belt 20.

The intermediate transfer belt 20 is pressed against each of the photosensitive members 1 by a corresponding one of the primary transfer rollers 33 that is located opposite to the photosensitive member 1. The intermediate transfer belt 20 circulates endlessly while in the pressed state through the primary transfer rollers 33. The drive roller 30 is rotationally driven by a drive source such as a stepper motor and imparts driving force on the intermediate transfer belt 20 that causes endless circulation of the intermediate transfer belt 20. The driven roller 31, the backup roller 32, and the primary transfer rollers 33 are freely rotatable. The driven roller 31, the backup roller 32, and the primary transfer rollers 33 passively rotate in accompaniment to endless circulation of the intermediate transfer belt 20 by the drive roller 30. The driven roller 31, the backup roller 32, and the primary transfer rollers 33 passively rotate through the intermediate transfer belt 20, in response to active rotation of the drive roller 30, while supporting the intermediate transfer belt 20.

The transfer section (equivalent to the primary transfer rollers 33 and the secondary transfer roller 21) transfers toner images from the photosensitive members 1, which act as image bearing members, to a transfer target (intermediate transfer belt 20 and paper P). More specifically, each of the primary transfer rollers 33 applies a primary transfer bias (specifically, a bias of opposite polarity to toner charging polarity) to the intermediate transfer belt 20 (equivalent to a transfer target). As a result, toner images formed on the photosensitive members 1 are transferred (primary transfer) onto the intermediate transfer belt 20 in order as the intermediate transfer belt 20 is driven by the drive roller 30 to circulate in an arrow direction (i.e., counter-clockwise) between each of the photosensitive members 1 and the corresponding primary transfer roller 33.

The secondary transfer roller 21 applies a secondary transfer bias (specifically, a bias of opposite polarity to the toner images) to the paper P. As a result, the toner images that have been transferred onto the intermediate transfer belt 20 by primary transfer are transferred onto the paper P between the secondary transfer roller 21 and the backup roller 32. Through the above, an unfixed toner image is transferred onto the paper P.

The fixing section 10 fixes, to the paper P, the unfixed toner image that has been transferred onto the paper P by the image forming section 9. The fixing section 10 includes a heating roller 34 and a pressure roller 35. The heating roller 34 is heated by a conductive heating element. The pressure roller 35 is located opposite to the heating roller 34 and has a circumferential surface that is pressed against a circumferential surface of the heating roller 34.

The transferred image that has been transferred onto the paper P by the secondary transfer roller 21 in the image forming section 9 is subsequently fixed to the paper P through a fixing process in which the paper P is heated as the paper P passes between the heating roller 34 and the pressure roller 35. After the paper P has been subjected to the fixing process, the paper P is ejected to the paper ejection section 11. Conveyance rollers 36 are provided at appropriate locations between the fixing section 10 and the paper ejection section 11.

The paper ejection section 11 is formed by a recess in a top part of the apparatus housing 7. An exit tray 37 for receiving the ejected paper P is provided at the bottom of the recess.

Through the above, an explanation of the image forming apparatus 6 has been provided for the configuration in which the image forming apparatus 6 adopts the intermediate transfer process with reference to FIG. 4. However, the photosensitive member 1 according to the second embodiment is also suitable for use in an image forming apparatus that adopts a direct transfer process. The direct transfer process involves direct transfer of a developed toner image on the surface of the photosensitive member 1 to paper P conveyed by a transfer belt. In a configuration in which the image forming apparatus 6 adopts a direct transfer process, there is a greater tendency for extraneous matter arising from the paper P to become attached to the surface of the photosensitive member 1. Attachment of such extraneous matter may result in reduced chargeability of the photosensitive member 1. Due to the influence of such reduced chargeability of the photosensitive member 1, the image forming apparatus 6 is more susceptible to occurrence of transfer memory in the configuration in which the image forming apparatus 6 adopts the direct transfer process. Fortunately, the image forming apparatus 6 includes the photosensitive member 1. As explained above in the second embodiment, the photosensitive member 1 can inhibit transfer memory from occurring. Therefore, transfer memory can be effectively inhibited even in the configuration in which the image forming apparatus 6 adopts the direct transfer process.

Figure 5:
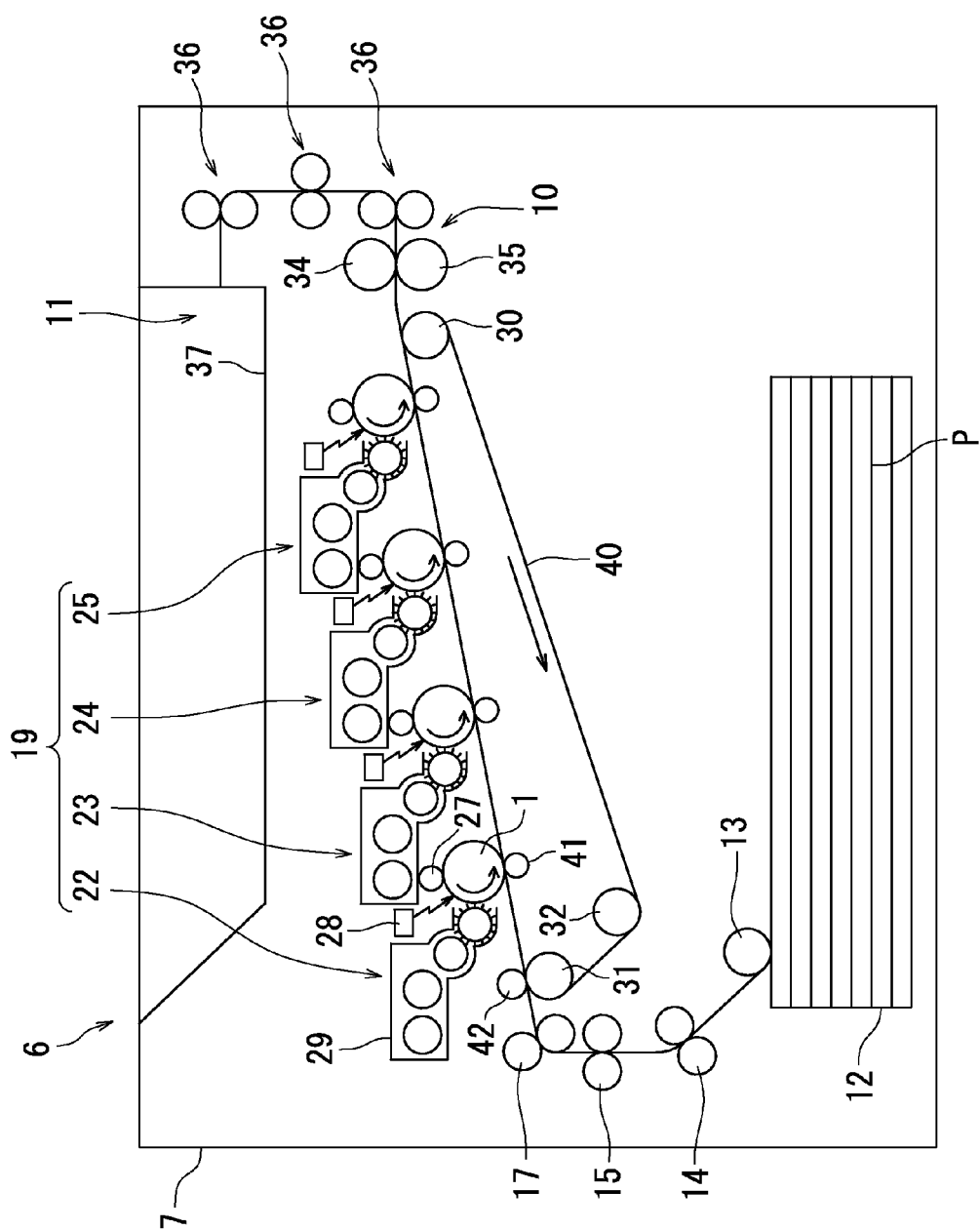
FIG. 5 roughly illustrates another example of an image forming apparatus according to an embodiment of the present disclosure.

The following explains the image forming apparatus 6 according to an alternative aspect of the present embodiment with reference to FIG. 5. FIG. 5 roughly illustrates another example of the image forming apparatus 6. The image forming apparatus 6 illustrated in FIG. 5 adopts the direct transfer process. In the image forming apparatus 6 illustrated in FIG. 5, the transfer section is equivalent to transfer rollers 41. Also, the transfer target is equivalent to a recording medium (for example, paper P). Elements in FIG. 5 that correspond to elements in FIG. 4 are labelled using the same reference signs and explanation thereof is not repeated.

A transfer belt 40 illustrated in FIG. 5 is an endless circulating belt. The transfer belt 40 is stretched around the drive roller 30, the driven roller 31, the backup roller 32, and transfer rollers 41. The transfer belt 40 is positioned such that circumferential surfaces of the photosensitive members 1 are each in contact with the surface (contact surface) of the transfer belt 40. The transfer belt 40 is pressed against each of the photosensitive members 1 by the corresponding transfer roller 41 located opposite to the photosensitive member 1. The transfer belt 40 circulates endlessly while in a pressed state through the rollers 30, 31, 32, and 41. The drive roller 30 is rotationally driven by a drive source such as a stepper motor and imparts driving force that causes endless circulation of the transfer belt 40. The driven roller 31, the backup roller 32, and the transfer rollers 41 are freely rotatable. The driven roller 31, the backup roller 32, and the transfer rollers 41 are rotationally driven in accompaniment to endless circulation of the transfer belt 40 by the drive roller 30. The rollers 31, 32, and 41 passively rotate while supporting the transfer belt 40. Paper P supplied by the pair of registration rollers 17 is caused to be sucked onto the transfer belt 40 by a paper holding roller 42. The paper P sucked onto the transfer belt 40 passes between the photosensitive members 1 and the corresponding transfer rollers 41 as the transfer belt 40 circulates.

Each of the transfer rollers 41 applies a transfer bias (bias of opposite polarity to toner charging polarity) to the paper P that is sucked onto the transfer belt 40. As a result, a toner image formed on each of the photosensitive members 1 is transferred onto the paper P as the paper P passes between the photosensitive member 1 and the corresponding transfer roller 41. The photosensitive member 1 is in contact with the paper P during transfer of the toner image onto the paper P from the photosensitive member 1 by the transfer roller 41. The transfer belt 40 is driven by the drive roller 30 to circulate in an arrow direction (i.e., clockwise). As the transfer belt 40 circulates, the paper P sucked onto the transfer belt 40 passes between the photosensitive members 1 and the corresponding transfer rollers 41 in order. As the paper P passes between the photosensitive members 1 and the corresponding transfer rollers 41, toner images of corresponding colors formed on the photosensitive members 1 are transferred onto the paper P in order such that the toner images are superposed on one another. After the above, the photosensitive members 1 continue to rotate and a next process is performed. Through the above, an explanation has been provided with reference to FIG. 5 for the image forming apparatus 6 according to the alternative example of the present embodiment in which the direct transfer process is adopted.

The image forming apparatus according to the present embodiment has been explained above with reference to FIGS. 4 and 5. The image forming apparatus according to the present embodiment includes the photosensitive member according to the second embodiment, which can inhibit transfer memory, as an image bearing member. By including the photosensitive member such as described above, the image forming apparatus according to the present embodiment can inhibit image defects from occurring.

[Examples]

The following provides more specific explanation of the present disclosure through use of Examples. However, it should be noted that the present disclosure is not limited to the scope of the Examples.

<1. Triarylamine Derivative Synthesis>

The triarylamine derivatives (HT-1) to (HT-10) were synthesized according to the following methods.

[Synthesis of Triarylamine Derivative (HT-1)]

The triarylamine derivative (HT-1) was synthesized according to the following reaction scheme. Specific explanation of the reaction scheme is provided below.

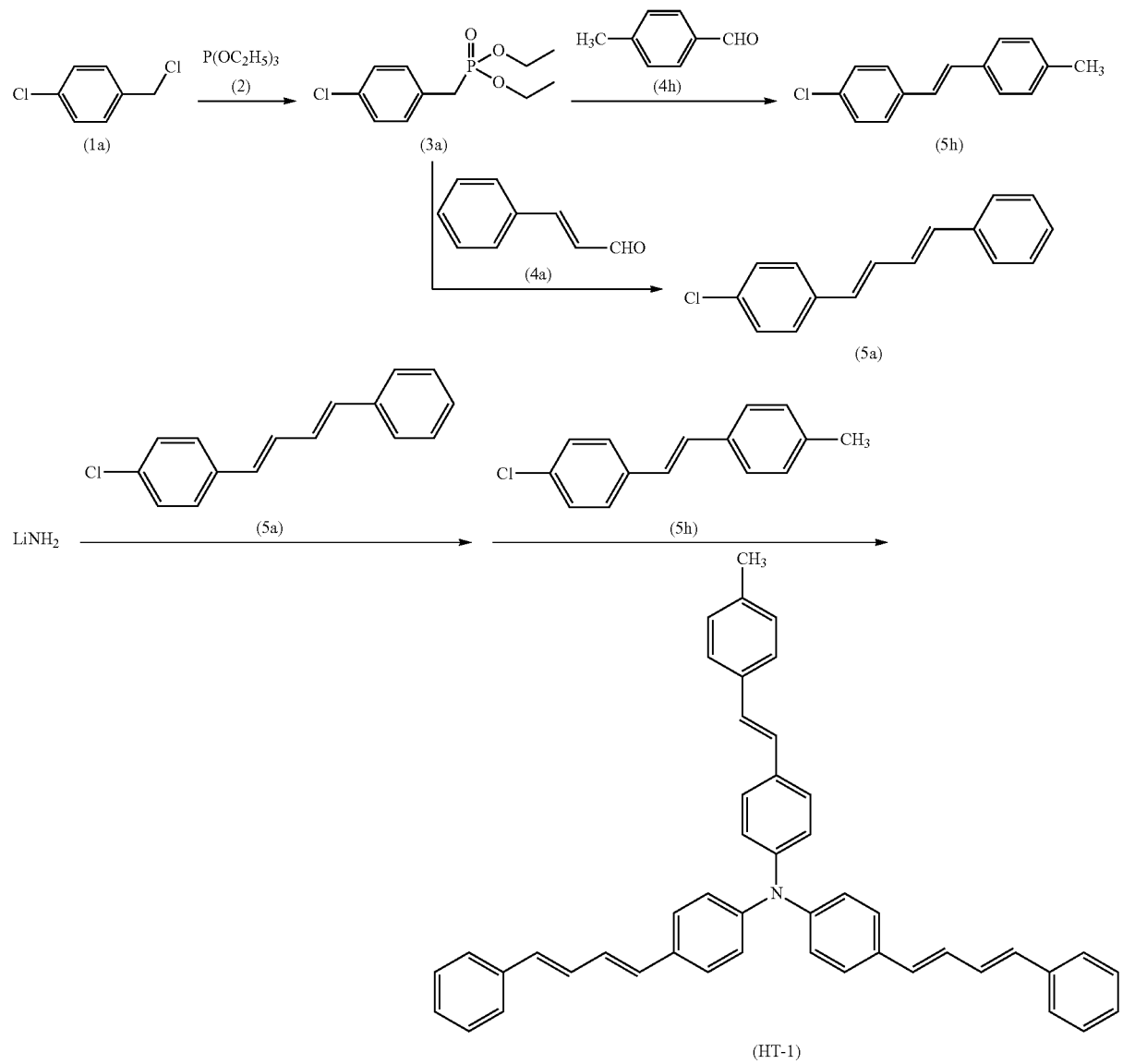

(Synthesis of Compound (3a))

Compound (1a) (16.1 g, 0.1 mol) and compound (2) (triethyl phosphite, 25 g, 0.15 mol) were added into a flask having a capacity of 200 mL, were stirred for 8 hours at 180° C., and were subsequently cooled to room temperature. Next, excess triethyl phosphite was evaporated under reduced pressure to yield compound (3a) (mass yield 24.1 g, percentage yield 92 mol %) as a white liquid.

(Synthesis of Compound (5a))

The resultant compound (3a) (13 g, 0.05 mol) was added at 0° C. into a two-necked flask having a capacity of 500 mL. Gas in the flask was displaced with argon gas. Next, dried tetrahydrofuran (100 mL) and 28% sodium methoxide (9.3 g, 0.05 mol) were added into the flask and the flask contents were stirred for 30 minutes. After stirring for 30 minutes, compound (4a) (7 g, 0.05 mol) in dried tetrahydrofuran (300 mL) was added into the flask and the flask contents were stirred for 12 hours at room temperature. After pouring the resultant mixture into ion exchanged water, extraction was performed using toluene. A resultant organic layer was washed five times using ion exchanged water. After drying the washed organic layer with anhydrous sodium sulfate, solvent evaporation was performed. The resultant residue was purified using toluene/methanol (20 mL/100 mL) to yield compound (5a) (mass yield 9.8 g, percentage yield 80 mol %) as white crystals.

(Synthesis of Compound (5h))

The resultant compound (3a) (13 g, 0.05 mol) was added at 0° C. into a two-necked flask having a capacity of 500 mL. Gas in the flask was displaced with argon gas. Next, dried tetrahydrofuran (100 mL) and 28% sodium methoxide (9.3 g, 0.05 mol) were added into the flask and the flask contents were stirred for 30 minutes. After stirring for 30 minutes, compound (4h) (5 g, 0.05 mol) in dried tetrahydrofuran (300 mL) was added into the flask and the flask contents were stirred for 12 hours at room temperature. After pouring the resultant mixture into ion exchanged water, extraction was performed using toluene. A resultant organic layer was washed five times using ion exchanged water. After drying the washed organic layer with anhydrous sodium sulfate, solvent evaporation was performed. The resultant residue was purified using toluene/methanol (20 mL/100 mL) to yield compound (5h) (mass yield 8.8 g, percentage yield 87 mol %) as white crystals.

(Synthesis of Intermediate Compound of Triarylamine Derivative (HT-1))

The resultant compound (5a) (6 g, 0.02 mol), tricyclohexylphosphine (0.0662 g, 0.000189 mol), tris(dibenzylideneacetone)dipalladium(0) (0.0864 g, 0.0000944 mol), sodium tert-butoxide (4 g, 0.42 mol), lithium amide (0.24 g, 0.010 mol), and distilled o-xylene (500 mL) were added into a three-necked flask. Gas in the flask was displaced with argon gas. Next, the flask contents were stirred for 5 hours at 120° C. and were subsequently cooled to room temperature. The resultant mixture was washed three times using ion exchanged water, thereby obtaining an organic layer. Anhydrous sodium sulfate and activated clay were added to the organic layer in order to perform drying treatment and adsorption treatment. Next, the resultant organic layer was subjected to reduced pressure evaporation in order to remove o-xylene. The resultant residue was crystallized using chloroform/hexane (volume ratio 1:1) to yield the intermediate compound (mass yield 2.6 g) of the triarylamine derivative (HT-1).

(Synthesis of Triarylamine Derivative (HT-1))

The resultant intermediate compound (2.6 g, 0.006 mol), the compound (5h) (1.5 g, 0.006 mol), tricyclohexylphosphine (0.20604 g, 5.887×10$^{-5}$ mol), tris(dibenzylideneacetone)dipalladium(0) (0.026933 g, 2.943×10$^{-5}$ mol), sodium tert-butoxide (1 g, 0.010 mol), and distilled o-xylene (200 mL) were added into a three-necked flask. Gas in the flask was displaced with argon gas. Next, the flask contents were stirred for 5 hours at 120° C. and were subsequently cooled to room temperature. The resultant mixture was washed three times using ion exchanged water, thereby obtaining an organic layer. Anhydrous sodium sulfate and activated clay were added to the organic layer in order to perform drying treatment and adsorption treatment. Next, the resultant organic layer was subjected to reduced pressure evaporation in order to remove o-xylene. The resultant residue was purified by silica gel column chromatography, using chloroform/hexane (volume ratio 1:1) as a developing solvent, to yield the triarylamine derivative (HT-1) (mass yield 3.8 g, percentage yield 63 mol %).

[Synthesis of Triarylamine Derivative (HT-2)]

Compound (5b) (percentage yield 85 mol %) shown below was synthesized according to the same method as the compound (5h) in all aspects other than that compound (4b) shown below was used instead of the compound (4h). Next, an intermediate compound was synthesized according to the same method as the intermediate compound of the triarylamine derivative (HT-1). The triarylamine derivative (HT-2) (percentage yield 65 mol %) was then synthesized according to the same method as the triarylamine derivative (HT-1) in all aspects other than that compound (5b) was used instead of the compound (5h).

The resultant triarylamine derivative (HT-2) was measured using a 300 MHz $^1$H-NMR (proton nuclear magnetic resonance) spectrometer. CDCl$_3$ was used as a solvent. A $^1$H-NMR spectrum of the triarylamine derivative (HT-2) is shown in FIG. 1. Chemical shifts for the $^1$H-NMR spectrum in FIG. 1 are shown below. The $^1$H-NMR spectrum and the chemical shifts were used to confirm that the triarylamine derivative (HT-2) had been obtained.

$^1$H-NMR δ=7.30-7.52 (m, 18H), 7.19-7.27 (m, 3H), 6.83-7.13 (m, 12H), 6.60-6.67 (m, 4H)

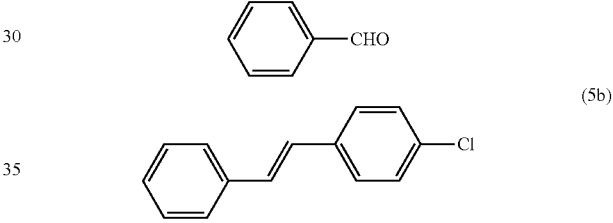

[Synthesis of Triarylamine Derivative (HT-3)]

Compound (5c) (percentage yield 40 mol %) shown below was synthesized according to the same method as the compound (5a) in all aspects other than that compound (3b) shown below was used instead of the compound (3a) and compound (4c) shown below was used instead of the compound (4a). Next, an intermediate compound was synthesized according to the same method as the intermediate compound of the triarylamine derivative (HT-1) in all aspects other that the compound (5c) was used instead of the compound (5a). The triarylamine derivative (HT-3) (percentage yield 55 mol %) was then synthesized according to the same method as the triarylamine derivative (HT-1) in all aspects other than that the compound (5a) was used instead of the compound (5h).

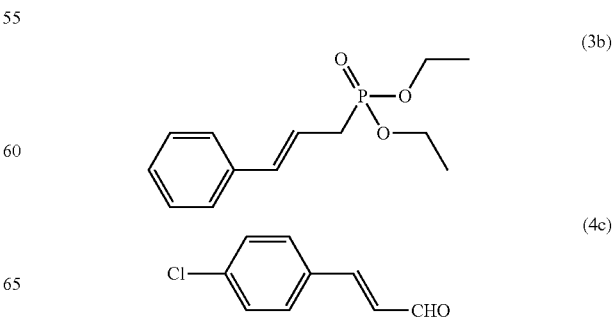

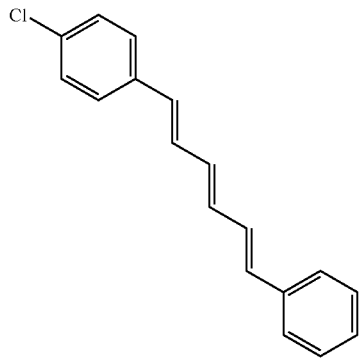

(5c)

[Synthesis of Triarylamine Derivative (HT-4)]

An intermediate compound was synthesized according to the same method as the intermediate compound of the triarylamine derivative (HT-1). The triarylamine derivative (HT-4) (percentage yield 55 mol %) was then synthesized according to the same method as the triarylamine derivative (HT-1) in all aspects other than that the compound (5c) was used instead of the compound (5h).

[Synthesis of Triarylamine Derivative (HT-5)]

An intermediate compound was synthesized according to the same method as the intermediate compound of the triarylamine derivative (HT-1) in all aspects other that the compound (5b) was used instead of the compound (5a). The triarylamine derivative (HT-5) (percentage yield 60 mol %) was then synthesized according to the same method as the triarylamine derivative (HT-1) in all aspects other than that the compound (5c) was used instead of the compound (5h).

[Synthesis of Triarylamine Derivative (HT-6)]

An intermediate compound was synthesized according to the same method as the intermediate compound of the triarylamine derivative (HT-1) in all aspects other that the compound (5b) was used instead of the compound (5a). The triarylamine derivative (HT-6) (percentage yield 70 mol %) was then synthesized according to the same method as the triarylamine derivative (HT-1) in all aspects other than that the compound (5a) was used instead of the compound (5h).

[Synthesis of Triarylamine Derivative (HT-7)]

An intermediate compound was synthesized according to the same method as the intermediate compound of the triarylamine derivative (HT-1) in all aspects other that the compound (5c) was used instead of the compound (5a). The triarylamine derivative (HT-7) (percentage yield 57 mol %) was then synthesized according to the same method as the triarylamine derivative (HT-1) in all aspects other than that the compound (5b) was used instead of the compound (5h).

[Synthesis of Triarylamine Derivative (HT-8)]

Compound (5g) (percentage yield 75 mol %) shown below was synthesized according to the same method as the compound (5a) in all aspects other than that compound (4g) shown below was used instead of the compound (4a). Next, an intermediate compound was synthesized according to the same method as the intermediate compound of the triarylamine derivative (HT-1) in all aspects other that the compound (5c) was used instead of the compound (5a). The triarylamine derivative (HT-8) (percentage yield 54 mol %) was then synthesized according to the same method as the triarylamine derivative (HT-1) in all aspects other than that the compound (5g) shown below was used instead of the compound (5h).

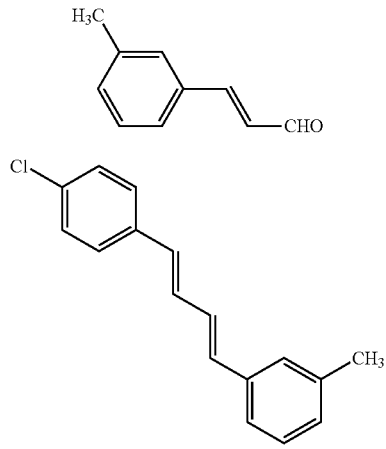

(4g)

(5g)

[Synthesis of Triarylamine Derivative (HT-9)]

Compound (5e) (percentage yield 70 mol %) shown below was synthesized in the same way as the compound (5a) in all aspects other than that compound (4e) shown below was used instead of the compound (4a). Next, an intermediate compound was synthesized according to the same method as the intermediate compound of the triarylamine derivative (HT-1) in all aspects other that the compound (5c) was used instead of the compound (5a). The triarylamine derivative (HT-9) (percentage yield 55 mol %) was then synthesized according to the same method as the triarylamine derivative (HT-1) in all aspects other than that the compound (5e) was used instead of the compound (5h).

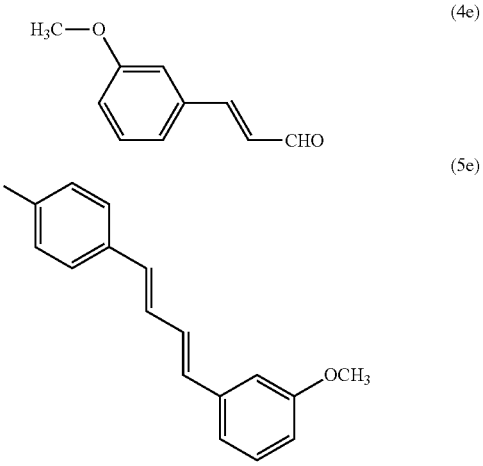

(4e)

(5e)

[Synthesis of Triarylamine Derivative (HT-10)]

Compound (5f) (percentage yield 65 mol %) shown below was synthesized according to the same method as the compound (5h) in all aspects other than that compound (4f) shown below was used instead of the compound (4h). Next, an intermediate compound was synthesized according to the same method as the intermediate compound of the triarylamine derivative (HT-1) in all aspects other that compound (5f) was used instead of the compound (5a). The triarylamine derivative (HT-10) (percentage yield 60 mol %) was then synthesized according to the same method as the triarylamine derivative (HT-1) in all aspects other than that the compound (5a) was used instead of the compound (5h).

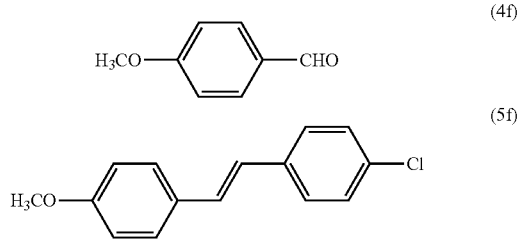

(4f)

(5f)

<2. Multi-Layer Photosensitive Member Production>

Multi-layer photosensitive members (A-1) to (A-10), (B-1), and (B-2) were produced according to the following methods.

[Multi-Layer Photosensitive Member (A-1)]
(Intermediate Layer Formation)

First, surface treated titanium oxide (test sample SMT-02 produced by Tayca Corporation, number average primary particle size 10 nm) was prepared. More specifically, titanium oxide was surface treated using alumina and silica. After being subjected to the above surface treatment, the titanium oxide was further surface treated using methyl hydrogen polysiloxane during wet dispersion. Next, the surface treated titanium oxide (2.8 parts by mass) and copolyamide resin (DAIAMID X4685 produced by Daicel-Evonik Ltd.) (1 part by mass) were added to a solvent including ethanol (10 parts by mass) and butanol (2 parts by mass). The above materials were then mixed for 5 hours using a bead mill. Through the mixing, the materials were dispersed in the solvent, thereby preparing an application liquid for intermediate layer formation.

Next, the resultant application liquid for intermediate layer formation was filtered using a filter having a pore size of 5 μm. After filtration, the application liquid for intermediate layer formation was applied onto the surface of a conductive substrate—an aluminum drum-shaped support (diameter 30 mm, total length 238.5 mm)—by dip coating. Next, the applied application liquid was dried for 30 minutes at 130° C., thereby forming an intermediate layer (film thickness 1.5 μm) on the conductive substrate (drum-shaped support).

(Charge Generating Layer Formation)

Y-form titanyl phthalocyanine (1 part by mass) as a charge generating material and polyvinyl butyral resin (Denka Butyral 6000EP produced by Denki Kagaku Kogyo Kabushiki Kaisha) (1 part by mass) as a base resin were added to a solvent including propylene glycol monomethyl ether (40 parts by mass) and tetrahydrofuran (40 parts by mass). Next, mixing was performed for 2 hours using a bead mill in order to disperse the materials in the solvent. Through the above process, a second application liquid was prepared. The obtained second application liquid was filtered using a filter having a pore size of 3 μm. After filtration, the resultant filtrate (second application liquid) was applied by dip coating onto the intermediate layer formed as described above and was dried for 5 minutes at 50° C. Through the above process, a charge generating layer (film thickness 0.3 μm) was formed on the intermediate layer.

(Charge Transport Layer Formation)

The triarylamine derivative (HT-1) (70 parts by mass) as a hole transport material, BHT (di(tert-butyl)p-cresol) (5 parts by mass) as an antioxidant, and Z-form polycarbonate resin (TS-2050 produced by Teijin Limited, viscosity average molecular weight 50,000) (100 parts by mass) as a binder resin were added to a solvent including tetrahydrofuran (430 parts by mass) and toluene (430 parts by mass). Mixing of the above materials was performed for 12 hours using a circulating ultrasonic disperser in order to disperse the components in the solvent. Through the above process, a third application liquid was prepared.

The third application liquid was applied through the same operation as the second application liquid onto the charge generating layer formed as described above. Next, the third application liquid was dried for 30 minutes at 130° C. to yield a charge transport layer (film thickness 20 μm) on the charge generating layer. The multi-layer photosensitive member (A-1) was obtained as a result of the process described above. In the multi-layer photosensitive member (A-1), the intermediate layer, the charge generating layer, and the charge transport layer were stacked in stated order on the conductive substrate.

[Multi-Layer Photosensitive Member (A-2)]

The multi-layer photosensitive member (A-2) was produced according to the same method as the multi-layer photosensitive member (A-1) in all aspects other than that the triarylamine derivative (HT-2) was used as the hole transport material instead of the triarylamine derivative (HT-1).

[Multi-Layer Photosensitive Member (A-3)]

The multi-layer photosensitive member (A-3) was produced according to the same method as the multi-layer photosensitive member (A-1) in all aspects other than that the triarylamine derivative (HT-3) was used as the hole transport material instead of the triarylamine derivative (HT-1).

[Multi-Layer Photosensitive Member (A-4)]

The multi-layer photosensitive member (A-4) was produced according to the same method as the multi-layer photosensitive member (A-1) in all aspects other than that the triarylamine derivative (HT-4) was used as the hole transport material instead of the triarylamine derivative (HT-1).

[Multi-Layer Photosensitive Member (A-5)]

The multi-layer photosensitive member (A-5) was produced according to the same method as the multi-layer photosensitive member (A-1) in all aspects other than that the triarylamine derivative (HT-5) was used as the hole transport material instead of the triarylamine derivative (HT-1).

[Multi-Layer Photosensitive Member (A-6)]

The multi-layer photosensitive member (A-6) was produced according to the same method as the multi-layer photosensitive member (A-1) in all aspects other than that the triarylamine derivative (HT-6) was used as the hole transport material instead of the triarylamine derivative (HT-1).

[Multi-Layer Photosensitive Member (A-7)]

The multi-layer photosensitive member (A-7) was produced according to the same method as the multi-layer photosensitive member (A-1) in all aspects other than that the triarylamine derivative (HT-7) was used as the hole transport material instead of the triarylamine derivative (HT-1).

[Multi-Layer Photosensitive Member (A-8)]

The multi-layer photosensitive member (A-8) was produced according to the same method as the multi-layer photosensitive member (A-1) in all aspects other than that the triarylamine derivative (HT-8) was used as the hole transport material instead of the triarylamine derivative (HT-1).

[Multi-Layer Photosensitive Member (A-9)]

The multi-layer photosensitive member (A-9) was produced according to the same method as the multi-layer photosensitive member (A-1) in all aspects other than that the triarylamine derivative (HT-9) was used as the hole transport material instead of the triarylamine derivative (HT-1).

[Multi-Layer Photosensitive Member (A-10)]

The multi-layer photosensitive member (A-10) was produced according to the same method as the multi-layer photosensitive member (A-1) in all aspects other than that the triarylamine derivative (HT-10) was used as the hole transport material instead of the triarylamine derivative (HT-1).

[Multi-Layer Photosensitive Member (B-1)]

The multi-layer photosensitive member (B-1) was produced according to the same method as the multi-layer photosensitive member (A-1) in all aspects other than that the triarylamine derivative (HT-A) shown below was used as the hole transport material instead of the triarylamine derivative (HT-1).

(HT-A)

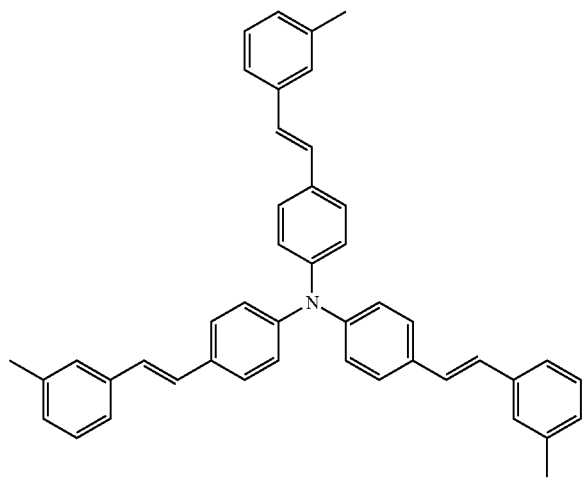

[Multi-Layer Photosensitive Member (B-2)]

The multi-layer photosensitive member (B-2) was produced according to the same method as the multi-layer photosensitive member (A-1) in all aspects other than that the triarylamine derivative (HT-B) shown below was used as the hole transport material instead of the triarylamine derivative (HT-1).

(HT-B)

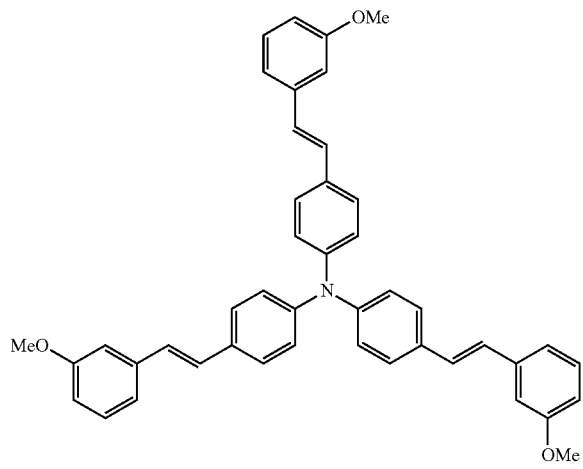

<3. Single-Layer Photosensitive Member Production>

Single-layer photosensitive members (C-1) to (C-30), (D-1) to (D-6), (E-1) to (E-41), and (F-1) to (F-8) were produced according to the following methods.

[Single-Layer Photosensitive Member (C-1)]

X-form metal-free phthalocyanine (5 parts by mass) as a charge generating material, the triarylamine derivative (HT-1) (80 parts by mass) as a hole transport material, a compound (ETM-1) (50 parts by mass) shown below as an electron transport material, polycarbonate resin (Z-form polycarbonate resin, Panlite (registered Japanese trademark) TS-2050 produced by Teijin Limited, viscosity average molecular weight 50,000) (100 parts by mass) as a binder resin, and tetrahydrofuran (800 parts by mass) as a solvent were added into a container. The container contents were mixed for 50 hours using a ball mill in order to disperse the materials in the solvent. Through the above process, an application liquid for single-layer type photosensitive layer formation (first application liquid) was prepared.

(ETM-1)

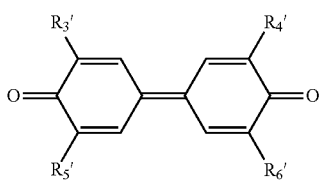

In the above chemical formula, $R_3'$ and $R_5'$ each represent a methyl group. $R_4'$ and $R_6'$ each represent a tert-butyl group.

Next, the prepared first application liquid was applied onto the surface of a conductive substrate—an aluminum drum-shaped support (diameter 30 mm, total length 238.5 mm)—by dip coating. Heat treatment (hot-air drying) was subsequently performed on the conductive substrate having the first application liquid applied thereon for 30 minutes at 100° C. Through the above, a single-layer type photosensitive layer (film thickness 25 μm) was formed. The single-layer photosensitive member (C-1) was obtained as a result of the above process.

[Single-Layer Photosensitive Member (C-2)]

The single-layer photosensitive member (C-2) was produced according to the same method as the single-layer photosensitive member (C-1) in all aspects other than that a compound (ETM-3) shown below was used as the electron transport material instead of the compound (ETM-1).

(ETM-3)

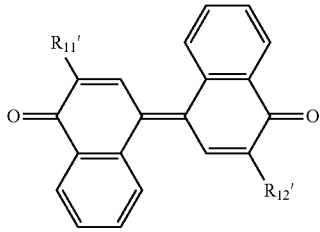

In the above chemical formula, $R_{11}'$ and $R_{12}'$ each represent a 1,1-dimethylpropyl group.

[Single-Layer Photosensitive Member (C-3)]

The single-layer photosensitive member (C-3) was produced according to the same method as the single-layer photosensitive member (C-1) in all aspects other than that Y-form titanyl phthalocyanine was used as the charge generating material instead of X-form metal-free phthalocyanine and the compound (ETM-3) was used as the electron transport material instead of the compound (ETM-1).

[Single-Layer Photosensitive Member (C-4)]

The single-layer photosensitive member (C-4) was produced according to the same method as the single-layer photosensitive member (C-1) in all aspects other than that the triarylamine derivative (HT-2) was used as the hole transport material instead of the triarylamine derivative (HT-1).

[Single-Layer Photosensitive Member (C-5)]

The single-layer photosensitive member (C-5) was produced according to the same method as the single-layer photosensitive member (C-1) in all aspects other than that the triarylamine derivative (HT-2) was used as the hole transport material instead of the triarylamine derivative (HT-1) and the compound (ETM-3) was used as the electron transport material instead of the compound (ETM-1).

[Single-Layer Photosensitive Member (C-6)]

The single-layer photosensitive member (C-6) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-2) was used as the hole transport material instead of the triarylamine derivative (HT-1). The compound (ETM-3) was used as the electron transport material instead of the compound (ETM-1).

[Single-Layer Photosensitive Member (C-7)]

The single-layer photosensitive member (C-7) was produced according to the same method as the single-layer photosensitive member (C-1) in all aspects other than that the triarylamine derivative (HT-3) was used as the hole transport material instead of the triarylamine derivative (HT-1).

[Single-Layer Photosensitive Member (C-8)]

The single-layer photosensitive member (C-8) was produced according to the same method as the single-layer photosensitive member (C-1) in all aspects other than that the triarylamine derivative (HT-3) was used as the hole transport material instead of the triarylamine derivative (HT-1) and the compound (ETM-3) was used as the electron transport material instead of the compound (ETM-1).

[Single-Layer Photosensitive Member (C-9)]

The single-layer photosensitive member (C-9) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-3) was used as the hole transport material instead of the triarylamine derivative (HT-1). The compound (ETM-3) was used as the electron transport material instead of the compound (ETM-1).

[Single-Layer Photosensitive Member (C-10)]

The single-layer photosensitive member (C-10) was produced according to the same method as the single-layer photosensitive member (C-1) in all aspects other than that the triarylamine derivative (HT-4) was used as the hole transport material instead of the triarylamine derivative (HT-1).

[Single-Layer Photosensitive Member (C-11)]

The single-layer photosensitive member (C-11) was produced according to the same method as the single-layer photosensitive member (C-1) in all aspects other than that the triarylamine derivative (HT-4) was used as the hole transport material instead of the triarylamine derivative (HT-1) and the compound (ETM-3) was used as the electron transport material instead of the compound (ETM-1).

[Single-Layer Photosensitive Member (C-12)]

The single-layer photosensitive member (C-12) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-4) was used as the hole transport material instead of the triarylamine derivative (HT-1). The compound (ETM-3) was used as the electron transport material instead of the compound (ETM-1).

[Single-Layer Photosensitive Member (C-13)]

The single-layer photosensitive member (C-13) was produced according to the same method as the single-layer photosensitive member (C-1) in all aspects other than that the triarylamine derivative (HT-5) was used as the hole transport material instead of the triarylamine derivative (HT-1).

[Single-Layer Photosensitive Member (C-14)]

The single-layer photosensitive member (C-14) was produced according to the same method as the single-layer photosensitive member (C-1) in all aspects other than that the triarylamine derivative (HT-5) was used as the hole transport material instead of the triarylamine derivative (HT-1) and the compound (ETM-3) was used as the electron transport material instead of the compound (ETM-1).

[Single-Layer Photosensitive Member (C-15)]

The single-layer photosensitive member (C-15) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-5) was used as the hole transport material instead of the triarylamine derivative (HT-1). The compound (ETM-3) was used as the electron transport material instead of the compound (ETM-1).

[Single-Layer Photosensitive Member (C-16)]

The single-layer photosensitive member (C-16) was produced according to the same method as the single-layer photosensitive member (C-1) in all aspects other than that the triarylamine derivative (HT-6) was used as the hole transport material instead of the triarylamine derivative (HT-1).

[Single-Layer Photosensitive Member (C-17)]

The single-layer photosensitive member (C-17) was produced according to the same method as the single-layer photosensitive member (C-1) in all aspects other than that the triarylamine derivative (HT-6) was used as the hole transport material instead of the triarylamine derivative (HT-1) and the compound (ETM-3) was used as the electron transport material instead of the compound (ETM-1).

[Single-Layer Photosensitive Member (C-18)]

The single-layer photosensitive member (C-18) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-6) was used as the hole transport material instead of the triarylamine derivative (HT-1). The compound (ETM-3) was used as the electron transport material instead of the compound (ETM-1).

[Single-Layer Photosensitive Member (C-19)]

The single-layer photosensitive member (C-19) was produced according to the same method as the single-layer photosensitive member (C-1) in all aspects other than that the triarylamine derivative (HT-7) was used as the hole transport material instead of the triarylamine derivative (HT-1).

[Single-Layer Photosensitive Member (C-20)]

The single-layer photosensitive member (C-20) was produced according to the same method as the single-layer photosensitive member (C-1) in all aspects other than that the triarylamine derivative (HT-7) was used as the hole transport material instead of the triarylamine derivative (HT-1) and the compound (ETM-3) was used as the electron transport material instead of the compound (ETM-1).

[Single-Layer Photosensitive Member (C-21)]

The single-layer photosensitive member (C-21) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-7) was used as the hole transport material instead of the triarylamine derivative (HT-1). The compound (ETM-3) was used as the electron transport material instead of the compound (ETM-1).

[Single-Layer Photosensitive Member (C-22)]

The single-layer photosensitive member (C-22) was produced according to the same method as the single-layer photosensitive member (C-1) in all aspects other than that the triarylamine derivative (HT-8) was used as the hole transport material instead of the triarylamine derivative (HT-1).

[Single-Layer Photosensitive Member (C-23)]

The single-layer photosensitive member (C-23) was produced according to the same method as the single-layer photosensitive member (C-1) in all aspects other than that the triarylamine derivative (HT-8) was used as the hole transport material instead of the triarylamine derivative (HT-1) and the compound (ETM-3) was used as the electron transport material instead of the compound (ETM-1).

[Single-Layer Photosensitive Member (C-24)]

The single-layer photosensitive member (C-24) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-8) was used as the hole transport material instead of the triarylamine derivative (HT-1). The compound (ETM-3) was used as the electron transport material instead of the compound (ETM-1).

[Single-Layer Photosensitive Member (C-25)]

The single-layer photosensitive member (C-25) was produced according to the same method as the single-layer photosensitive member (C-1) in all aspects other than that the triarylamine derivative (HT-9) was used as the hole transport material instead of the triarylamine derivative (HT-1).

[Single-Layer Photosensitive Member (C-26)]

The single-layer photosensitive member (C-26) was produced according to the same method as the single-layer photosensitive member (C-1) in all aspects other than that the triarylamine derivative (HT-9) was used as the hole transport material instead of the triarylamine derivative (HT-1) and the compound (ETM-3) was used as the electron transport material instead of the compound (ETM-1).

[Single-Layer Photosensitive Member (C-27)]

The single-layer photosensitive member (C-27) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-9) was used as the hole transport material instead of the triarylamine derivative (HT-1). The compound (ETM-3) was used as the electron transport material instead of the compound (ETM-1).

[Single-Layer Photosensitive Member (C-28)]

The single-layer photosensitive member (C-28) was produced according to the same method as the single-layer photosensitive member (C-1) in all aspects other than that the triarylamine derivative (HT-10) was used as the hole transport material instead of the triarylamine derivative (HT-1).

[Single-Layer Photosensitive Member (C-29)]

The single-layer photosensitive member (C-29) was produced according to the same method as the single-layer photosensitive member (C-1) in all aspects other than that the triarylamine derivative (HT-10) was used as the hole transport material instead of the triarylamine derivative (HT-1) and the compound (ETM-3) was used as the electron transport material instead of the compound (ETM-1).

[Single-Layer Photosensitive Member (C-30)]

The single-layer photosensitive member (C-30) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-10) was used as the hole transport material instead of the triarylamine derivative (HT-1). The compound (ETM-3) was used as the electron transport material instead of the compound (ETM-1).

[Single-Layer Photosensitive Member (D-1)]

The single-layer photosensitive member (D-1) was produced according to the same method as the single-layer photosensitive member (C-1) in all aspects other than that the triarylamine derivative (HT-A) was used as the hole transport material instead of the triarylamine derivative (HT-1).

[Single-Layer Photosensitive Member (D-2)]

The single-layer photosensitive member (D-2) was produced according to the same method as the single-layer photosensitive member (C-1) in all aspects other than that the triarylamine derivative (HT-A) was used as the hole transport material instead of the triarylamine derivative (HT-1) and the compound (ETM-3) was used as the electron transport material instead of the compound (ETM-1).

[Single-Layer Photosensitive Member (D-3)]

The single-layer photosensitive member (D-3) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-A) was used as the hole transport material instead of the triarylamine derivative (HT-1). The compound (ETM-3) was used as the electron transport material instead of the compound (ETM-1).

[Single-Layer Photosensitive Member (D-4)]

The single-layer photosensitive member (D-4) was produced according to the same method as the single-layer photosensitive member (C-1) in all aspects other than that the triarylamine derivative (HT-B) was used as the hole transport material instead of the triarylamine derivative (HT-1).

[Single-Layer Photosensitive Member (D-5)]

The single-layer photosensitive member (D-5) was produced according to the same method as the single-layer photosensitive member (C-1) in all aspects other than that the triarylamine derivative (HT-B) was used as the hole transport material instead of the triarylamine derivative (HT-1) and the compound (ETM-3) was used as the electron transport material instead of the compound (ETM-1).

[Single-Layer Photosensitive Member (D-6)]

The single-layer photosensitive member (D-6) was produced according to the same method as the single-layer photosensitive member (C-1) in all aspects other than the changes described below. Y-form titanyl phthalocyanine was used as the charge generating material instead of X-form metal-free phthalocyanine. The triarylamine derivative (HT-B) was used as the hole transport material instead of the triarylamine derivative (HT-1). The compound (ETM-3) was used as the electron transport material instead of the compound (ETM-1).

[Single-Layer Photosensitive Member (E-1)]

X-form metal-free phthalocyanine (5 parts by mass) as a charge generating material, the triarylamine derivative (HT-1) (50 parts by mass) as a hole transport material, an electron transport material (35 parts by mass) shown below, a binder resin (100 parts by mass) shown below, and tetrahydrofuran (800 parts by mass) as a solvent were added into a container. The container contents were mixed for 50 hours using a ball mill in order to disperse the materials in the solvent and thereby obtain an application liquid for single-layer type photosensitive layer formation (first application liquid). A compound represented by chemical formula (ETM-1) shown below (also referred to below as compound (ETM-1)) was used as the electron transport material. In chemical formula (ETM-1), $R_3'$ and $R_5'$ each represent a methyl group. $R_4'$ and $R_6'$ each represent a tert-butyl group.

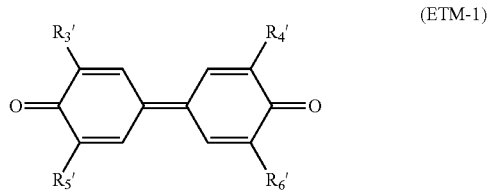

(ETM-1)

A resin (viscosity average molecular weight 50,000) represented by the chemical formula shown below was used as the binder resin. Note that the number attached to the repeating unit in the following chemical formula indicates the molar ratio (mol %) of the repeating unit relative to the total number of moles of repeating units included in the resin.

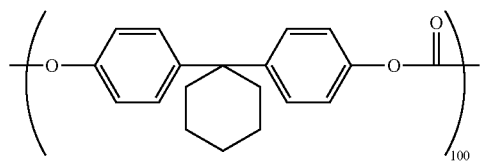

Next, the obtained first application liquid was applied onto the surface of a conductive substrate—an aluminum drum-shaped support (diameter 30 mm, total length 238.5 mm)—by dip coating. Heat treatment (hot-air drying) was subsequently performed on the conductive substrate having the first application liquid applied thereon for 40 minutes at 100° C. to form a single-layer type photosensitive layer (film thickness 30 μm). The single-layer photosensitive member (E-1) was obtained as a result of the above process.

[Single-Layer Photosensitive Member (E-2)]

The single-layer photosensitive member (E-2) was produced according to the same method as the single-layer photosensitive member (E-1) in all aspects other than that a compound represented by chemical formula (ETM-2) shown below (also referred to below as compound (ETM-2)) was used instead of the compound (ETM-1).

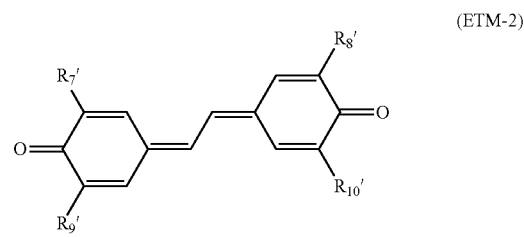

(ETM-2)

In the above chemical formula (ETM-2), $R_7'$ represents a methyl group. $R_8'$ represents a methyl group. $R_9'$ represents a tert-butyl group. $R_{10}'$ represents a tert-butyl group.

[Single-Layer Photosensitive Member (E-3)]

The single-layer photosensitive member (E-3) was produced according to the same method as the single-layer photosensitive member (E-1) in all aspects other than that a compound represented by chemical formula (ETM-3) shown below (also referred to below as compound (ETM-3)) was used instead of the compound (ETM-1).

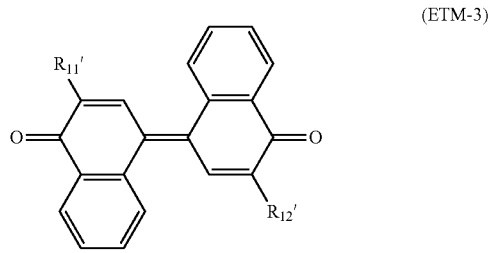

(ETM-3)

In the above chemical formula, $R_{11}'$ and $R_{12}'$ each represent a 1,1-dimethylpropyl group.

[Single-Layer Photosensitive Member (E-4)]

The single-layer photosensitive member (E-4) was produced according to the same method as the single-layer photosensitive member (E-1) in all aspects other than that a compound represented by chemical formula (ETM-4) shown below (also referred to below as compound (ETM-4)) was used instead of the compound (ETM-1).

(ETM-4)

[Chemical structure diagram showing ETM-4 with substituents $R_{13}'$, $R_{14}'$, and $R_{15}'$]

In the above chemical formula, $R_{13}'$ represents a tert-butyl group. $R_{14}'$ represents a tert-butyl group. $R_{15}'$ represents a chlorine atom at a para position relative to the nitrogen atom.

[Single-Layer Photosensitive Member (E-5)]

The single-layer photosensitive member (E-5) was produced according to the same method as the single-layer photosensitive member (E-1) in all aspects other than that the triarylamine derivative (HT-2) was used as the hole transport material instead of the triarylamine derivative (HT-1).

[Single-Layer Photosensitive Member (E-6)]

The single-layer photosensitive member (E-6) was produced according to the same method as the single-layer photosensitive member (E-1) in all aspects other than that the triarylamine derivative (HT-2) was used as the hole transport material instead of the triarylamine derivative (HT-1) and the compound (ETM-2) was used instead of the compound (ETM-1).

[Single-Layer Photosensitive Member (E-7)]

The single-layer photosensitive member (E-7) was produced according to the same method as the single-layer photosensitive member (E-1) in all aspects other than that the triarylamine derivative (HT-2) was used as the hole transport material instead of the triarylamine derivative (HT-1) and the compound (ETM-3) was used instead of the compound (ETM-1).

[Single-Layer Photosensitive Member (E-8)]

The single-layer photosensitive member (E-8) was produced according to the same method as the single-layer photosensitive member (E-1) in all aspects other than that the triarylamine derivative (HT-2) was used as the hole transport material instead of the triarylamine derivative (HT-1) and the compound (ETM-4) was used instead of the compound (ETM-1).

[Single-Layer Photosensitive Member (E-9)]

The single-layer photosensitive member (E-9) was produced according to the same method as the single-layer photosensitive member (E-1) in all aspects other than that the triarylamine derivative (HT-3) was used as the hole transport material instead of the triarylamine derivative (HT-1).

[Single-Layer Photosensitive Member (E-10)]

The single-layer photosensitive member (E-10) was produced according to the same method as the single-layer photosensitive member (E-1) in all aspects other than that the triarylamine derivative (HT-3) was used as the hole transport material instead of the triarylamine derivative (HT-1) and the compound (ETM-2) was used instead of the compound (ETM-1).

[Single-Layer Photosensitive Member (E-11)]

The single-layer photosensitive member (E-11) was produced according to the same method as the single-layer photosensitive member (E-1) in all aspects other than that the triarylamine derivative (HT-3) was used as the hole transport material instead of the triarylamine derivative (HT-1) and the compound (ETM-3) was used instead of the compound (ETM-1).

[Single-Layer Photosensitive Member (E-12)]

The single-layer photosensitive member (E-12) was produced according to the same method as the single-layer photosensitive member (E-1) in all aspects other than that the triarylamine derivative (HT-3) was used as the hole transport material instead of the triarylamine derivative (HT-1) and the compound (ETM-4) was used instead of the compound (ETM-1).

[Single-Layer Photosensitive Member (E-13)]

The single-layer photosensitive member (E-13) was produced according to the same method as the single-layer photosensitive member (E-1) in all aspects other than that the triarylamine derivative (HT-4) was used as the hole transport material instead of the triarylamine derivative (HT-1).

[Single-Layer Photosensitive Member (E-14)]

The single-layer photosensitive member (E-14) was produced according to the same method as the single-layer photosensitive member (E-1) in all aspects other than that the triarylamine derivative (HT-4) was used as the hole transport material instead of the triarylamine derivative (HT-1) and the compound (ETM-2) was used instead of the compound (ETM-1).

[Single-Layer Photosensitive Member (E-15)]

The single-layer photosensitive member (E-15) was produced according to the same method as the single-layer photosensitive member (E-1) in all aspects other than that the triarylamine derivative (HT-4) was used as the hole transport material instead of the triarylamine derivative (HT-1) and the compound (ETM-3) was used instead of the compound (ETM-1).

[Single-Layer Photosensitive Member (E-16)]

The single-layer photosensitive member (E-16) was produced according to the same method as the single-layer photosensitive member (E-1) in all aspects other than that the triarylamine derivative (HT-4) was used as the hole transport material instead of the triarylamine derivative (HT-1) and the compound (ETM-4) was used instead of the compound (ETM-1).

[Single-Layer Photosensitive Member (E-17)]

The single-layer photosensitive member (E-17) was produced according to the same method as the single-layer photosensitive member (E-1) in all aspects other than that the triarylamine derivative (HT-5) was used as the hole transport material instead of the triarylamine derivative (HT-1).

[Single-Layer Photosensitive Member (E-18)]

The single-layer photosensitive member (E-18) was produced according to the same method as the single-layer photosensitive member (E-1) in all aspects other than that the triarylamine derivative (HT-5) was used as the hole transport material instead of the triarylamine derivative (HT-1) and the compound (ETM-2) was used instead of the compound (ETM-1).

[Single-Layer Photosensitive Member (E-19)]

The single-layer photosensitive member (E-19) was produced according to the same method as the single-layer photosensitive member (E-1) in all aspects other than that the triarylamine derivative (HT-5) was used as the hole transport material instead of the triarylamine derivative (HT-1) and the compound (ETM-3) was used instead of the compound (ETM-1).

[Single-Layer Photosensitive Member (E-20)]

The single-layer photosensitive member (E-20) was produced according to the same method as the single-layer photosensitive member (E-1) in all aspects other than that the triarylamine derivative (HT-5) was used as the hole transport material instead of the triarylamine derivative (HT-1) and the compound (ETM-4) was used instead of the compound (ETM-1).

[Single-Layer Photosensitive Member (E-21)]

The single-layer photosensitive member (E-21) was produced according to the same method as the single-layer photosensitive member (E-1) in all aspects other than that the triarylamine derivative (HT-6) was used as the hole transport material instead of the triarylamine derivative (HT-1).

[Single-Layer Photosensitive Member (E-22)]

The single-layer photosensitive member (E-22) was produced according to the same method as the single-layer photosensitive member (E-1) in all aspects other than that the triarylamine derivative (HT-6) was used as the hole transport material instead of the triarylamine derivative (HT-1) and the compound (ETM-2) was used instead of the compound (ETM-1).

[Single-Layer Photosensitive Member (E-23)]

The single-layer photosensitive member (E-23) was produced according to the same method as the single-layer photosensitive member (E-1) in all aspects other than that the triarylamine derivative (HT-6) was used as the hole transport material instead of the triarylamine derivative (HT-1) and the compound (ETM-3) was used instead of the compound (ETM-1).

[Single-Layer Photosensitive Member (E-24)]

The single-layer photosensitive member (E-24) was produced according to the same method as the single-layer photosensitive member (E-1) in all aspects other than that the triarylamine derivative (HT-6) was used as the hole transport material instead of the triarylamine derivative (HT-1) and the compound (ETM-4) was used instead of the compound (ETM-1).

[Single-Layer Photosensitive Member (E-25)]

The single-layer photosensitive member (E-25) was produced according to the same method as the single-layer photosensitive member (E-1) in all aspects other than that the triarylamine derivative (HT-7) was used as the hole transport material instead of the triarylamine derivative (HT-1).

[Single-Layer Photosensitive Member (E-26)]

The single-layer photosensitive member (E-26) was produced according to the same method as the single-layer photosensitive member (E-1) in all aspects other than that the triarylamine derivative (HT-7) was used as the hole transport material instead of the triarylamine derivative (HT-1) and the compound (ETM-2) was used instead of the compound (ETM-1).

[Single-Layer Photosensitive Member (E-27)]

The single-layer photosensitive member (E-27) was produced according to the same method as the single-layer photosensitive member (E-1) in all aspects other than that the triarylamine derivative (HT-7) was used as the hole transport material instead of the triarylamine derivative (HT-1) and the compound (ETM-3) was used instead of the compound (ETM-1).

[Single-Layer Photosensitive Member (E-28)]

The single-layer photosensitive member (E-28) was produced according to the same method as the single-layer photosensitive member (E-1) in all aspects other than that the triarylamine derivative (HT-7) was used as the hole transport material instead of the triarylamine derivative (HT-1) and the compound (ETM-4) was used instead of the compound (ETM-1).

[Single-Layer Photosensitive Member (E-29)]

The single-layer photosensitive member (E-29) was produced according to the same method as the single-layer photosensitive member (E-1) in all aspects other than that the triarylamine derivative (HT-8) was used as the hole transport material instead of the triarylamine derivative (HT-1).

[Single-Layer Photosensitive Member (E-30)]

The single-layer photosensitive member (E-30) was produced according to the same method as the single-layer photosensitive member (E-1) in all aspects other than that the triarylamine derivative (HT-8) was used as the hole transport material instead of the triarylamine derivative (HT-1) and the compound (ETM-2) was used instead of the compound (ETM-1).

[Single-Layer Photosensitive Member (E-31)]

The single-layer photosensitive member (E-31) was produced according to the same method as the single-layer photosensitive member (E-1) in all aspects other than that the triarylamine derivative (HT-8) was used as the hole transport material instead of the triarylamine derivative (HT-1) and the compound (ETM-3) was used instead of the compound (ETM-1).

[Single-Layer Photosensitive Member (E-32)]

The single-layer photosensitive member (E-32) was produced according to the same method as the single-layer photosensitive member (E-1) in all aspects other than that the triarylamine derivative (HT-8) was used as the hole transport material instead of the triarylamine derivative (HT-1) and the compound (ETM-4) was used instead of the compound (ETM-1).

[Single-Layer Photosensitive Member (E-33)]

The single-layer photosensitive member (E-33) was produced according to the same method as the single-layer photosensitive member (E-1) in all aspects other than that the triarylamine derivative (HT-9) was used as the hole transport material instead of the triarylamine derivative (HT-1).

[Single-Layer Photosensitive Member (E-34)]

The single-layer photosensitive member (E-34) was produced according to the same method as the single-layer photosensitive member (E-1) in all aspects other than that the triarylamine derivative (HT-9) was used as the hole transport material instead of the triarylamine derivative (HT-1) and the compound (ETM-2) was used instead of the compound (ETM-1).

[Single-Layer Photosensitive Member (E-35)]

The single-layer photosensitive member (E-35) was produced according to the same method as the single-layer photosensitive member (E-1) in all aspects other than that the triarylamine derivative (HT-9) was used as the hole transport material instead of the triarylamine derivative (HT-1) and the compound (ETM-3) was used instead of the compound (ETM-1).

[Single-Layer Photosensitive Member (E-36)]

The single-layer photosensitive member (E-36) was produced according to the same method as the single-layer photosensitive member (E-1) in all aspects other than that the triarylamine derivative (HT-9) was used as the hole transport material instead of the triarylamine derivative (HT-1) and the compound (ETM-4) was used instead of the compound (ETM-1).

[Single-Layer Photosensitive Member (E-37)]

The single-layer photosensitive member (E-37) was produced according to the same method as the single-layer photosensitive member (E-1) in all aspects other than that the triarylamine derivative (HT-10) was used as the hole transport material instead of the triarylamine derivative (HT-1).

[Single-Layer Photosensitive Member (E-38)]

The single-layer photosensitive member (E-38) was produced according to the same method as the single-layer photosensitive member (E-1) in all aspects other than that the triarylamine derivative (HT-10) was used as the hole transport material instead of the triarylamine derivative (HT-1) and the compound (ETM-2) was used instead of the compound (ETM-1).

[Single-Layer Photosensitive Member (E-39)]

The single-layer photosensitive member (E-39) was produced according to the same method as the single-layer photosensitive member (E-1) in all aspects other than that the triarylamine derivative (HT-10) was used as the hole transport material instead of the triarylamine derivative (HT-1) and the compound (ETM-3) was used instead of the compound (ETM-1).

[Single-Layer Photosensitive Member (E-40)]

The single-layer photosensitive member (E-40) was produced according to the same method as the single-layer photosensitive member (E-1) in all aspects other than that the triarylamine derivative (HT-10) was used as the hole transport material instead of the triarylamine derivative (HT-1) and the compound (ETM-4) was used instead of the compound (ETM-1).

[Single-Layer Photosensitive Member (E-41)]

The single-layer photosensitive member (E-41) was produced according to the same method as the single-layer photosensitive member (E-1) in all aspects other than that Y-form titanyl phthalocyanine was used as the charge generating material instead of X-form metal-free phthalocyanine.

[Single-Layer Photosensitive Member (F-1)]

The single-layer photosensitive member (F-1) was produced according to the same method as the single-layer photosensitive member (E-1) in all aspects other than that the triarylamine derivative (HT-A) shown below was used as the hole transport material instead of the triarylamine derivative (HT-1).

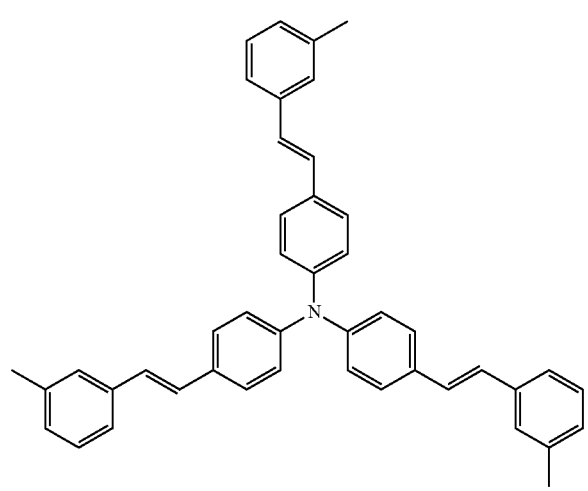

(HT-A)

[Single-Layer Photosensitive Member (F-2)]

The single-layer photosensitive member (F-2) was produced according to the same method as the single-layer photosensitive member (E-1) in all aspects other than that the triarylamine derivative (HT-A) was used as the hole transport material instead of the triarylamine derivative (HT-1) and the compound (ETM-2) was used instead of the compound (ETM-1).

[Single-Layer Photosensitive Member (F-3)]

The single-layer photosensitive member (F-3) was produced according to the same method as the single-layer photosensitive member (E-1) in all aspects other than that the triarylamine derivative (HT-A) was used as the hole transport material instead of the triarylamine derivative (HT-1) and the compound (ETM-3) was used instead of the compound (ETM-1).

[Single-Layer Photosensitive Member (F-4)]

The single-layer photosensitive member (F-4) was produced according to the same method as the single-layer photosensitive member (E-1) in all aspects other than that the triarylamine derivative (HT-A) was used as the hole transport material instead of the triarylamine derivative (HT-1) and the compound (ETM-4) was used instead of the compound (ETM-1).

[Single-Layer Photosensitive Member (F-5)]

The single-layer photosensitive member (F-5) was produced according to the same method as the single-layer photosensitive member (E-1) in all aspects other than that the triarylamine derivative (HT-B) shown below was used as the hole transport material instead of the triarylamine derivative (HT-1).

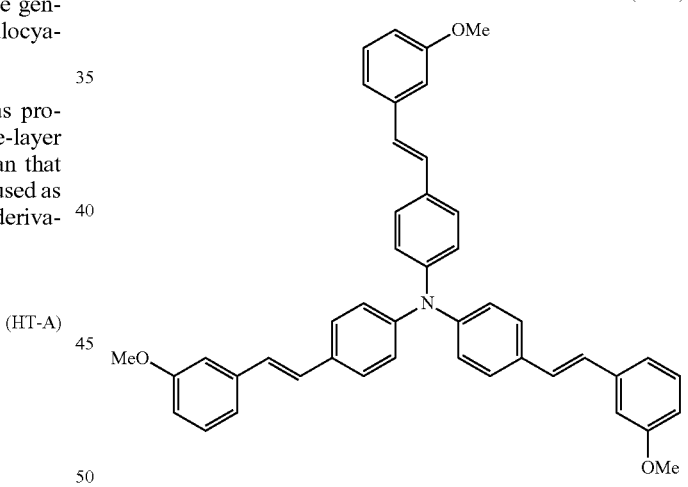

(HT-B)

[Single-Layer Photosensitive Member (F-6)]

The single-layer photosensitive member (F-6) was produced according to the same method as the single-layer photosensitive member (E-1) in all aspects other than that the triarylamine derivative (HT-B) was used as the hole transport material instead of the triarylamine derivative (HT-1) and the compound (ETM-2) was used instead of the compound (ETM-1).

[Single-Layer Photosensitive Member (F-7)]

The single-layer photosensitive member (F-7) was produced according to the same method as the single-layer photosensitive member (E-1) in all aspects other than that the triarylamine derivative (HT-B) was used as the hole transport material instead of the triarylamine derivative (HT-1) and the compound (ETM-3) was used instead of the compound (ETM-1).

[Single-Layer Photosensitive Member (F-8)]

The single-layer photosensitive member (F-8) was produced according to the same method as the single-layer photosensitive member (E-1) in all aspects other than that the triarylamine derivative (HT-B) was used as the hole transport material instead of the triarylamine derivative (HT-1) and the compound (ETM-4) was used instead of the compound (ETM-1).

<4. Evaluation of Multi-Layer Photosensitive Member Electrical Properties>

With respect to each of the multi-layer photosensitive members (A-1) to (A-10), (B-1), and (B-2), the multi-layer photosensitive member was charged to −700 V at a rotation rate of 31 rpm, using a drum sensitivity test device (product of Gen-Tech, Inc.). The surface potential of the multi-layer photosensitive member was measured after charging. The measured surface potential of the multi-layer photosensitive member was taken to be an initial surface potential ($V_0$, units: −V). Next, a band pass filter was used to obtain monochromatic light (wavelength 780 nm, half-width 20 nm, light energy 0.4 μJ/cm$^2$) from light emitted by a halogen lamp. The obtained monochromatic light was irradiated onto the surface of the multi-layer photosensitive member. The surface potential of the multi-layer photosensitive member was measured once 0.5 seconds had elapsed after completion of the irradiation. The measured surface potential of the multi-layer photosensitive member was taken to be a residual potential ($V_L$, units: −V). Measurement was performed under ambient conditions of 23° C. and 50% relative humidity. Initial surface potentials ($V_0$) and residual potentials ($V_L$) that were measured are shown in Table 1. It should be noted that a residual potential ($V_L$) having a smaller absolute value indicates better electrical properties.

<5. Evaluation of Single-Layer Photosensitive Member Electrical Properties>

With respect to each of the single-layer photosensitive members (C-1) to (C-30) and (D-1) to (D-6), the single-layer photosensitive member was charged to +700 V using the drum sensitivity test device (product of Gen-Tech, Inc.). The surface potential of the single-layer photosensitive member was measured after charging. The measured surface potential of the single-layer photosensitive member was taken to be an initial surface potential ($V_0$, units: +V). Next, a band pass filter was used to obtain monochromatic light (wavelength 780 nm, half-width 20 nm, light energy 1.5 μJ/cm$^2$) from light emitted by a halogen lamp. The obtained monochromatic light was irradiated onto the surface of the single-layer photosensitive member. The surface potential of the single-layer photosensitive member was measured once 0.5 seconds had elapsed after completion of the irradiation. The measured surface potential of the single-layer photosensitive member was taken to be a residual potential ($V_L$, units: +V). Measurement was performed under ambient conditions of 23° C. and 50% relative humidity. Initial surface potentials ($V_0$) and residual potentials ($V_L$) that were measured are shown in Table 2. It should be noted that a residual potential ($V_L$) having a smaller absolute value indicates better electrical properties.

<6. Measurement of Transfer Memory Potential>

With respect to each of the single-layer photosensitive members (E-1) to (E-41) and (F-1) to (F-8), the single-layer photosensitive member was installed in a color printer (FS-C5250DN produced by KYOCERA Document Solutions Inc.). Conditions were set such that the single-layer photosensitive member had a surface potential of +600 V. The single-layer photosensitive member was charged by applying a direct current voltage to a charging roller that was used as a charging device. The charging roller that applied the direct current voltage was a charging section of the printer. The charging roller was a roller formed from chargeable rubber (a roller formed from a material of conductive carbon dispersed in epichlorohydrin resin). Transfer was performed by an intermediate transfer process. More specifically, a transfer process was adopted in which a toner image on the single-layer photosensitive member was transferred onto an intermediate transfer belt and the toner image was subsequently transferred onto a paper medium.

The color printer was used to measure a surface potential ($V_{OFF}$) of a non-exposed portion (blank paper portion) of the single-layer photosensitive member in a situation in which a transfer bias was not applied to the single-layer photosensitive member (i.e., prior to transfer bias application). Next, a surface potential ($V_{ON}$) of the non-exposed portion (blank paper portion) was measured in a situation in which the transfer bias was applied to the single-layer photosensitive member (i.e., during transfer bias application). A surface potential difference ($V_{ON}-V_{OFF}$) was calculated using the measured surface potentials ($V_{OFF}$ and $V_{ON}$). The calculated surface potential difference was taken to be a transfer memory potential. Transfer memory potentials that were calculated are shown in Tables 3 and 4. It should be noted that a transfer memory potential having a smaller absolute value indicates a lower probability of transfer memory occurring.

<7. Image Evaluation>

With respect to each of the single-layer photosensitive members (E-1) to (E-41) and (F-1) to (F-8), the single-layer photosensitive member was installed in the color printer (FS-C5250DN produced by KYOCERA Document Solutions Inc.). The color printer used the same charging section and transfer process as used in evaluation of transfer memory potential described above. The color printer was used to print an image A continuously for one hour in order to stabilize operation of the single-layer photosensitive member. The image A was a text image including alphabetical letters. After printing for one hour, the image A was printed on one sheet. The image A corresponded to a first rotation of the photosensitive member. Next, a halftone image B (halftone portion, image density 12.5%) was printed entirely over one sheet and was used as an evaluation image sample for an image ghost. The image B corresponded to a second rotation of the photosensitive member. The printed evaluation image sample was visually inspected for an image defect (image ghost originating from image A). The following evaluation standard was used for evaluation based on presence of an image defect. Results of image evaluation are shown in Tables 3 and 4. An evaluation of good or particularly good was determined to pass the evaluation.

(Image Evaluation Standard)

Particularly Good: No image defect observed in halftone portion

Good: Void defect of length 10 mm observed as image ghost in halftone portion

Mediocre: Void defect of length 10 mm observed as image ghost and illegible alphabetical letter shaped void defect of length 3 mm observed as image ghost in halftone portion Poor: Clearly legible alphabetical letter shaped void defect of length 3 mm observed as image ghost in halftone portion <8. Evaluation of External Appearance>

With respect to each of the multi-layer photosensitive members (A-1) to (A-10), (B-1), and (B-2), and each of the single-layer photosensitive members (C-1) to (C-30), (D-1)

to (D-6), (E-1) to (E-41), and (F-1) to (F-8), the entire surface region of the photosensitive member was observed under an optical microscope at a magnification of ×50. Through the above observation, it was confirmed whether or not a crystallized portion was present at the surface of the photosensitive member. Based on the results of the above confirmation, the external appearance of each of the multi-layer photosensitive members and single-layer photosensitive members was evaluated in accordance with the following evaluation standard. Results of external appearance evaluation are shown in Tables 1-4.

(External Appearance Evaluation Standard)
Particularly Good: No crystallized portion observed
Good: Almost no crystallized portion observed
Poor: Crystallized portion observed Table 1 shows the hole transport material contained in the charge transport layer and the various evaluation results for each of the multi-layer photosensitive members (A-1) to (A-10), (B-1), and (B-2). Table 2 shows the charge generating material, the hole transport material, and the electron transport material contained in the single-layer type photosensitive layer and the various evaluation results for each of the single-layer photosensitive members (C-1) to (C-30) and (D-1) to (D-6).

Tables 3 and 4 show the charge generating material, the hole transport material, and the electron transport material contained in the single-layer type photosensitive layer and the various evaluation results for each of the single-layer photosensitive members (E-1) to (E-41) and (F-1) to (F-8). It should be noted that X—$H_2$Pc and TiOPc in Tables 3 and 4 respectively indicate X-form metal-free phthalocyanine and Y-form titanyl phthalocyanine.

TABLE 1

| Multi-layer photosensitive member | Hole transport material | $V_0$ [−V] | $V_L$ [−V] | Evaluation of external appearance (presence of crystallization) |
|---|---|---|---|---|
| A-1 | HT-1 | 700 | 87 | Particularly good |
| A-2 | HT-2 | 700 | 88 | Particularly good |
| A-3 | HT-3 | 700 | 89 | Particularly good |
| A-4 | HT-4 | 700 | 91 | Particularly good |
| A-5 | HT-5 | 700 | 105 | Particularly good |
| A-6 | HT-6 | 700 | 110 | Particularly good |
| A-7 | HT-7 | 700 | 101 | Particularly good |
| A-8 | HT-8 | 700 | 93 | Particularly good |
| A-9 | HT-9 | 700 | 89 | Particularly good |
| A-10 | HT-10 | 700 | 96 | Particularly good |
| B-1 | HT-A | 700 | 125 | Particularly good |
| B-2 | HT-B | 700 | 123 | Particularly good |

TABLE 2

| Single layer photosensitive member | Charge generating material | Hole transport material | Electron transport material | $V_0$ [+V] | $V_L$ [+V] | Evaluation of external appearance (presence of crystallization) |
|---|---|---|---|---|---|---|
| C-1 | X-form metal-free phthalocyanine | HT-1 | ETM-1 | 700 | 98 | Particularly good |
| C-2 | X-form metal-free phthalocyanine | HT-1 | ETM-3 | 699 | 98 | Particularly good |
| C-3 | Y-form titanyl phthalocyanine | HT-1 | ETM-3 | 700 | 94 | Particularly good |
| C-4 | X-form metal-free phthalocyanine | HT-2 | ETM-1 | 698 | 99 | Particularly good |
| C-5 | X-form metal-free phthalocyanine | HT-2 | ETM-3 | 700 | 100 | Particularly good |
| C-6 | Y-form titanyl phthalocyanine | HT-2 | ETM-3 | 700 | 95 | Particularly good |
| C-7 | X-form metal-free phthalocyanine | HT-3 | ETM-1 | 700 | 103 | Good |
| C-8 | X-form metal-free phthalocyanine | HT-3 | ETM-3 | 699 | 104 | Good |
| C-9 | Y-form titanyl phthalocyanine | HT-3 | ETM-3 | 700 | 100 | Good |
| C-10 | X-form metal-free phthalocyanine | HT-4 | ETM-1 | 700 | 106 | Good |
| C-11 | X-form metal-free phthalocyanine | HT-4 | ETM-3 | 699 | 108 | Good |
| C-12 | Y-form titanyl phthalocyanine | HT-4 | ETM-3 | 700 | 102 | Good |
| C-13 | X-form metal-free phthalocyanine | HT-5 | ETM-1 | 698 | 104 | Particularly good |
| C-14 | X-form metal-free phthalocyanine | HT-5 | ETM-3 | 700 | 105 | Particularly good |
| C-15 | Y-form titanyl phthalocyanine | HT-5 | ETM-3 | 700 | 101 | Particularly good |
| C-16 | X-form metal-free phthalocyanine | HT-6 | ETM-1 | 700 | 109 | Particularly good |
| C-17 | X-form metal-free phthalocyanine | HT-6 | ETM-3 | 699 | 108 | Particularly good |
| C-18 | Y-form titanyl phthalocyanine | HT-6 | ETM-3 | 699 | 104 | Particularly good |
| C-19 | X-form metal-free phthalocyanine | HT-7 | ETM-1 | 700 | 97 | Particularly good |
| C-20 | X-form metal-free phthalocyanine | HT-7 | ETM-3 | 699 | 96 | Particularly good |
| C-21 | Y-form titanyl phthalocyanine | HT-7 | ETM-3 | 699 | 92 | Particularly good |
| C-22 | X-form metal-free phthalocyanine | HT-8 | ETM-1 | 700 | 94 | Particularly good |
| C-23 | X-form metal-free phthalocyanine | HT-8 | ETM-3 | 699 | 96 | Particularly good |
| C-24 | Y-form titanyl phthalocyanine | HT-8 | ETM-3 | 700 | 90 | Particularly good |
| C-25 | X-form metal-free phthalocyanine | HT-9 | ETM-1 | 698 | 93 | Particularly good |
| C-26 | X-form metal-free phthalocyanine | HT-9 | ETM-3 | 700 | 94 | Particularly good |
| C-27 | Y-form titanyl phthalocyanine | HT-9 | ETM-3 | 700 | 89 | Particularly good |
| C-28 | X-form metal-free phthalocyanine | HT-10 | ETM-1 | 700 | 103 | Particularly good |
| C-29 | X-form metal-free phthalocyanine | HT-10 | ETM-3 | 699 | 102 | Particularly good |
| C-30 | Y-form titanyl phthalocyanine | HT-10 | ETM-3 | 699 | 98 | Particularly good |
| D-1 | X-form metal-free phthalocyanine | HT-A | ETM-1 | 699 | 125 | Particularly good |
| D-2 | X-form metal-free phthalocyanine | HT-A | ETM-3 | 700 | 122 | Particularly good |
| D-3 | Y-form titanyl phthalocyanine | HT-A | ETM-3 | 701 | 119 | Particularly good |
| D-4 | X-form metal-free phthalocyanine | HT-B | ETM-1 | 699 | 125 | Particularly good |
| D-5 | X-form metal-free phthalocyanine | HT-B | ETM-3 | 700 | 122 | Particularly good |
| D-6 | Y-form titanyl phthalocyanine | HT-B | ETM-3 | 701 | 119 | Particularly good |

TABLE 3

| Single-layer photosensitive member | Hole transport material | Electron transport material | Charge generating material | Evaluation of external appearance (presence of crystallization) | Transfer memory potential [V] | Image evaluation |
|---|---|---|---|---|---|---|
| E-1 | HT-1 | ETM-1 | X-$H_2$Pc | Particularly good | −11 | Particularly good |
| E-2 | HT-1 | ETM-2 | X-$H_2$Pc | Particularly good | −10 | Particularly good |
| E-3 | HT-1 | ETM-3 | X-$H_2$Pc | Particularly good | −12 | Particularly good |
| E-4 | HT-1 | ETM-4 | X-$H_2$Pc | Particularly good | −10 | Particularly good |
| E-5 | HT-2 | ETM-1 | X-$H_2$Pc | Particularly good | −12 | Particularly good |
| E-6 | HT-2 | ETM-2 | X-$H_2$Pc | Particularly good | −11 | Particularly good |
| E-7 | HT-2 | ETM-3 | X-$H_2$Pc | Particularly good | −13 | Particularly good |
| E-8 | HT-2 | ETM-4 | X-$H_2$Pc | Particularly good | −13 | Particularly good |
| E-9 | HT-3 | ETM-1 | X-$H_2$Pc | Good | −12 | Particularly good |
| E-10 | HT-3 | ETM-2 | X-$H_2$Pc | Good | −11 | Particularly good |
| E-11 | HT-3 | ETM-3 | X-$H_2$Pc | Good | −12 | Particularly good |
| E-12 | HT-3 | ETM-4 | X-$H_2$Pc | Good | −11 | Particularly good |
| E-13 | HT-4 | ETM-1 | X-$H_2$Pc | Good | −13 | Particularly good |
| E-14 | HT-4 | ETM-2 | X-$H_2$Pc | Good | −12 | Particularly good |
| E-15 | HT-4 | ETM-3 | X-$H_2$Pc | Good | −14 | Particularly good |
| E-16 | HT-4 | ETM-4 | X-$H_2$Pc | Good | −13 | Particularly good |
| E-17 | HT-5 | ETM-1 | X-$H_2$Pc | Particularly good | −14 | Particularly good |
| E-18 | HT-5 | ETM-2 | X-$H_2$Pc | Particularly good | −13 | Particularly good |
| E-19 | HT-5 | ETM-3 | X-$H_2$Pc | Particularly good | −14 | Particularly good |
| E-20 | HT-5 | ETM-4 | X-$H_2$Pc | Particularly good | −13 | Particularly good |
| E-21 | HT-6 | ETM-1 | X-$H_2$Pc | Particularly good | −14 | Particularly good |
| E-22 | HT-6 | ETM-2 | X-$H_2$Pc | Particularly good | −14 | Particularly good |
| E-23 | HT-6 | ETM-3 | X-$H_2$Pc | Particularly good | −15 | Particularly good |
| E-24 | HT-6 | ETM-4 | X-$H_2$Pc | Particularly good | −14 | Particularly good |
| E-25 | HT-7 | ETM-1 | X-$H_2$Pc | Particularly good | −10 | Particularly good |

TABLE 4

| Single-layer photosensitive member | Hole transport material | Electron transport material | Charge generating material | Evaluation of external appearance (presence of crystallization) | Transfer memory potential [V] | Image evaluation |
|---|---|---|---|---|---|---|
| E-26 | HT-7 | ETM-2 | X-$H_2$Pc | Particularly good | −10 | Particularly good |
| E-27 | HT-7 | ETM-3 | X-$H_2$Pc | Particularly good | −12 | Particularly good |
| E-28 | HT-7 | ETM-4 | X-$H_2$Pc | Particularly good | −11 | Particularly good |
| E-29 | HT-8 | ETM-1 | X-$H_2$Pc | Particularly good | −11 | Particularly good |
| E-30 | HT-8 | ETM-2 | X-$H_2$Pc | Particularly good | −10 | Particularly good |
| E-31 | HT-8 | ETM-3 | X-$H_2$Pc | Particularly good | −11 | Particularly good |
| E-32 | HT-8 | ETM-4 | X-$H_2$Pc | Particularly good | −12 | Particularly good |
| E-33 | HT-9 | ETM-1 | X-$H_2$Pc | Particularly good | −12 | Particularly good |
| E-34 | HT-9 | ETM-2 | X-$H_2$Pc | Particularly good | −12 | Particularly good |
| E-35 | HT-9 | ETM-3 | X-$H_2$Pc | Particularly good | −12 | Particularly good |
| E-36 | HT-9 | ETM-4 | X-$H_2$Pc | Particularly good | −12 | Particularly good |
| E-37 | HT-10 | ETM-1 | X-$H_2$Pc | Particularly good | −13 | Particularly good |
| E-38 | HT-10 | ETM-2 | X-$H_2$Pc | Particularly good | −12 | Particularly good |
| E-39 | HT-10 | ETM-3 | X-$H_2$Pc | Particularly good | −13 | Particularly good |
| E-40 | HT-10 | ETM-4 | X-$H_2$Pc | Particularly good | −13 | Particularly good |
| E-41 | HT-1 | ETM-1 | TiOPc | Particularly good | −11 | Particularly good |
| F-1 | HT-A | ETM-1 | X-$H_2$Pc | Particularly good | −52 | Poor |
| F-2 | HT-A | ETM-2 | X-$H_2$Pc | Particularly good | −50 | Poor |
| F-3 | HT-A | ETM-3 | X-$H_2$Pc | Particularly good | −54 | Poor |
| F-4 | HT-A | ETM-4 | X-$H_2$Pc | Particularly good | −52 | Poor |
| F-5 | HT-B | ETM-1 | X-$H_2$Pc | Particularly good | −56 | Poor |
| F-6 | HT-B | ETM-2 | X-$H_2$Pc | Particularly good | −54 | Poor |
| F-7 | HT-B | ETM-3 | X-$H_2$Pc | Particularly good | −57 | Poor |
| F-8 | HT-B | ETM-4 | X-$H_2$Pc | Particularly good | −56 | Poor |

Each of the multi-layer photosensitive members (A-1) to (A-10) contained the triarylamine derivative (I). More specifically, the multi-layer photosensitive members (A-1) to (A-10) contained the triarylamine derivatives (HT-1) to (HT-10). As a result, each of the multi-layer photosensitive members (A-1) to (A-10) had a residual potential ($V_L$) with a small absolute value as clearly shown by Table 1. The above indicates that each of the multi-layer photosensitive members (A-1) to (A-10) had excellent electrical properties while also maintaining excellent external appearance (i.e., inhibiting crystallization in the multi-layer type photosensitive layer).

Each of the single-layer photosensitive members (C-1) to (C-30) contained the triarylamine derivative (I). More specifically, the single-layer photosensitive members (C-1) to (C-30) contained the triarylamine derivatives (HT-1) to (HT-10). As a result, each of the single-layer photosensitive members (C-1) to (C-30) had a residual potential ($V_L$) with a small absolute value as clearly shown by Table 2. The above indicates that each of the single-layer photosensitive members (C-1) to (C-30) had excellent electrical properties while also maintaining excellent external appearance (i.e., inhibiting crystallization in the single-layer type photosensitive layer).

In contrast, the multi-layer photosensitive members (B-1) and (B-2) and the single-layer photosensitive members (D-1) to (D-6) did not contain the triarylamine derivative (I). As a result, each of the multi-layer photosensitive members (B-1) and (B-2) and each of the single-layer photosensitive members (D-1) to (D-6) had a residual potential ($V_L$) with a large absolute value and had poor electrical properties as clearly shown by Tables 1 and 2.

Each of the single-layer photosensitive members (E-1) to (E-41) contained the triarylamine derivative (I). More specifically, the single-layer photosensitive members (E-1) to (E-41) contained the triarylamine derivatives (HT-1) to (HT-10). As a result, each of the single-layer photosensitive members (E-1) to (E-41) had a transfer memory potential with a small absolute value as clearly shown by Tables 3 and 4. The above indicates that each of the single-layer photosensitive members (E-1) to (E-41) inhibited occurrence of transfer memory while maintaining excellent external appearance (i.e., inhibiting crystallization in the single-layer type photosensitive layer). As a result, the single-layer photosensitive members (E-1) to (E-41) also effectively inhibited occurrence of image defects such as ghosts.

In contrast, the single-layer photosensitive members (F-1) to (F-8) did not contain the triarylamine derivative (I). As a result, each of the single-layer photosensitive members (F-1) to (F-8) tended to have a transfer memory potential with a large absolute value as clearly shown by Tables 3 and 4. Consequently, transfer memory occurred and image defects such as ghosts were observed.

What is claimed is:

1. A triarylamine derivative represented by general formula (I)

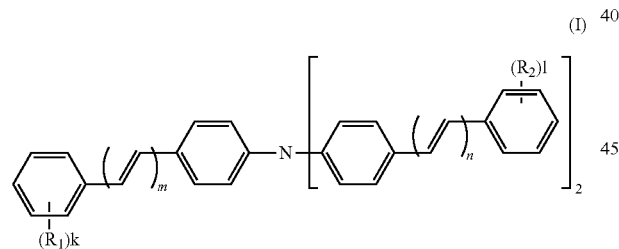

where, in the general formula (I),
$R_1$ and $R_2$ each represent, independently of one another, a chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12,
k represents 0 or 1,
l represents 0,
m and n each represent, independently of one another, an integer of at least 1 and no greater than 3,
m and n represent different integers to one another,
when k represents 0, m represents 1 and n represents 3, and
when k represents 1, n represents a larger integer than m.

2. An electrophotographic photosensitive member comprising
a photosensitive layer containing a charge generating material and a hole transport material, wherein
the photosensitive layer is either a multi-layer type photosensitive layer or a single-layer type photosensitive layer,
the multi-layer type photosensitive layer includes a charge generating layer that contains the charge generating material and a charge transport layer on the charge generating layer, the charge transport layer contains the hole transport material,
the single-layer type photosensitive layer contains the charge generating material and the hole transport material, and
the hole transport material is a triarylamine derivative represented by general formula (I)

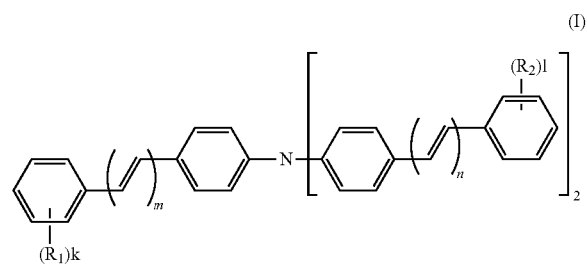

where, in the general formula (I),
$R_1$ and $R_2$ each represent, independently of one another, a chemical group selected from the group consisting of a halogen atom, an optionally substituted alkyl group having a carbon number of at least 1 and no greater than 6, an optionally substituted alkoxy group having a carbon number of at least 1 and no greater than 6, and an optionally substituted aryl group having a carbon number of at least 6 and no greater than 12,
k and l each represent, independently of one another, an integer of at least 0 and no greater than 4,
when k represents an integer greater than 1, chemical groups $R_1$ bonded to the same aromatic ring may be the same or different to one another,
when l represents an integer greater than 1, chemical groups $R_2$ bonded to the same aromatic ring may be the same or different to one another,
m and n each represent, independently of one another, an integer of at least 1 and no greater than 3, and
m and n represent different integers to one another.

3. An image forming apparatus comprising;
an image bearing member;
a charging section configured to charge a surface of the image bearing member;
a light exposure section configured to form an electrostatic latent image on the surface of the image bearing member by exposing the surface of the image bearing member to light while in a charged state;
a developing section configured to develop the electrostatic latent image into a toner image; and
a transfer section configured to transfer the toner image onto a transfer target from the image bearing member, wherein
the image bearing member is the electrophotographic photosensitive member according to claim 2.

4. The image forming apparatus according to claim 3, wherein
the charging section applies a direct current voltage to the image bearing member while in contact with the image bearing member,
the charging section charges the surface of the image bearing member to a positive polarity, and
the photosensitive layer is the single-layer type photosensitive layer.

5. The image forming apparatus according to claim 3, wherein
the transfer target is a recording medium, and
the image bearing member is in contact with the recording medium during transfer of the toner image onto the recording medium from the image bearing member by the transfer section.

6. The image forming apparatus according to claim 3, wherein
the transfer section includes a primary transfer roller and a secondary transfer roller,
the transfer target is an intermediate transfer belt and a recording medium,
the primary transfer roller transfers the toner image onto the intermediate transfer belt from the image bearing member, and
the secondary transfer roller transfers the toner image onto the recording medium from the intermediate transfer belt.

7. The electrophotographic photosensitive member according to claim 2, wherein
the photosensitive layer is a multi-layer type photosensitive layer,
the hole transport material contains a triarylamine derivative, and
the triarylamine derivative is represented by any one of chemical formulae (HT-1), (HT-2), (HT-3), and (HT-9):

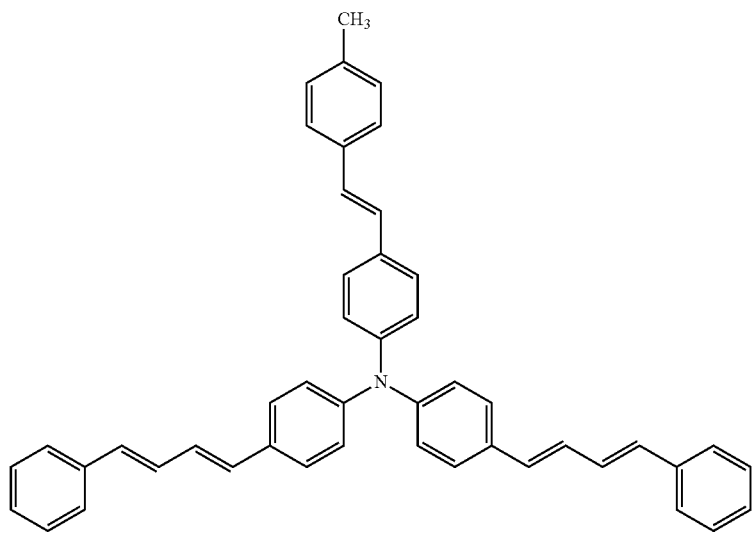

(HT-1)

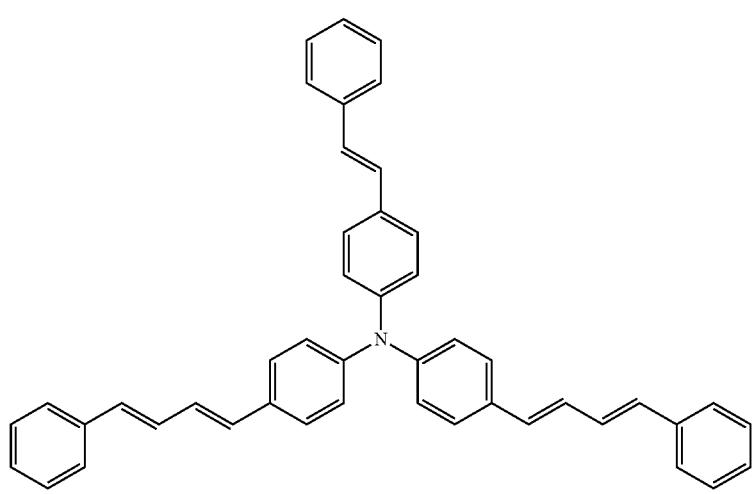

(HT-2)

(HT-3)
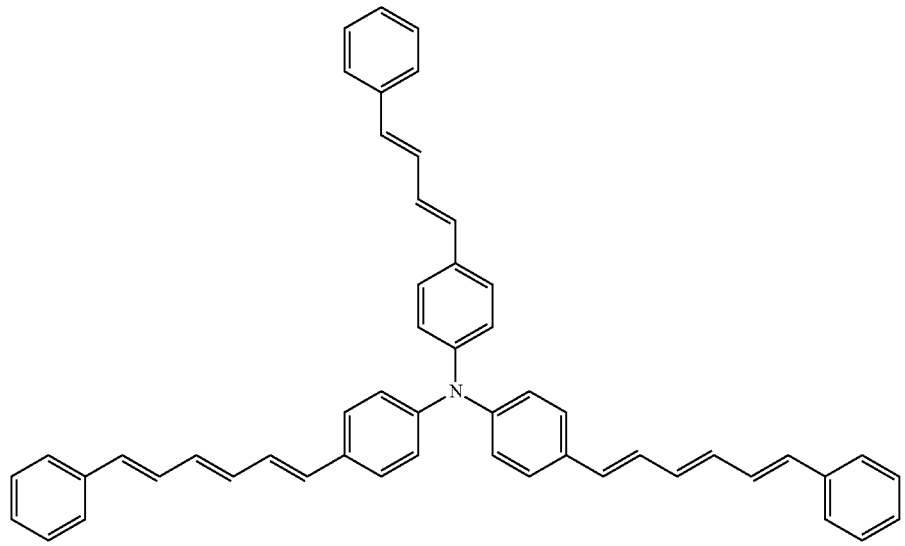
(HT-9)
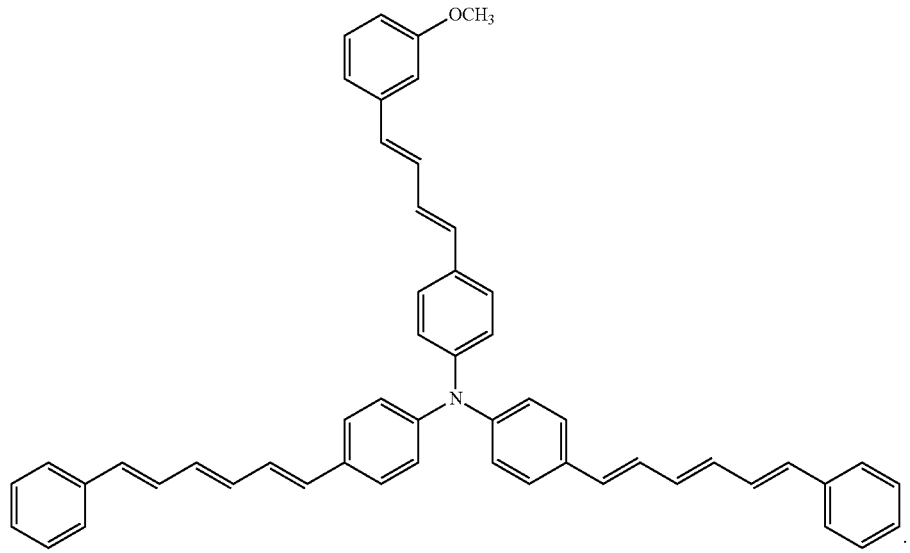
8. The electrophotographic photosensitive member according to claim 2, wherein
the photosensitive layer is a single-layer type photosensitive layer,
the hole transport material contains a triarylamine derivative, and
the triarylamine derivative is represented by any one of chemical formulae (HT-1), (HT-2), and (HT-9):

(HT-1)
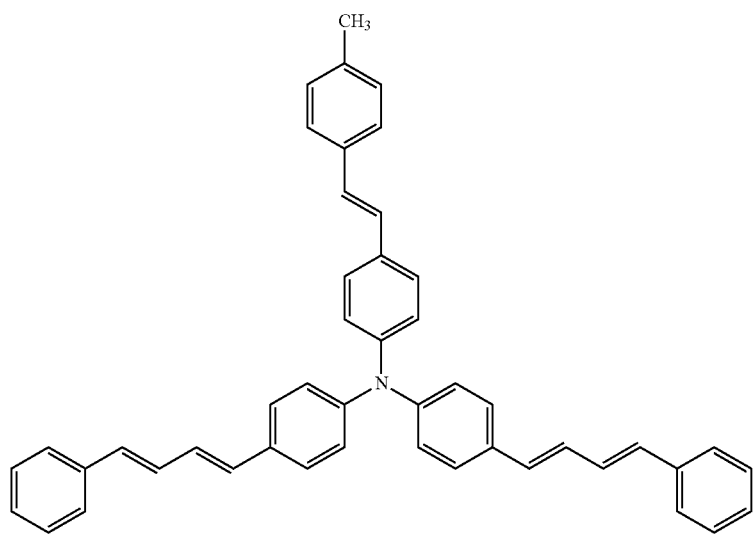
(HT-2)
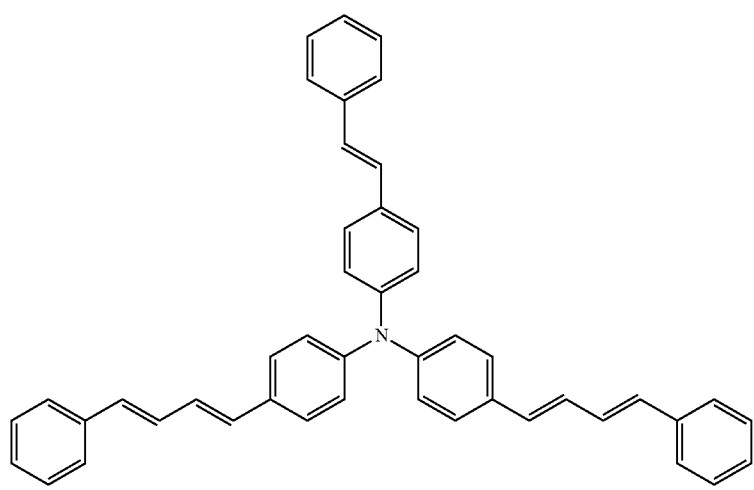
(HT-9)
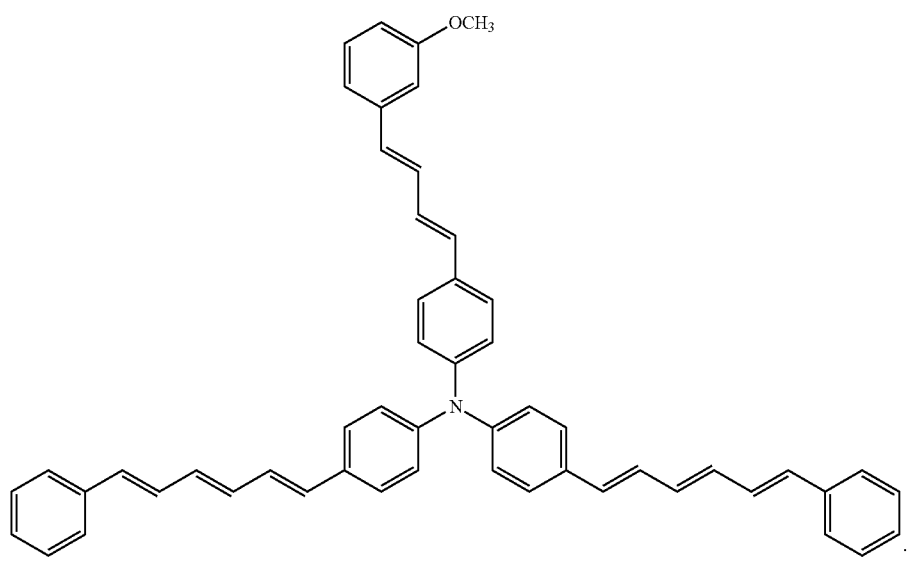
* * * * *